United States Patent
Otsu et al.

(10) Patent No.: US 11,437,584 B2
(45) Date of Patent: Sep. 6, 2022

(54) ORGANIC ELECTROLUMINESCENCE ELEMENT AND MATERIAL FOR ORGANIC ELECTROLUMINESCENCE

(71) Applicant: Konica Minolta, Inc., Tokyo (JP)

(72) Inventors: Shinya Otsu, Koganei (JP); Motoaki Sugino, Akishima (JP); Takamune Hattori, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/336,416

(22) PCT Filed: Oct. 23, 2017

(86) PCT No.: PCT/JP2017/038108
§ 371 (c)(1),
(2) Date: Mar. 25, 2019

(87) PCT Pub. No.: WO2018/079459
PCT Pub. Date: May 3, 2018

(65) Prior Publication Data
US 2020/0020865 A1    Jan. 16, 2020

(30) Foreign Application Priority Data

Oct. 25, 2016 (JP) .............................. JP2016-208482
Mar. 2, 2017 (JP) .............................. JP2017-039554
May 29, 2017 (JP) .............................. JP2017-105451

(51) Int. Cl.
*H01L 51/00* (2006.01)
*H01L 51/50* (2006.01)
(Continued)

(52) U.S. Cl.
CPC ........ *H01L 51/0071* (2013.01); *C07D 471/04* (2013.01); *C07D 491/048* (2013.01);
(Continued)

(58) Field of Classification Search
CPC .............. C07D 491/048; C07D 495/04; H01L 51/0052; H01L 51/0058; H01L 51/0067;
(Continued)

(56) References Cited

U.S. PATENT DOCUMENTS

| | | | |
|---|---|---|---|
| 2012/0187381 A1* | 7/2012 | Xia | ..................... H01L 51/0058 257/40 |
| 2015/0207082 A1* | 7/2015 | Dyatki | ................. C07D 495/14 544/216 |
| 2016/0233436 A1* | 8/2016 | Zeng | .................... C07D 403/04 |

FOREIGN PATENT DOCUMENTS

| | | |
|---|---|---|
| CN | 102260257 B | 5/2013 |
| JP | 2010-166070 A | 7/2010 |

(Continued)

OTHER PUBLICATIONS

Computer-generated English-language translation of WO-2014065073-A1.*

(Continued)

*Primary Examiner* — Vu A Nguyen
(74) *Attorney, Agent, or Firm* — Lucas & Mercanti, LLP

(57) ABSTRACT

An organic electroluminescence element including an anode, a plurality of organic functional layers including a light-emitting layer, and a cathode in that order wherein the organic functional layer containing a compound having a structure represented by the following general formula (1) is arranged between the light-emitting layer and the cathode, wherein X, $X_1$ to $X_{12}$, $R_1$, and $L_1$ are as defined in the specification.

12 Claims, 4 Drawing Sheets

(51) Int. Cl.
  *C07D 491/048* (2006.01)
  *C07D 491/147* (2006.01)
  *C07D 495/04* (2006.01)
  *C07D 495/14* (2006.01)
  *C07D 519/00* (2006.01)
  *C07D 471/04* (2006.01)
  *C09K 11/06* (2006.01)

(52) U.S. Cl.
  CPC ....... *C07D 491/147* (2013.01); *C07D 495/04* (2013.01); *C07D 519/00* (2013.01); *C09K 11/06* (2013.01); *H01L 51/0052* (2013.01); *H01L 51/0058* (2013.01); *H01L 51/0067* (2013.01); *H01L 51/0072* (2013.01); *H01L 51/0073* (2013.01); *H01L 51/0074* (2013.01); *C09K 2211/1018* (2013.01); *H01L 51/5076* (2013.01); *H01L 51/5092* (2013.01)

(58) Field of Classification Search
  CPC ............. H01L 51/0071; H01L 51/0073; H01L 51/0074
  See application file for complete search history.

(56) References Cited

FOREIGN PATENT DOCUMENTS

| | | | |
|---|---|---|---|
| JP | 2011-084531 A | | 4/2011 |
| JP | 2011084531 A | * | 4/2011 |
| JP | 2014-504602 A | | 2/2014 |
| JP | 2014103103 A | * | 6/2014 |
| JP | 2014103104 A | | 6/2014 |
| KR | 20140004005 A | * | 1/2014 |
| KR | 10-2014-0016267 A | | 2/2014 |
| KR | 10-2014-0145355 A | | 12/2014 |
| WO | 2013/161602 A1 | | 10/2013 |
| WO | 2014/065073 A1 | | 5/2014 |
| WO | WO-2014065073 A1 | * | 5/2014 ..... H01L 31/022466 |

OTHER PUBLICATIONS

Computer-generated English-language translation of JP-2014103103-A.*
Computer-generated English-language translation of JP-2011084531-A.*
EPO, Extended European Search Report for the corresponding European patent application No. 17865745.8, dated Sep. 23, 2019 (9 pages).
Office Action for the corresponding Chinese patent application No. 201780065462.3, dated May 27, 2021, with English translation.
International Search Report dated Jan. 23, 2018 for PCT/JP2017/038108 and English translation.
International Preliminary Report on Patentability and Written Opinion of the International Searching Authority dated Apr. 30, 2019 from corresponding International Application No. PCT/JP2017/038108 and English translation.
KIPO, Office Action for the corresponding Korean patent application No. 10-2019-7010852, dated Feb. 18, 2020, with English translation (18 pages).
JPO, Office Action for the corresponding Japanese patent application No. 2018-547642, dated Aug. 3, 2021, with English translation.
CNIPA, Office Action for the corresponding Chinese patent application No. 201780065462.3, dated Nov. 10, 2020, with English translation.
CNIPA, Office Action for the corresponding Chinese patent application No. 201780065462.3, dated Jan. 6, 2022, with English translation.

* cited by examiner

ORGANIC ELECTROLUMINESCENCE ELEMENT AND MATERIAL FOR ORGANIC ELECTROLUMINESCENCE

The present U.S. Patent Application is a U.S. National Phase Application under 35 U.S.C. 371 of International Application No. PCT/JP2017/038108 filed on Oct. 23, 2017. This application claims a priority under the Paris Convention of Japanese Patent Application No. 2016-208482 filed on Oct. 25, 2016, No. 2017-039554 filed on Mar. 2, 2017, and No. 2017-105451 filed on May 29, 2017, the entire disclosure of which is incorporated herein by reference in its entirety.

TECHNICAL FIELD

The present invention relates to an organic electroluminescence element and a material for organic electroluminescence. More particularly, the present invention relates to an organic electroluminescence element with improved drive voltage, durability, and the like.

BACKGROUND ART

An organic electroluminescence element (hereinafter, also referred to as organic EL element) has a structure in which a light-emitting layer containing a compound that emits light is sandwiched between a cathode and an anode. By applying an electric field to the element, excitons are generated as a result of holes injected from the anode and electrons injected from the cathode recombining in the light-emitting layer. The organic EL element utilizes the light (fluorescence/phosphorescence) released when these excitons decay. In addition, since the organic EL element is a completely solid state element composed of films of organic materials having a thickness of only a few submicrons between electrodes, and can emit light at a voltage of about several volts to several tens of volts, organic EL elements are expected to be used for next generation flat displays and lighting.

Since the material for organic electroluminescence (hereinafter, also referred to as organic EL material) is an insulating organic molecule, it is impossible to inject electrons and holes directly into the dopant from the anode and the cathode (charge injection according to the Ohm's law is impossible).

In other words, since the energy barrier between the anode and the light-emitting layer is large, it is impossible to inject holes directly, so in order to inject and transport electric charges into the organic matter that is an insulator, it is necessary to make the film ultra thin (100 nm or less) and to reduce the energy barrier.

Therefore, a thin hole injection and transport layer having intermediate energy is required between the anode and the light-emitting layer. Further, an electron injection and transport layer is similarly required on the electron side as well.

In addition, since it is a fundamental rule that charges move by hopping between π-conjugated sites of organic molecules, all organic EL materials employ compounds having a chemical structure combining aromatic compounds represented by benzene, pyridine, and the like (see, for example, Patent Literature 1).

Specifically, as illustrated in FIG. 1, it is thought that electrons are injected from the cathode to the LUMO energy level of organic molecules to form anion radicals. Since anion radicals are unstable, they transfer electrons to adjacent molecules. If this process is continuously repeated, it appears that only electrons are moving from the right side to the center of the schematic diagram. Thus, in order to drive the organic EL element at a low voltage, in particular, the electron transport material needs to be a material exhibiting fast electron hopping.

For example, Patent Literature 2 and Patent Literature 3 describe the use of a nitrogen-containing aromatic compound, but there is a need for a compound that can further improve performance.

CITATION LIST

Patent Literature

Patent Literature 1: Japanese Patent Laid-Open No. 2010-166070
Patent Literature 2: U.S. Patent Application Publication No. 2015/0207082
Patent Literature 3: International Publication No. WO 2013/161602

SUMMARY OF INVENTION

Technical Problem

The present invention was created in view of the problems and circumstances described above, and it is an object thereof to provide an organic electroluminescence element with improved drive voltage and durability, and a material for organic electroluminescence used in that organic electroluminescence element.

Solution to Problem

In the course of investigating the causes of the problems described above and the like in order to solve them, the present inventor found that electron hopping speed can be improved by including a compound having a specific structure in the organic functional layer, which leads to an improvement in drive voltage and durability, thereby arriving at the present invention.

Specifically, to achieve at least one of the abovementioned objects, an aspect of the present invention is as follows.

1. An organic electroluminescence element comprising an anode, a plurality of organic functional layers including a light-emitting layer, and a cathode in that order,
wherein the organic functional layer containing a compound having a structure represented by the following general formula (1) is arranged between the light-emitting layer and the cathode.

[Formula 1]

General formula (1)

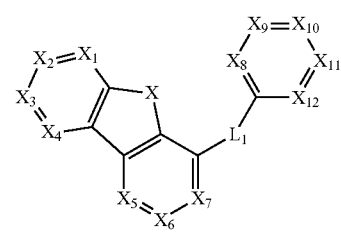

In the general formula (1), X represents an oxygen atom or a sulfur atom. $X_1$ to $X_{12}$ each independently represent $CR_1$ or a nitrogen atom. One of $X_5$ and $X_7$ represents a nitrogen atom and the other represents $CR_1$. One of $X_8$ and $X_{10}$ represents a nitrogen atom and the other represents $CR_1$. $R_1$ represents a hydrogen atom or a substituent. $L_1$ represents a divalent linking group including a benzene ring, a biphenyl ring, a terphenyl ring, a naphthyl ring, an anthracene ring, a triphenylene ring, a fluorene ring, a pyridine ring, a pyrazine ring, a triazine ring, a pyrimidine ring, a dibenzofuran ring, a dibenzothiophene ring, a carbazole ring, an azadibenzofuran ring, an azadibenzothiophene ring, an azacarbazole ring, a thiophene ring, a benzothiophene ring, an indole ring, an imidazole ring, a benzimidazole ring, a pyrazole ring, or a triazole ring. $L^1$ may form a fused ring. Further, the ring containing $X_8$ to $X_{12}$ may be part of a fused ring.

2. An organic electroluminescence element comprising an anode, a plurality of organic functional layers including a light-emitting layer, and a cathode in that order, wherein the organic functional layer containing a compound having a structure represented by the following general formula (1) is arranged between the light-emitting layer and the cathode.

[Formula 2]

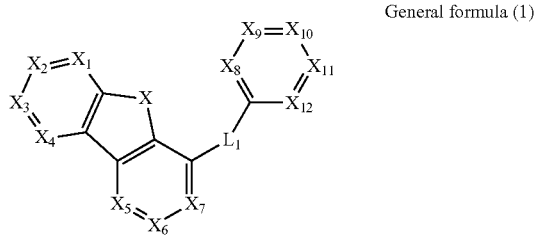

General formula (1)

In the general formula (1), X represents an oxygen atom or a sulfur atom. $X_1$ to $X_{12}$ each independently represent $CR_1$ or a nitrogen atom. One of $X_5$ and $X_7$ represents a nitrogen atom and the other represents $CR_1$. One of $X_8$ and $X_{10}$ represents a nitrogen atom and the other represents $CR_1$. $R_1$ represents a hydrogen atom or a substituent. $L_1$ represents a divalent linking group including a benzene ring, a biphenyl ring, a terphenyl ring, a naphthyl ring, an anthracene ring, a triphenylene ring, a fluorene ring, a pyridine ring, a pyrazine ring, a triazine ring, a pyrimidine ring, a dibenzofuran ring, a dibenzothiophene ring, a carbazole ring, an azadibenzofuran ring, an azadibenzothiophene ring, an azacarbazole ring, a thiophene ring, a benzothiophene ring, an indole ring, an imidazole ring, a benzimidazole ring, a pyrazole ring, or a triazole ring. When $L_1$ is only a benzene ring not having a substituent, at least one of a plurality of $R_1$ represents a heteroaryl group. $L_1$ may form a fused ring. Further, the ring containing $X_8$ to $X_{12}$ may be part of a fused ring.

12. An organic electroluminescence element comprising an anode, a plurality of organic functional layers including a light-emitting layer, and a cathode in that order, wherein the organic functional layer containing a compound having a structure represented by the following general formula (3) is arranged between the light-emitting layer and the cathode.

[Formula 4]

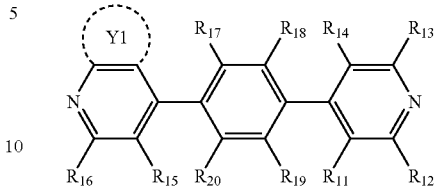

General formula (3)

In the general formula (3), $R_{17}$ to $R_{20}$ each independently represent a hydrogen atom or a substituent. $R_{13}$ and $R_{14}$ may form a ring with each other. Y1 represents a residue forming a 5-membered heterocyclic ring. Further, the 5-membered heterocyclic ring may further have a substituent, and adjacent substituents may form a ring.

24. A material for organic electroluminescence comprising a compound having a structure represented by the following general formula (1).

[Formula 6]

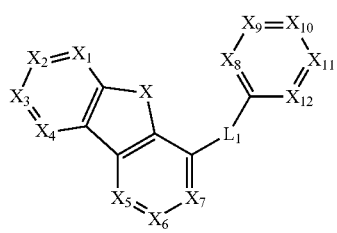

General formula (1)

In the general formula (1), X represents an oxygen atom or a sulfur atom. $X_1$ to $X_{12}$ each independently represent $CR_1$ or a nitrogen atom. One of $X_5$ and $X_7$ represents a nitrogen atom and the other represents $CR_1$. One of $X_8$ and $X_{10}$ represents a nitrogen atom and the other represents $CR_1$. $R_1$ represents a hydrogen atom or a substituent. $L_1$ represents a divalent linking group including a benzene ring, a biphenyl ring, a terphenyl ring, a naphthyl ring, an anthracene ring, a triphenylene ring, a fluorene ring, a pyridine ring, a pyrazine ring, a triazine ring, a pyrimidine ring, a dibenzofuran ring, a dibenzothiophene ring, a carbazole ring, an azadibenzofuran ring, an azadibenzothiophene ring, an azacarbazole ring, a thiophene ring, a benzothiophene ring, an indole ring, an imidazole ring, a benzimidazole ring, a pyrazole ring, or a triazole ring. When $L_1$ is only a benzene ring not having a substituent, at least one of a plurality of $R_1$ represents a heteroaryl group. $L_1$ may form a fused ring. Further, the ring containing $X_8$ to $X_{12}$ may be part of a fused ring.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DESCRIPTION OF EMBODIMENTS

Figure 1:
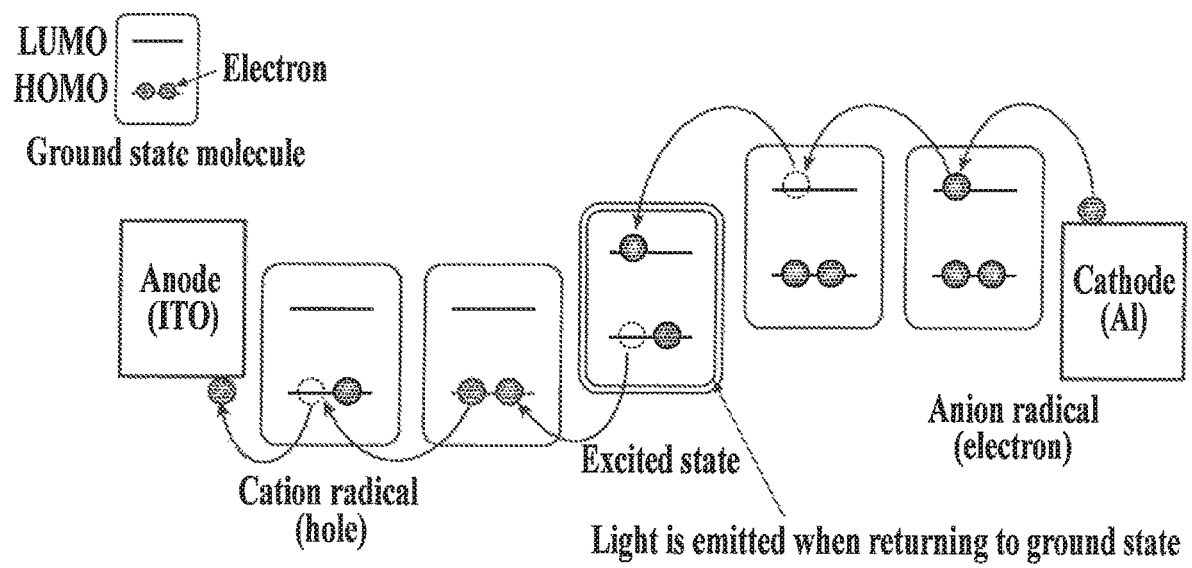
FIG. 1 is a schematic diagram illustrating a charge transport and injection mechanism.

Hereinafter, one or more embodiments of the present invention will be described with reference to the drawings. However, the scope of the invention is not limited to the disclosed embodiments.

An organic electroluminescence element of the present invention comprises an anode, a plurality of organic functional layers including a light-emitting layer, and a cathode in that order, characterized in that the organic functional layer containing a compound having a structure represented by the general formula (1) is arranged between the light-emitting layer and the cathode. This characteristic is a technical characteristic shared by or corresponding to the inventions according to the embodiments.

As an embodiment of the present invention, from the viewpoint of expressing the effects of the present invention, it is preferable for the compound having a structure represented by the general formula (1) to have a structure represented by the general formula (2).

Further, it is preferable that $X_5$ and $X_{10}$ represent a nitrogen atom, as this means that many resonance structures are formed.

Further, it is preferable that $X_7$ and $X_8$ represent a nitrogen atom, as this means that many resonance structures are formed.

Further, it is preferable that $X_5$ and $X_8$ represent a nitrogen atom, as this means that many resonance structures are formed.

Further, it is preferable that $X_7$ and $X_{10}$ represent a nitrogen atom, as this means that many resonance structures are formed.

Further, from the viewpoint of expressing the effects of the present invention, it is preferable for $X_1$ to $X_4$ to represent $CR_1$.

Further, it is preferable that at least one of $X_1$ to $X_4$ represent a nitrogen atom, as this means that many resonance structures are formed.

Further, from the viewpoint of expressing the effects of the present invention, it is preferable for $R_1$ to represent a substituent including a pyridine ring, a pyrazine ring, a triazine ring, a pyrimidine ring, an azadibenzofuran ring, an azadibenzothiophene ring, an azacarbazole ring, a quinazoline ring, a quinoxaline ring, a quinoline ring, an isoquinoline ring, a benzoquinoline ring, a benzisoquinoline ring, an indole ring, an imidazole ring, a benzimidazole ring, a pyrazole ring, a triazole ring, an oxazole ring, a thiazole ring, or a carbazole ring.

In addition, from the viewpoint of expressing the effects of the present invention, in the general formula (1), it is preferable for $X_8$ and $X_{12}$ to represent a nitrogen atom and $X_9$ to $X_{11}$ to represent $CR_1$, or for $X_8$ and $X_{11}$ to represent a nitrogen atom and $X_9$, $X_{10}$, and $X_{12}$ to represent $CR_1$.

The organic electroluminescence element of the present invention comprises an anode, a plurality of organic functional layers including a light-emitting layer, and a cathode in that order, wherein the organic functional layer containing a compound having a structure represented by the general formula (3) is arranged between the light-emitting layer and the cathode.

Further, from the viewpoint of electron hopping, it is preferable that Y1 represent a residue forming an azabenzofuran ring, an azabenzothiophene ring, an azaindole ring, a benzofuran ring, a benzothiophene ring, an indole ring, a pyrazole ring, a triazole ring, an oxazole ring, or a thiazole ring.

In particular, from the viewpoint of electron hopping, it is preferable that Y1 represent a residue forming an azabenzofuran ring or a benzofuran ring.

Further, from the viewpoint of expression the effects of the present invention, it is preferable that the compound having a structure represented by the general formula (3) be a compound having a structure represented by the general formula (4).

In addition, from the viewpoint of electron hopping, it is preferable that Y1 and Y2 each represent a residue forming an azabenzofuran ring, an azabenzothiophene ring, an azaindole ring, a benzofuran ring, a benzothiophene ring, an indole ring, a pyrazole ring, a triazole ring, an oxazole ring, or a thiazole ring.

Further, from the viewpoint of electron hopping, it is preferable that Y1 and Y2 each represent a residue forming an azabenzofuran ring or a benzofuran ring.

In addition, from the viewpoint of π-π interaction, it is preferable that at least one of $R_{17}$ to $R_{20}$ represent an aromatic hydrocarbon or a heterocyclic ring.

Further, from the viewpoint of improving the film quality of the cathode, it is preferable that the cathode comprise silver as a main component, and that the organic functional layer be provided adjacent to the cathode.

In addition, from the viewpoint of improving light transmittance, it is preferable that the cathode have a thickness of 15 nm or less.

Further, from the viewpoint of expressing the effects of the present invention, it is preferable that the cathode have a light transmittance of 50% or more, and that the cathode have a sheet resistance value of 25 n or less.

The organic functional layer preferably has a layer containing the compound having a structure represented by the general formula (1) and an electron injection material, because this strengthens the intermolecular interaction.

It is preferable to stack the organic functional layer containing the compound having a structure represented by the general formula (1), an electron injection layer containing an electron injection material, and the cathode in that order, because this further strengthens the intermolecular interaction.

From the viewpoint of expressing the effects of the present invention, the material for organic electroluminescence of the present invention preferably contains a compound having a structure represented by the above-mentioned general formula (1). In particular, in the general formula (1), it is preferable for $X_8$ and $X_{12}$ to represent a nitrogen atom and $X_9$ to $X_{11}$ to represent $CR_1$, or for $X_8$ and $X_{11}$ to represent a nitrogen atom and $X_9$, $X_{10}$, and $X_{12}$ to represent $CR_1$.

Hereinafter, the present invention, its constituent elements, and embodiments and modes for carrying out the present invention will be described in detail. In the present application, the term "to" used in numerical ranges includes the numerical values before and after as a lower limit value and an upper limit value.

<<Compound Having Structure Represented by General Formula (1)>>

The organic electroluminescence element of the present invention comprises an anode, a plurality of organic functional layers including a light-emitting layer, and a cathode in that order, wherein the organic functional layer containing a compound having a structure represented by the following general formula (1) is arranged between the light-emitting layer and the cathode.

[Formula 7]

General formula (1)

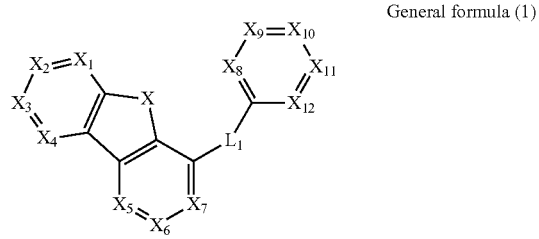

In the general formula (1), X represents an oxygen atom or a sulfur atom. $X_1$ to $X_{12}$ each independently represent $CR_1$ or a nitrogen atom. One of $X_5$ and $X_7$ represents a nitrogen atom and the other represents $CR_1$. One of $X_8$ and $X_{10}$ represents a nitrogen atom and the other represents $CR_1$. $R_1$ represents a hydrogen atom or a substituent. $L_1$ represents a divalent linking group including a benzene ring, a biphenyl ring, a terphenyl ring, a naphthyl ring, an anthracene ring, a triphenylene ring, a fluorene ring, a pyridine ring, a pyrazine ring, a triazine ring, a pyrimidine ring, a dibenzofuran ring, a dibenzothiophene ring, a carbazole ring, an azadibenzofuran ring, an azadibenzothiophene ring, an azacarbazole ring, a thiophene ring, a benzothiophene ring, an indole ring, an imidazole ring, a benzimidazole ring, a pyrazole ring, or a triazole ring. When $L_1$ is only a benzene ring not having a substituent, at least one of a plurality of $R_1$ represents a heteroaryl group.

a benzisoquinoline ring, an indole ring, an imidazole ring, a benzimidazole ring, a pyrazole ring, a triazole ring, an oxazole ring, a thiazole ring, or a carbazole ring.

Further, in the general formula (1), it is preferable for $X_8$ and $X_{12}$ to represent a nitrogen atom and $X_9$ to $X_{11}$ to represent $CR_1$, or for $X_8$ and $X_{11}$ to represent a nitrogen atom and $X_9$, $X_{10}$, and $X_{12}$ to represent $CR_1$.

A part of the representative structure of the compound having a structure represented by the general formula (1) is shown below, but it may be understood that such a compound has a large number of resonance structures. In other words, there are various polarization structures (+, −) in the molecule. The compound having a structure represented by the general formula (1) according to the present invention may have two or more of the following parts, and in such a case it will have even more various polarization structures. Because of the large number of resonance structures, there are many molecules having a different structure, and from a macro perspective, the compound forms a disordered film, but from a micro perspective, intermolecular interaction is strengthened.

As a result, the "+" charges and the "−" charges strongly interacted between the molecules, which further strengthens the intermolecular stack.

More specifically, since the entropy effect is increased, variation in film quality in the organic functional layer can be suppressed, and a voltage rise during driving can be suppressed.

In view of the above, the compound having a structure represented by the general formula (1) according to the present invention is thought to strengthen intermolecular interaction and speed up electronic hopping by utilizing three electrostatic interactions using (I) π-π interaction, (II) n-π interaction, and (III) intramolecular polarization.

[Formula 8]

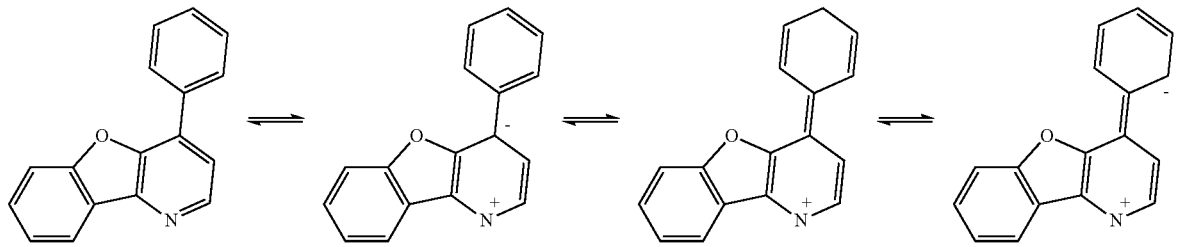

$L_1$ may form a fused ring. Further, the ring containing $X_8$ to $X_{12}$ may be part of a fused ring.

Examples of the substituent used in the general formulas (1) and (2) include, but are not limited to, an alkyl group (e.g., a methyl group, an ethyl group, a trifluoromethyl group, an isopropyl group, etc.), an aryl group (e.g., a phenyl group), a heteroaryl group (e.g., a pyridyl group, a carbazolyl group, etc.), a halogen atom (e.g., a fluorine atom, etc.), a cyano group, or an alkyl fluoride group. Also preferred are the substituents used in the example compounds (described later).

It preferable for $R_1$ to represent a substituent including a pyridine ring, a pyrazine ring, a triazine ring, a pyrimidine ring, an azadibenzofuran ring, an azadibenzothiophene ring, an azacarbazole ring, a quinazoline ring, a quinoxaline ring, a quinoline ring, an isoquinoline ring, a benzoquinoline ring, Further, the introduction of a rigid fused ring causes an increase in the glass transition point, and moreover, since the compound has many resonance structures as described above, variation in film quality in the organic functional layer can be suppressed as a result of the entropy effect, thereby enabling an increase in the voltage when driving to be suppressed.

In addition, as described above, since the compound has various intramolecular polarizations, interaction with the electron injection material (lithium fluoride (LiF), potassium fluoride (KF), lithium quinolate complex (LiQ), etc.). By using together with an electron injection material, electrons can be supplied from the electron injection material to the compound having a structure represented by the general formula (1) according to the present invention, which makes it possible to drive at an even lower voltage.

Further, as shown in the following diagram, it was found that the patent of the present invention interacts with metals such as $L^1$, K, Ag and Mg in a space between the N atom and —CH.

[Formula 9]

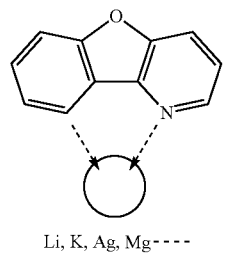

In addition, from a different point of view as well, as described in International Publication No. WO 2013/161602, introducing a rigid fused ring is also useful for an electrode containing silver as a main component. This is because, as described in the above patent literature, in addition to the strong interaction between the silver atom and the nitrogen-containing compound having a structure represented by the general formula (1) according to the present invention, since the compound has various intramolecular polarizations, the interaction with the silver atom also strengthens.

As a result, the diffusion distance of the silver atom decreases further, enabling agglomeration of silver to be suppressed, and the electrode containing silver as a main component can have a uniform film. It means that it is preferable to include a large amount of nitrogen atoms, which have a strong interaction with silver atoms.

<<Compound Having Structure Represented by General Formula (2)>>

It is preferable for the compound having a structure represented by the general formula (1) to have a structure represented by the following general formula (2).

[Formula 10]

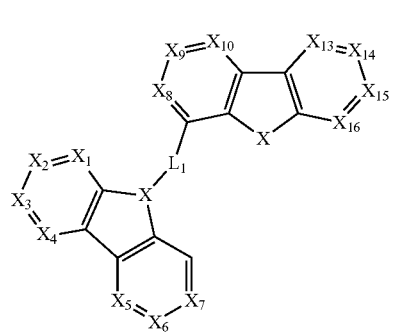

General formula (2)

In the general formula (2), X represents an oxygen atom or a sulfur atom. $X_1$ to $X_{10}$ and $X_{13}$ to $X_{16}$ each independently represent $CR_1$ or a nitrogen atom. One of $X_5$ and $X_7$ represents a nitrogen atom and the other represents $CR_1$. One of $X_8$ and $X_{10}$ represents a nitrogen atom and the other represents $CR_1$. $R_1$ represents a hydrogen atom or a substituent. $L_1$ is a simple atomic bond, or represents a divalent linking group including a benzene ring, a biphenyl ring, a naphthyl ring, a terphenyl ring, an anthracene ring, a triphenylene ring, a fluorene ring, a pyridine ring, a pyrazine ring, a triazine ring, a pyrimidine ring, a dibenzofuran ring, a dibenzothiophene ring, a carbazole ring, an azadibenzofuran ring, an azadibenzothiophene ring, an azacarbazole ring, a thiophene ring, a benzothiophene ring, an indole ring, an imidazole ring, a benzimidazole ring, a pyrazole ring, or a triazole ring. When $L_1$ is only a benzene ring not having a substituent, at least one of a plurality of $R_1$ represents a heteroaryl group.

In particular, $L_1$ is preferably a biphenyl ring, since this increases the strength of the π-π interaction and the n-π interaction formed with neighboring compounds.

$L_1$ may form a fused ring. Further, the rings including $X_8$ to $X_{10}$ and $X_{13}$ to $X_{16}$ may each be part of a fused ring.

Specific examples of $L_1$ are now shown below. However, these are only examples, and the present invention is not limited thereto.

[Formula 11]

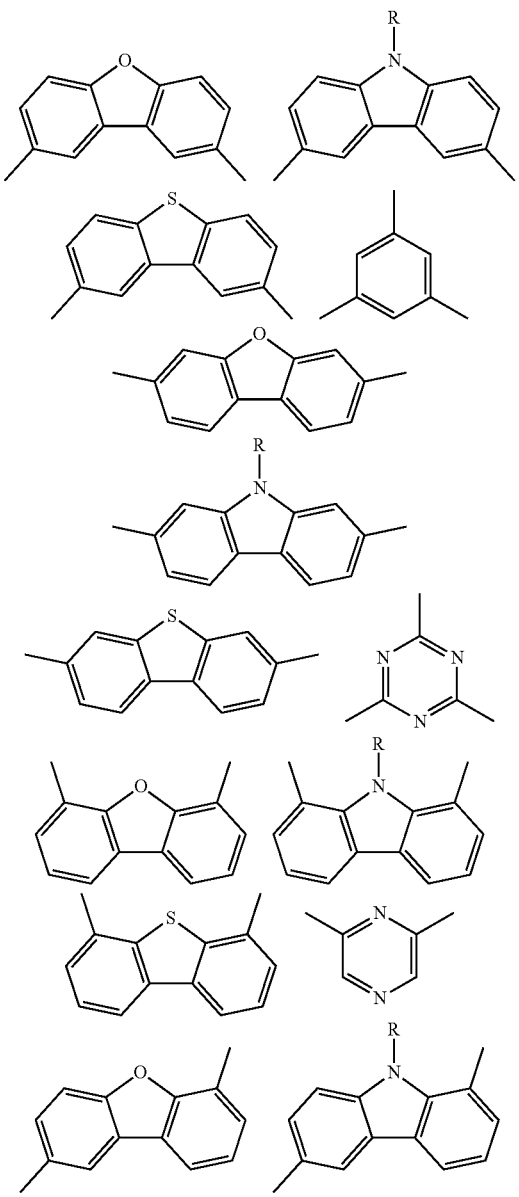

11
-continued
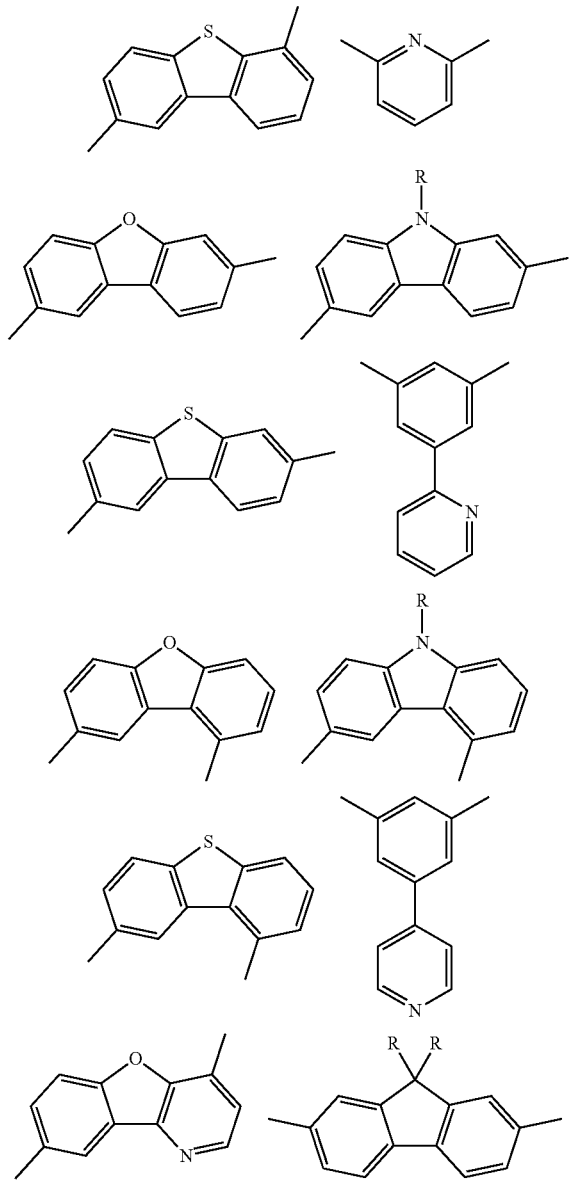
12
-continued
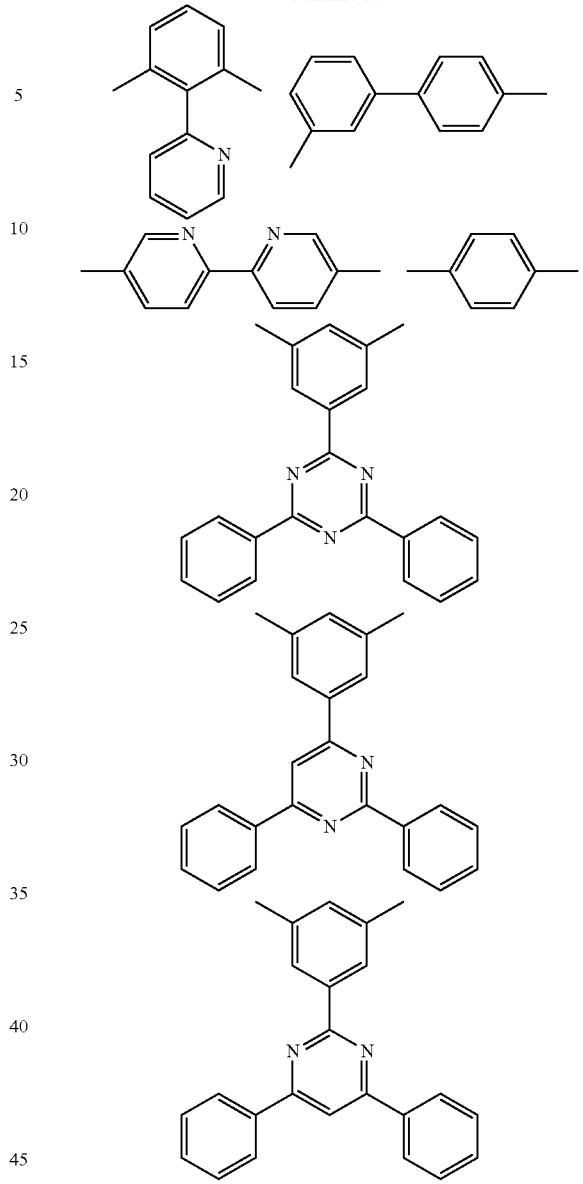
[Formula 12]
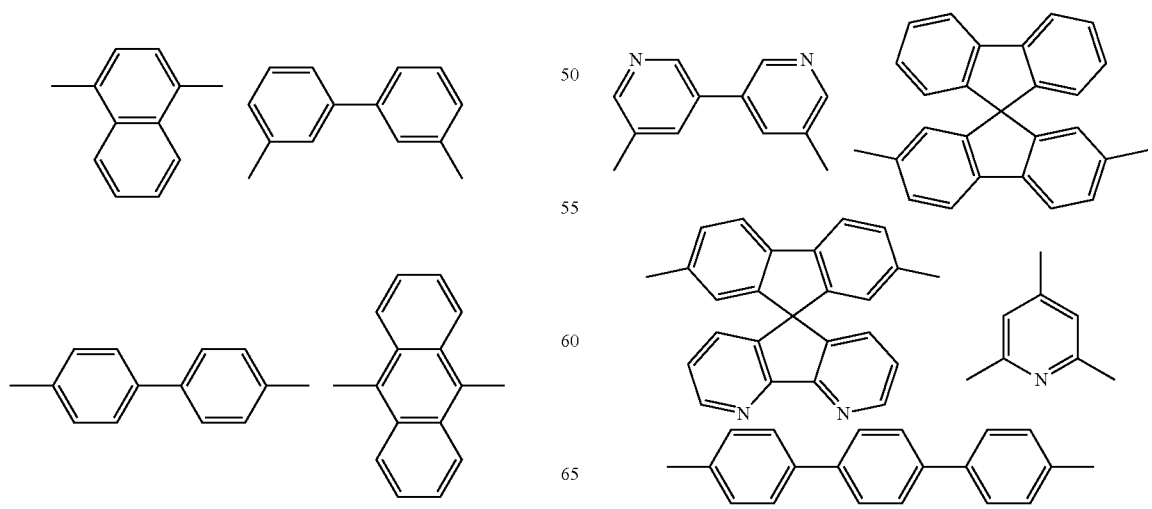

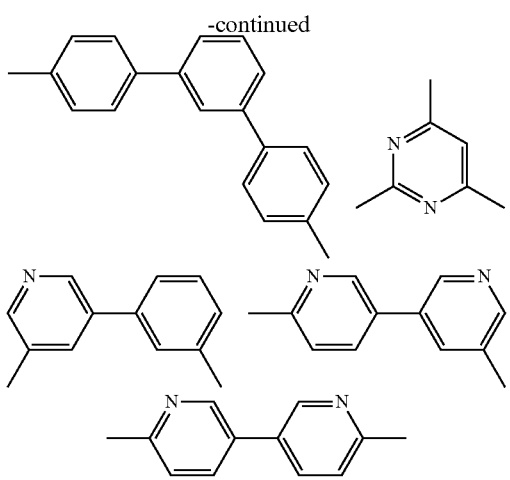

It is noted that by employing a structure in which one of $X_5$ and $X_7$ represents a nitrogen atom and the other represents $CR_1$, it is considered that the resonance structure works effectively, the intermolecular interaction is strengthened, and the entropy effect is increased. The same applies for $X_8$ and $X_{10}$.

In the general formulas (1) and (2), from the viewpoint of having many resonance structures, it is preferable that the combination of $X_5$ and $X_{10}$, $X_7$ and $X_8$, $X_5$ and $X_8$, or $X_7$ and $X_{10}$ represent a nitrogen atom. Further, it is also preferable that at least one of $X_1$ to $X_4$ represent a nitrogen atom.

Further, it is also preferable for $X_1$ to $X_4$ to represent $CR_1$. $R_1$ represents a hydrogen atom or a substituent. $R_1$ preferably represents a substituent including a pyridine ring, a pyrazine ring, a triazine ring, a pyrimidine ring, an azadibenzofuran ring, an azadibenzothiophene ring, an azacarbazole ring, a quinazoline ring, a quinoxaline ring, a quinoline ring, an isoquinoline ring, a benzoquinoline ring, a benzisoquinoline ring, an indole ring, an imidazole ring, a benzimidazole ring, a pyrazole ring, a triazole ring, an oxazole ring, a thiazole ring, or a carbazole ring.

It is also preferable to use the compound having a structure represented by the general formula (1) according to the present invention as a material for organic electroluminescence.

The compound having a structure represented by the following general formula (3) or general formula (4) has structure in common with the main skeleton (host skeleton) of the compound having a structure represented by the general formula (1) according to the present invention when the divalent linking group $L_1$ represents a benzene ring, $X_5$ and $X_{10}$ represent a nitrogen atom, $X_6$, $X_7$, $X_7$, $X_9$, $X_{11}$, and $X_{12}$ represent $CR_1$, and $R_1$ represents a hydrogen atom or a substituent. Therefore, it was found that the compound having a structure represented by the following general formula (3) or general formula (4) also has properties similar to those of the compound having a structure represented by the general formula (1) as a material for organic electroluminescence.

Hereinafter, the compound having a structure represented by the general formula (3) or general formula (4) will be described.

<<Compound Having Structure Represented by General Formula (3)>>

The organic electroluminescence element of the present invention comprises an anode, a plurality of organic functional layers including a light-emitting layer, and a cathode in that order, wherein the organic functional layer containing a compound having a structure represented by the following general formula (3) is arranged between the light-emitting layer and the cathode.

[Formula 13]

General formula (3)

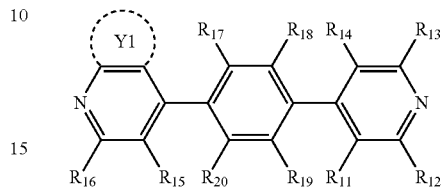

In the general formula (3), $R_{11}$ to $R_{20}$ each independently represent a hydrogen atom or a substituent. Y1 represents a residue forming a 5-membered heterocyclic ring. Further, the 5-membered heterocyclic ring may further have a substituent, and adjacent substituents may form a ring.

It is preferable that Y1 represent a residue forming an azabenzofuran ring, an azabenzothiophene ring, an azaindole ring, a benzofuran ring, a benzothiophene ring, an indole ring, a pyrazole ring, a triazole ring, an oxazole ring, or a thiazole ring. In particular, from the viewpoint of electron hopping, it is preferable that Y1 represent a residue forming an azabenzofuran ring or a benzofuran ring.

<<Compound Having Structure Represented by General Formula (4)>>

It is preferable that the compound having a structure represented by the general formula (3) have a structure represented by the following general formula (4).

[Formula 14]

General formula (4)

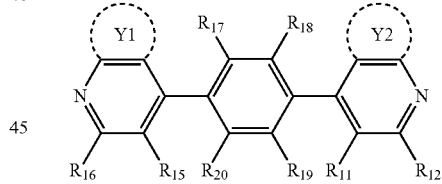

In the general formula (4), $R_{11}$, $R_{12}$ and $R_{15}$ to $R_{20}$ each independently represent $CR_a$ or a nitrogen atom.

$R_a$ represents a hydrogen atom or a substituent.

Y1 and Y2 represent a residue forming a 5-membered heterocyclic ring. Further, the 5-membered heterocyclic ring may further have a substituent, and adjacent substituents may form a ring.

It is preferable that Y1 and Y2 each represent a residue forming an azabenzofuran ring, an azabenzothiophene ring, an azaindole ring, a benzofuran ring, a benzothiophene ring, an indole ring, a pyrazole ring, a triazole ring, an oxazole ring, or a thiazole ring.

From the viewpoint of electron hopping, it is preferable that Y1 and Y2 each represent a residue forming an azabenzofuran ring or a benzofuran ring.

In the general formula (3) and the general formula (4), it is preferable that at least one of $R_{17}$ to $R_{20}$ represent an aromatic hydrocarbon or a heterocyclic ring.

<<Synthesis Examples of Compound Having Structure Represented by General Formula (1)>>

(Synthesis Examples of Example Compound M-32)

[Formula 15]

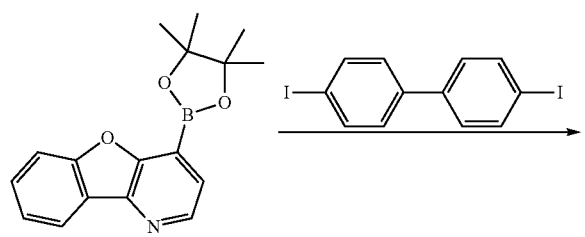

Synthesis Examples of Example Compound M-197

[Formula 16]

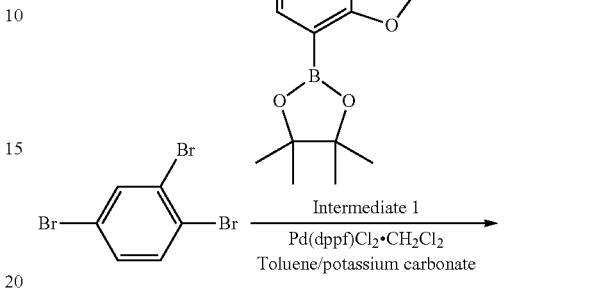

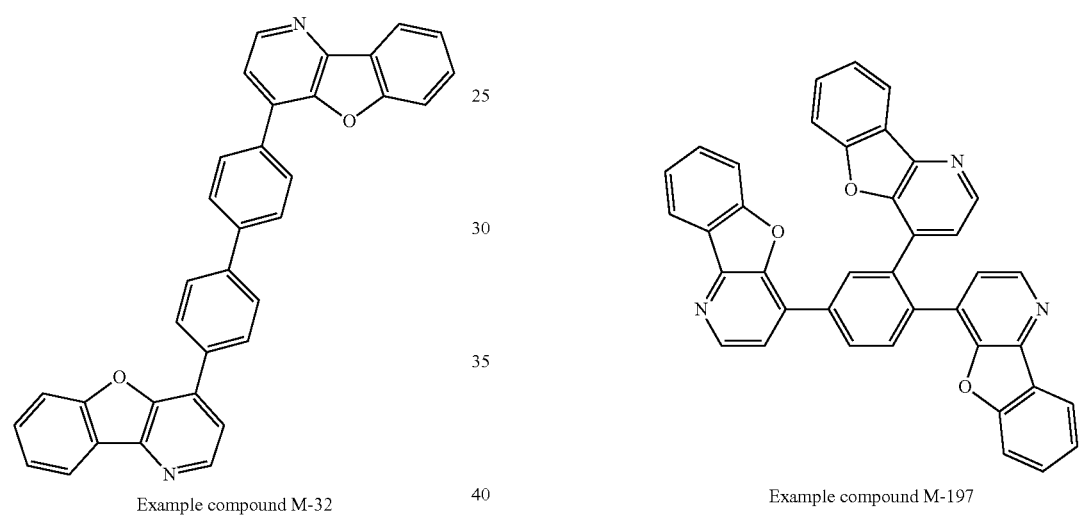

Example compound M-32

Example compound M-197

A 300 mL flask was charged with 7.0 g (23.8 mol) of boronic acid, 3.8 g (9.5 mol) of 4,4'-diiodobiphenyl, 6.9 g (50.0 mol) of potassium carbonate, 100 mL of 1,4-dioxane, and 50 mL of water, and the resultant mixture was then stirred for 30 minutes under a nitrogen stream.

Next, 0.78 g (0.95 mol) of [1,1'-bis(diphenylphosphino) ferrocene]palladium(II) dichloride dichloromethane adduct was charged into the flask, and the mixture was heated under reflux for 7 hours. Then, the mixture was allowed to cool to room temperature, 300 mL of water was added, and the mixture was stirred for 30 minutes. The precipitate was collected by filtration, and the precipitate was washed with 200 mL of tetrahydrofuran to obtain 3.5 g of Example Compound M-32 (yield 75.2%).

$^1$H-NMR (CD$_2$Cl$_2$, 400 MHz) δ: 8.74 (d, 2H), 8.31 (d, 2H), 8.19 (d, 4H), 7.94 (d, 4H), 7.70 (d, 2H), 7.64 (d, 4H), 7.49-7.51 (m, 4H).

Under a nitrogen atmosphere, 6.0 g (19.1 mmol) of 1,2,4-tribromobenzene and 19.5 g (66 mmol) of Intermediate 1 were dissolved in 300 mL of toluene, 15.2 g of potassium carbonate and 75 mL of water were added, then 1.56 g (1.91 mmoL) of [1,1'-bis(diphenylphosphino)ferrocene]palladium(II) dichloride dichloromethane adduct was added, and the mixture was heated under reflux for 7 hours. After the reaction solution had cooled to room temperature, the organic phase was washed with water, the solvent was distilled off, and the obtained residue was purified by silica gel column chromatography to obtain 8.28 g of Example Compound M-197.

$^1$H-NMR (CDCl$_3$) δ: 8.80 (d, 1H), 8.47-8.44 (m, 3H), 8.39 (d, 1H), 8.34 (d, 1H), 8.17-8.15 (m, 2H), 7.72-7.60 (m, 3H), 7.53-7.46 (m, 3H), 7.42-7.38 (m, 2H), 7.29-7.20 (m, 3H)

<<Specific Examples of Compounds Having Structure Represented by General Formula (1) or General Formula (3)>>

Specific examples of compounds having a structure represented by the general formula (1) or the general formula (3) are shown below. These compounds are only examples, and the present invention is not limited thereto.

[Formula 17]
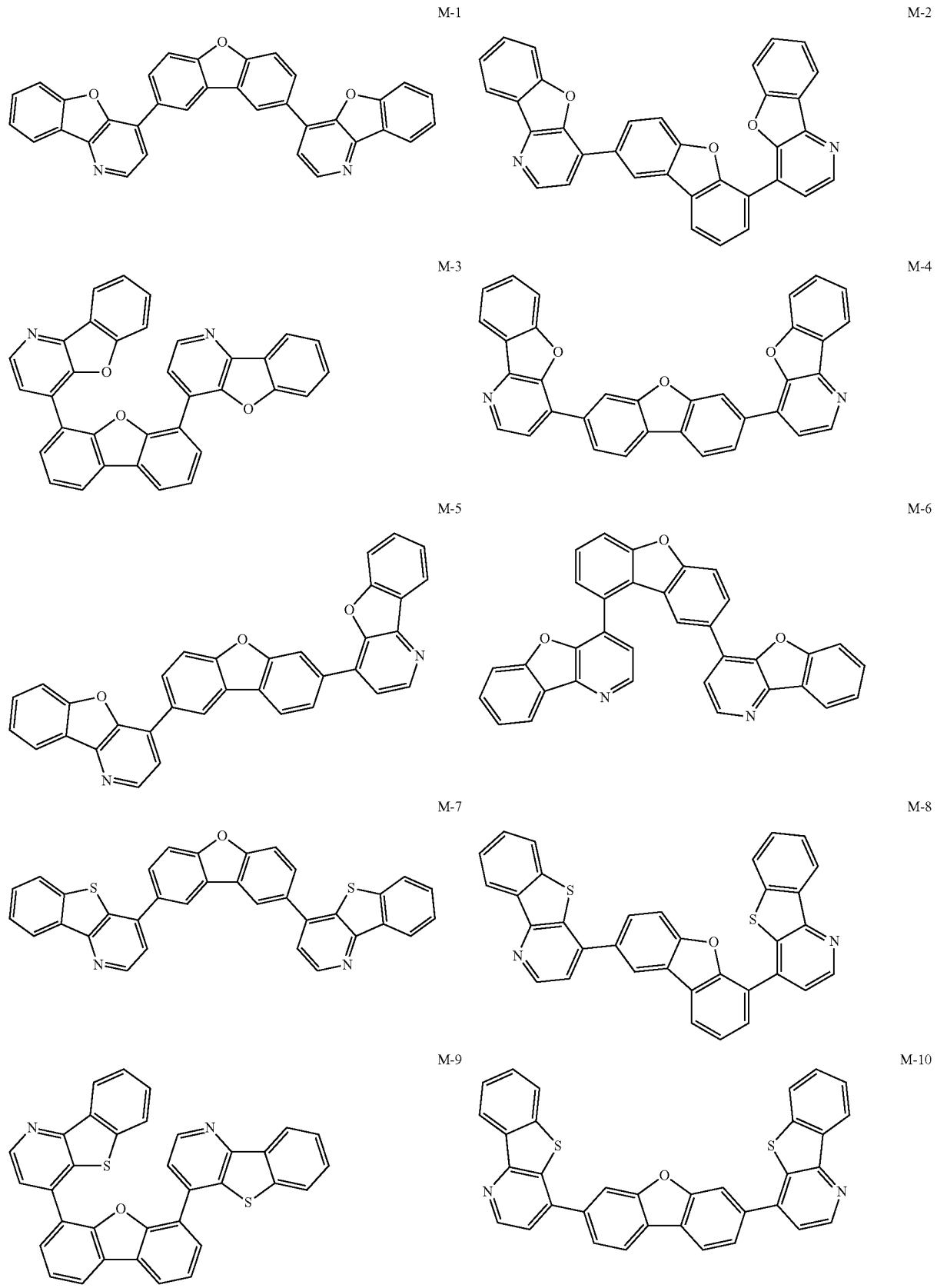

-continued
M-11
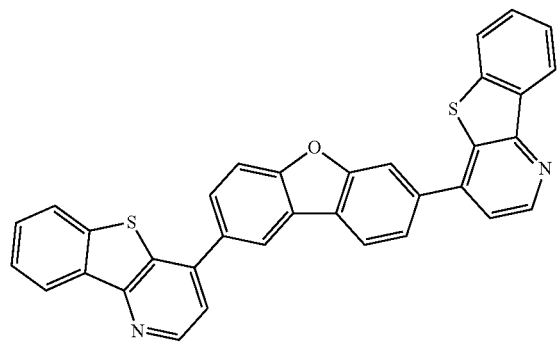
M-12
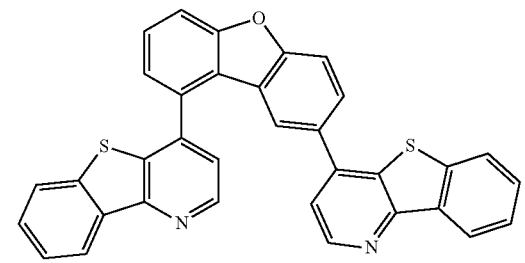
[Formula 18]
M-13
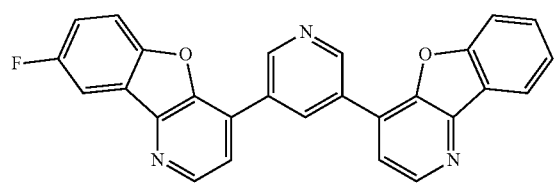
M-14
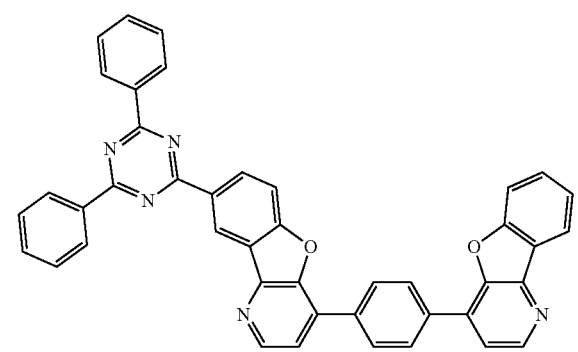
M-15
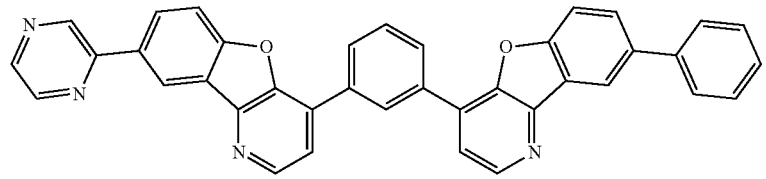
M-16
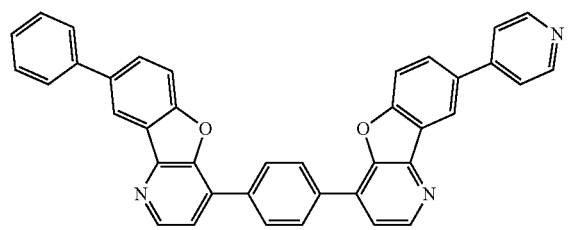
M-17
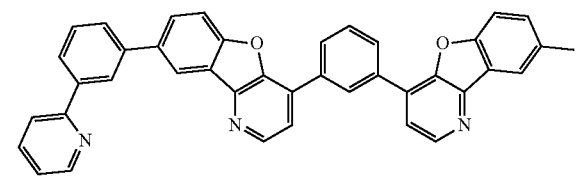
M-18
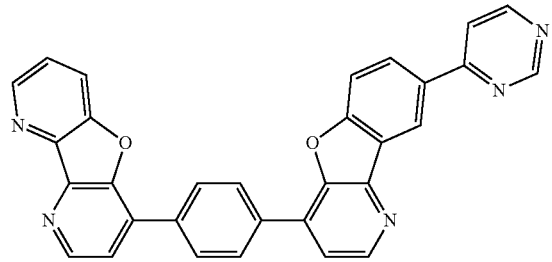

[Formula 19]
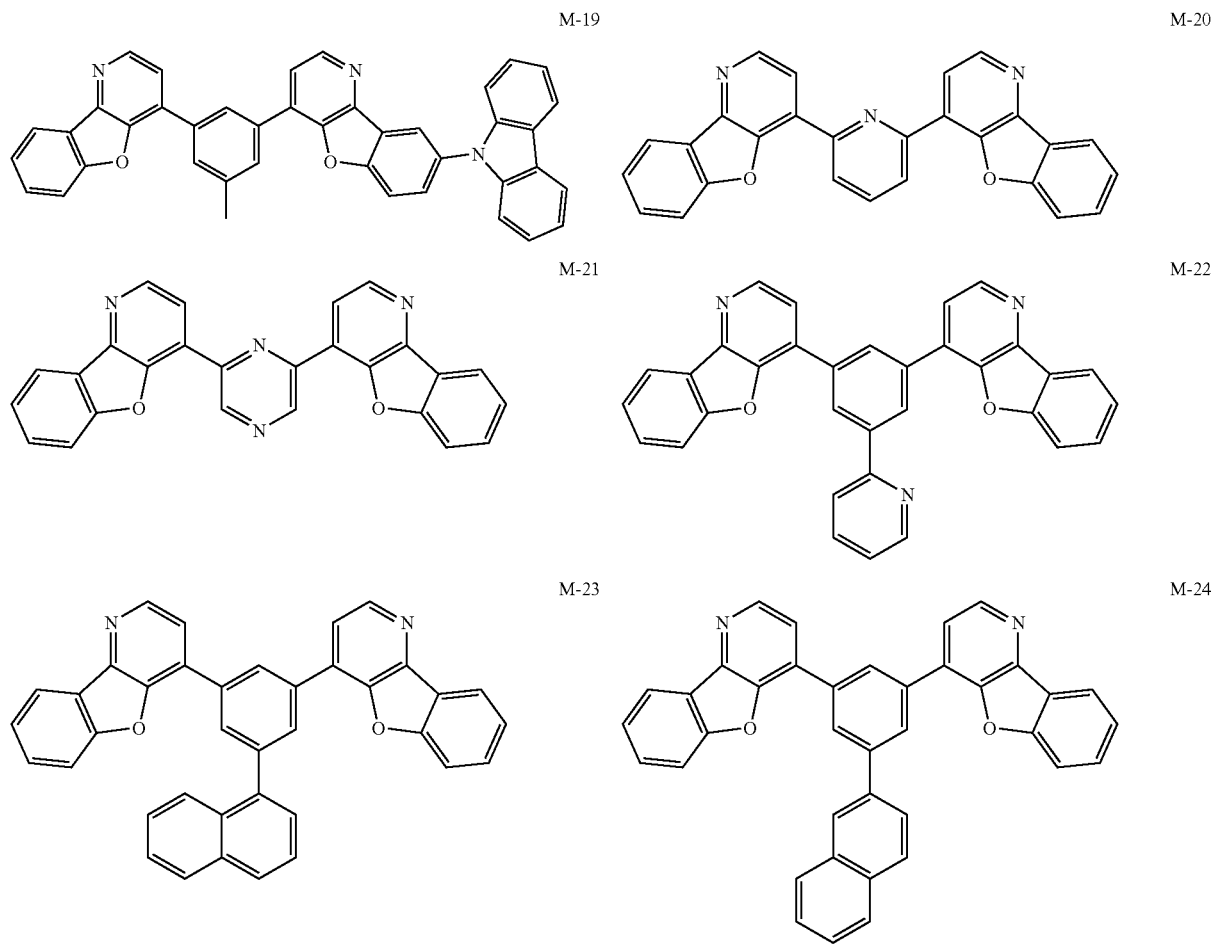
[Formula 20]
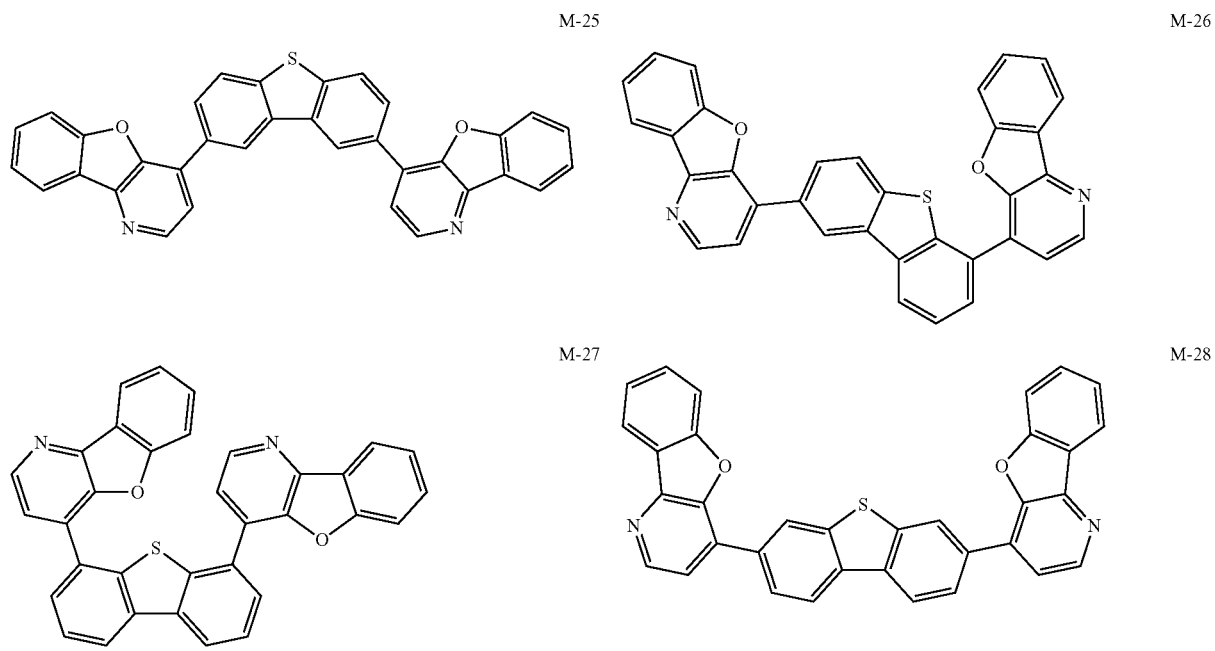

-continued
M-29
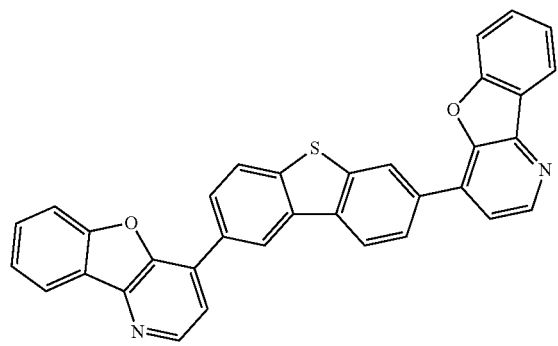
M-30
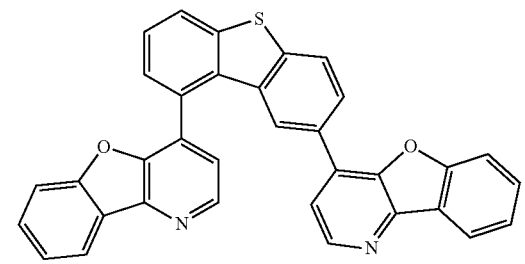
[Formula 21]
M-31
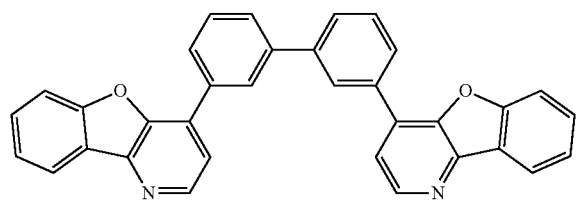
M-32
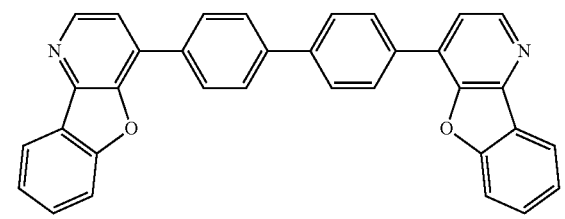
M-33
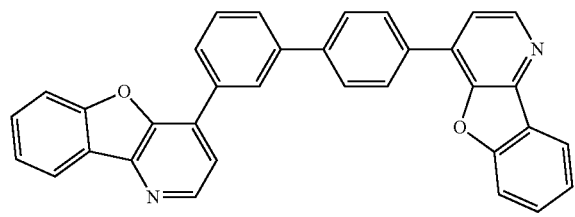
M-34
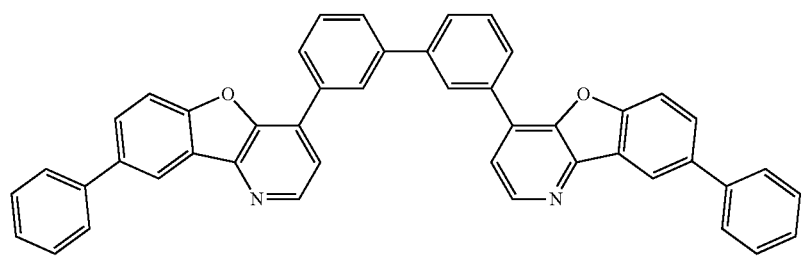
M-35
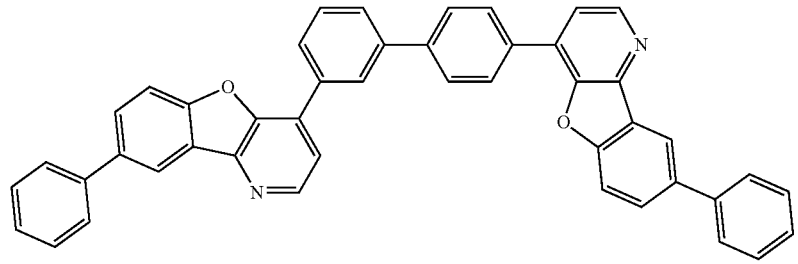

-continued
M-36
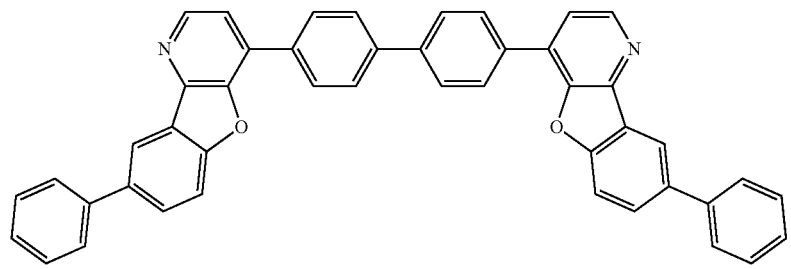
[Formula 22]
M-37
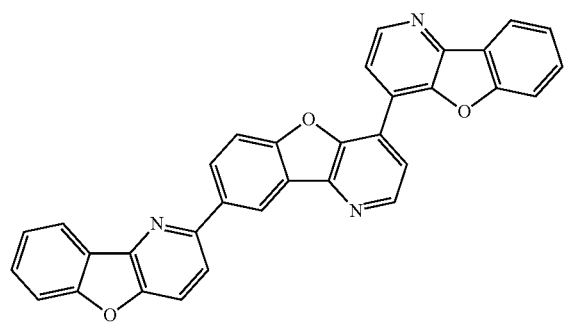
M-38
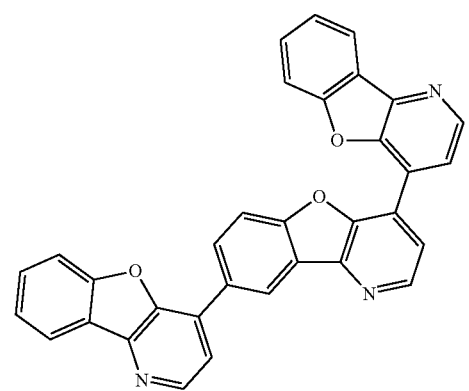
M-39
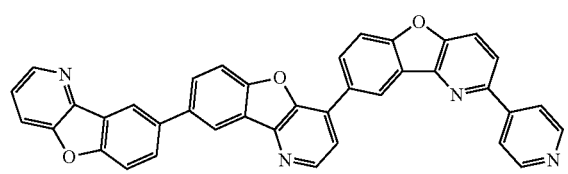
M-40
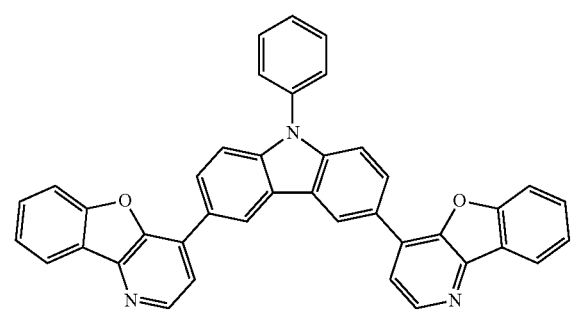
M-41
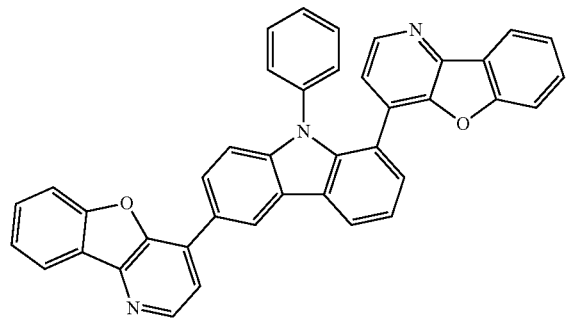
M-42
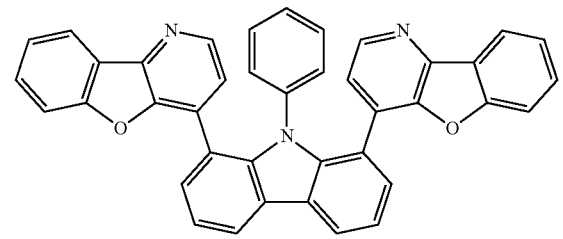

-continued
M-43
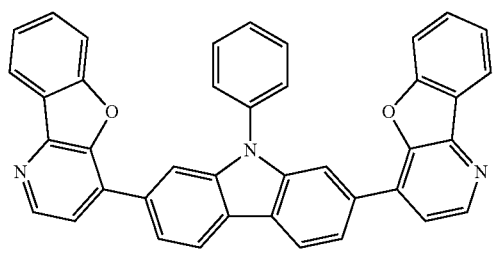
M-44
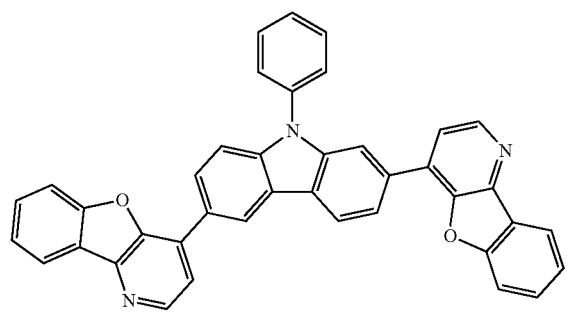
M-45
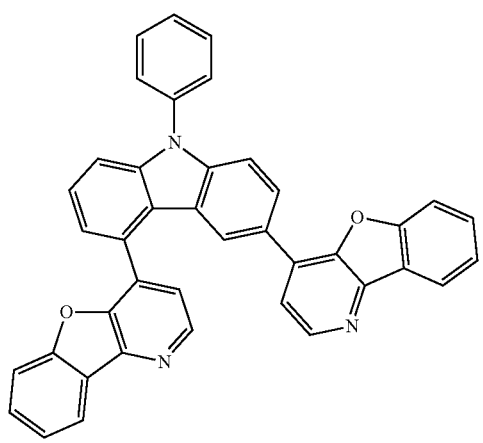
[Formula 23]
M-46
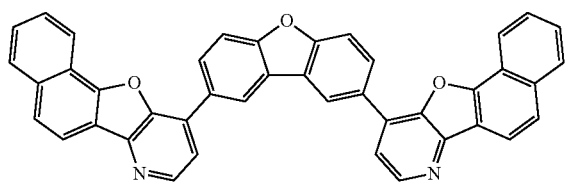
M-47
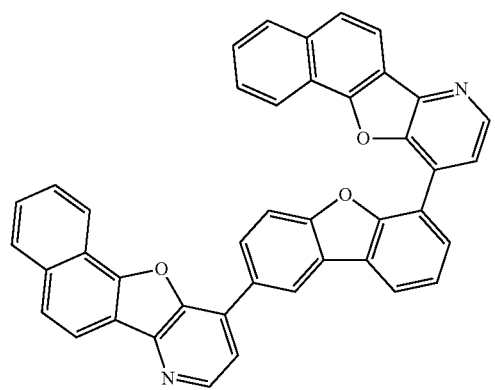
M-48
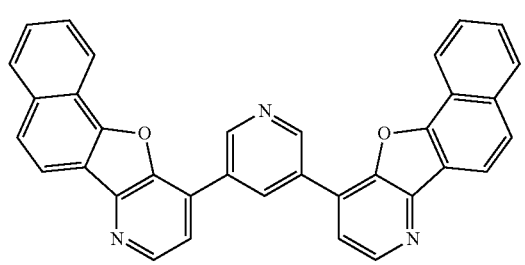
M-49
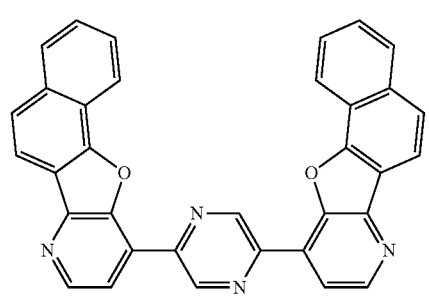

M-50 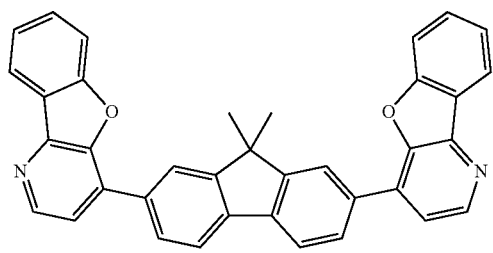
M-51 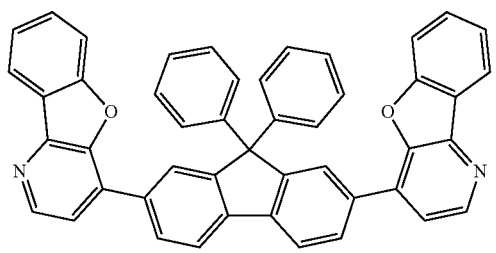
M-52 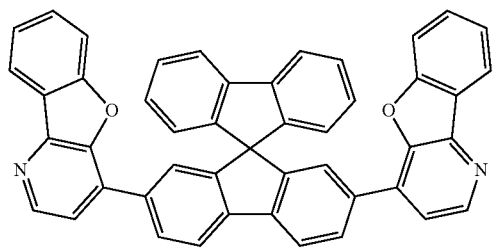
M-53 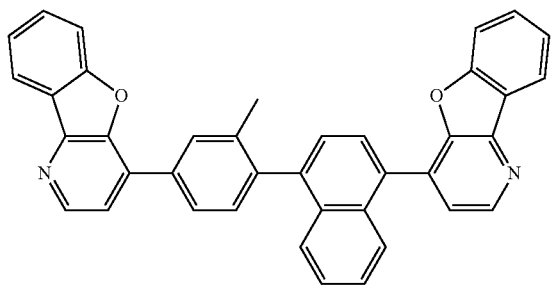
M-54 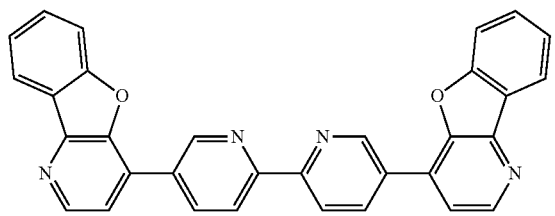
M-55 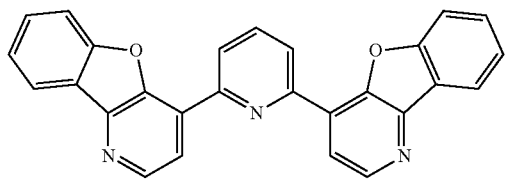
[Formula 24]
M-56 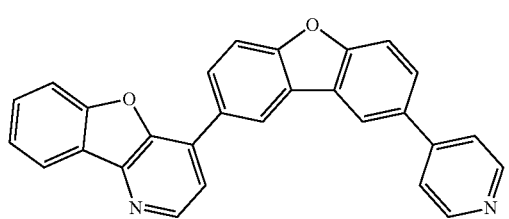
M-57 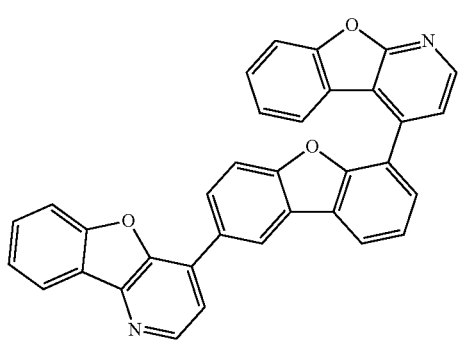
M-58 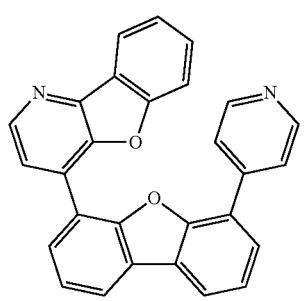
M-59 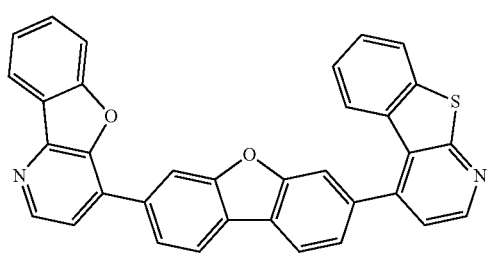

-continued
M-60
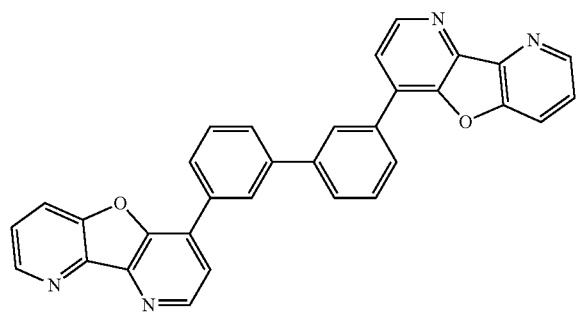
M-61
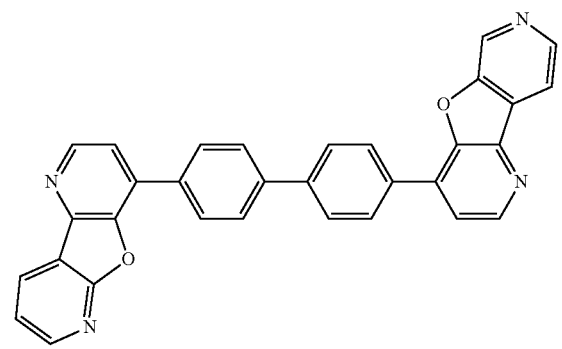
M-62
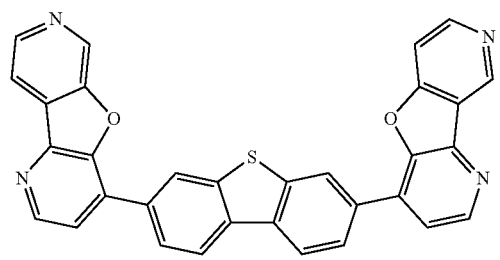
M-63
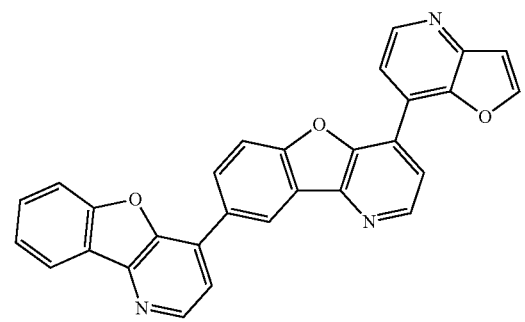
M-64
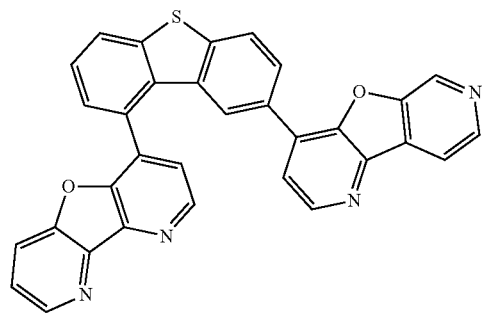
M-65
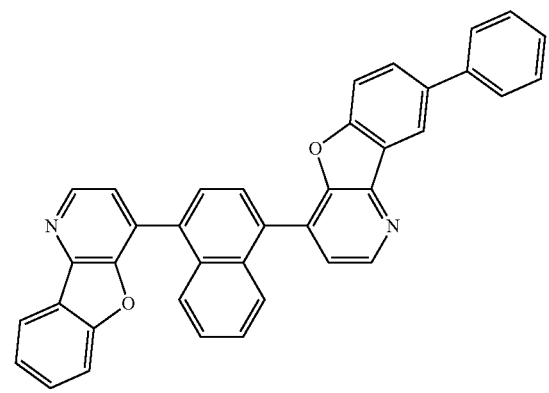
[Formula 25]
M-66
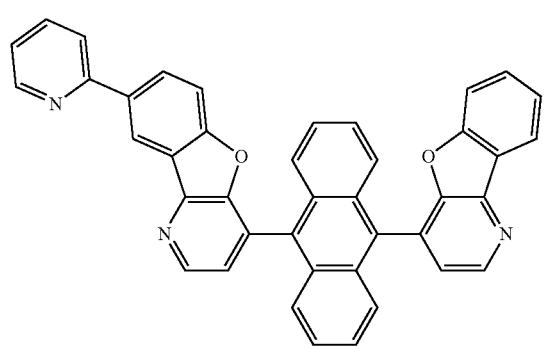
M-67
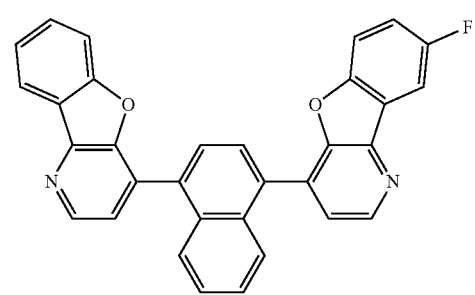

-continued
M-68
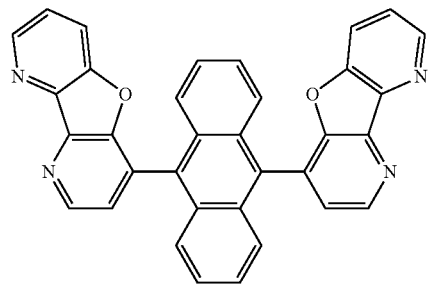
M-69
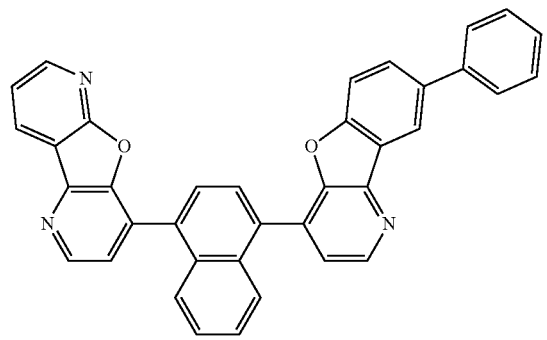
M-70
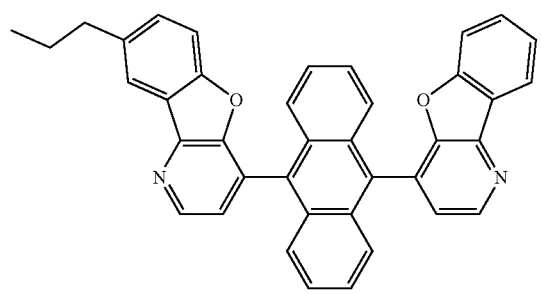
M-71
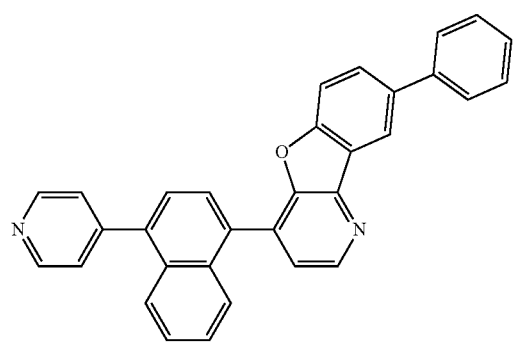
M-72
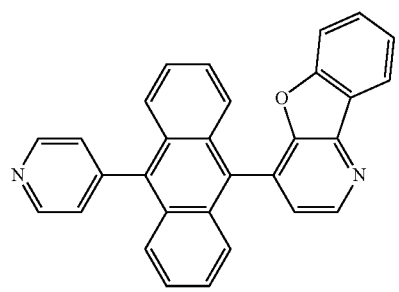
M-73
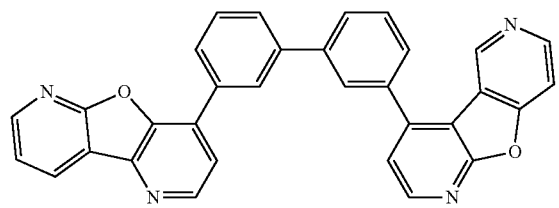
M-74
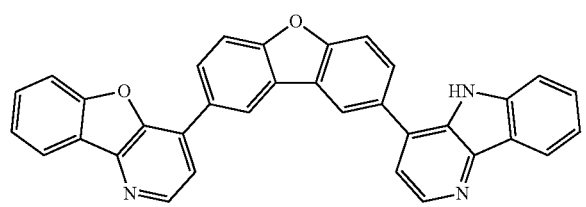
M-75
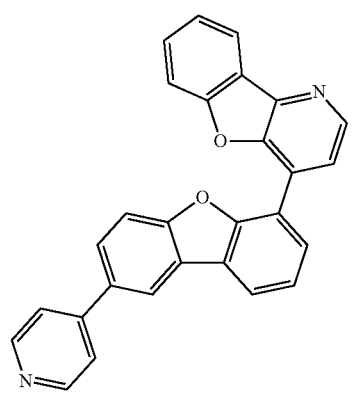

[Formula 26]
M-76
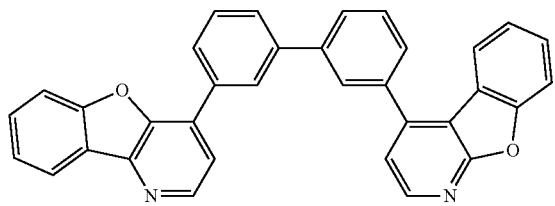
M-77
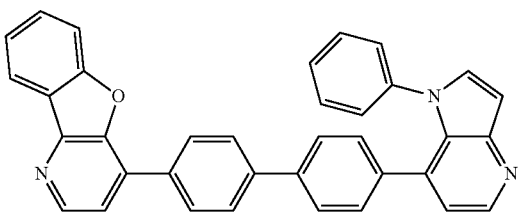
M-78
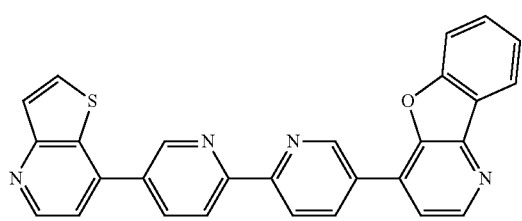
M-79
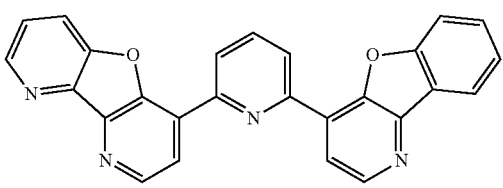
M-80
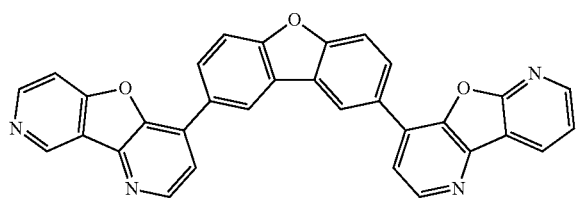
M-81
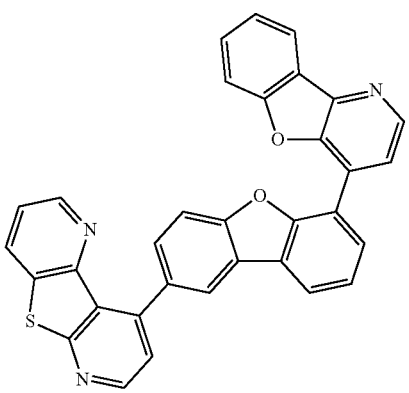
M-82
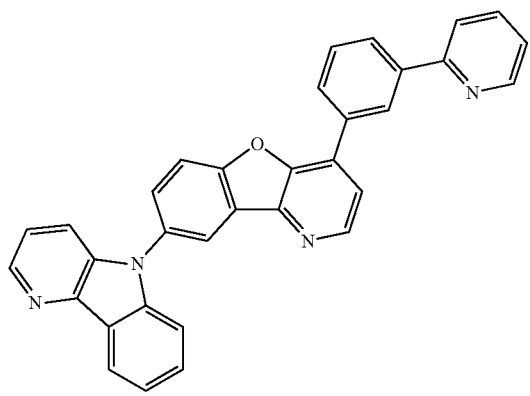
M-83
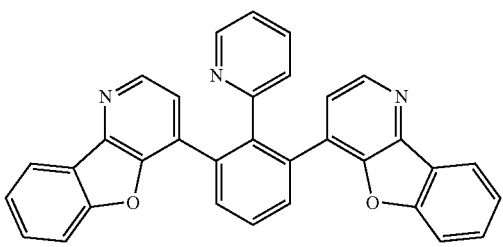
M-84
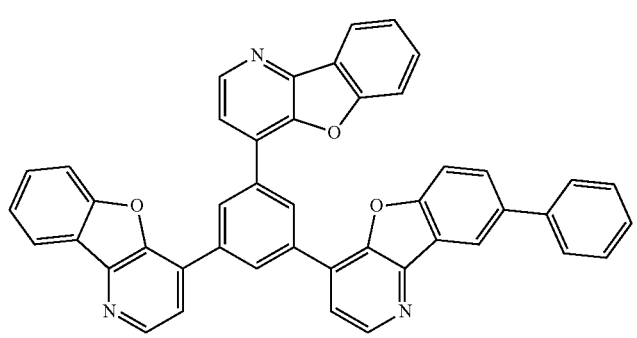

[Formula 27]
-continued
M-85
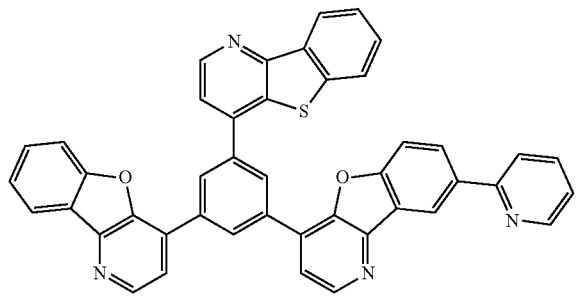
M-86
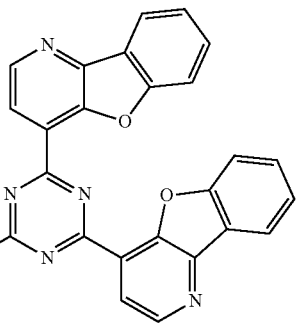
M-87
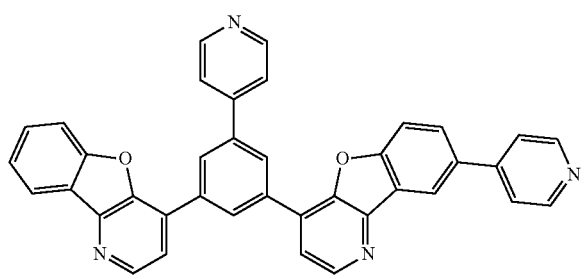
M-88
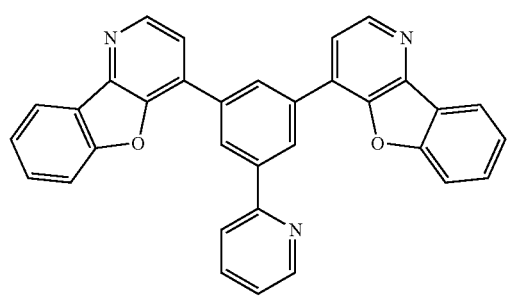
M-89
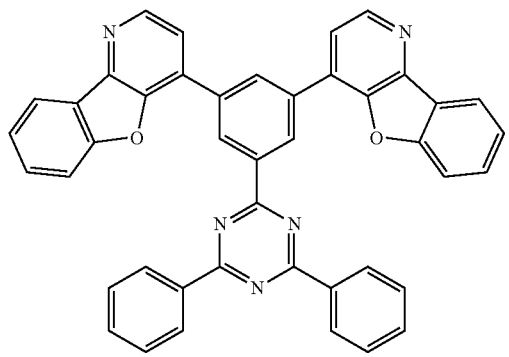
M-90
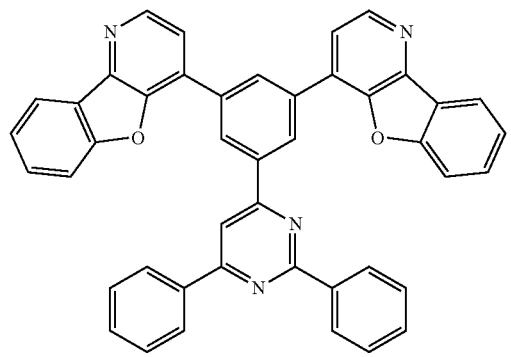
M-91
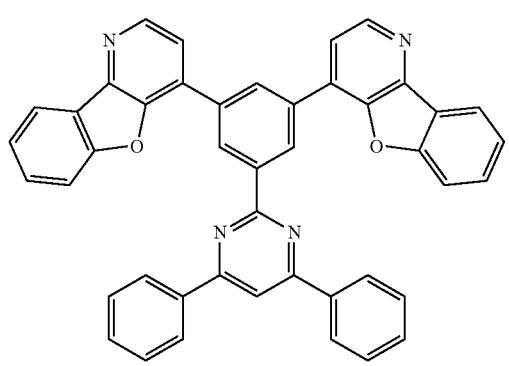

-continued
[Formula 28]
M-101
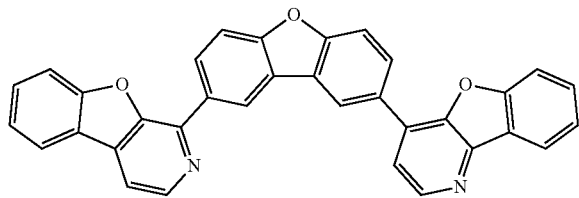
M-102
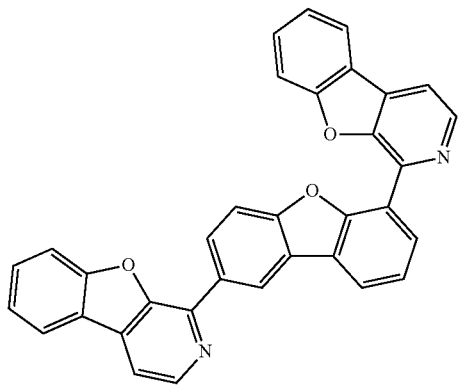
M-103
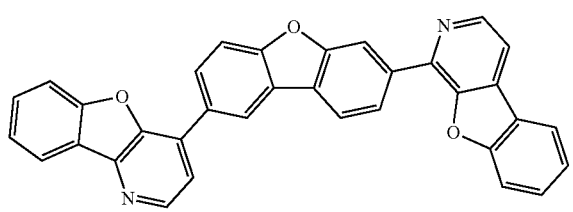
M-104
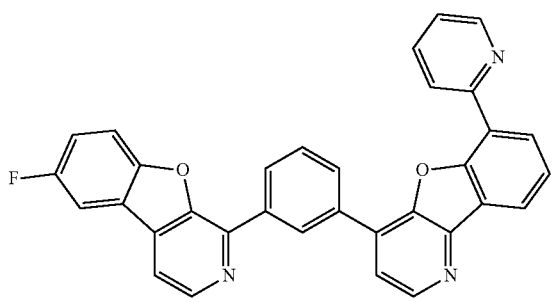
M-105
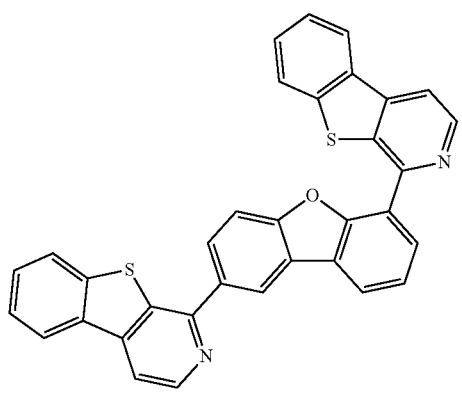
M-106
M-107
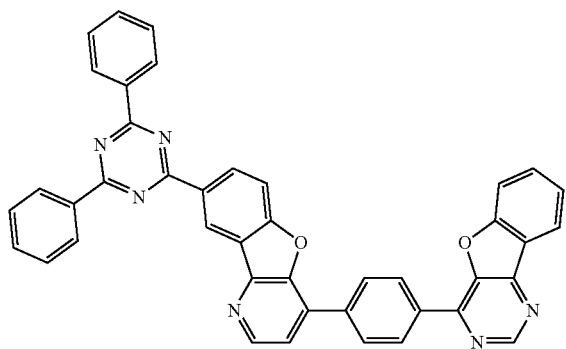
M-108
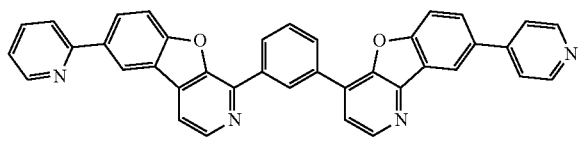

-continued
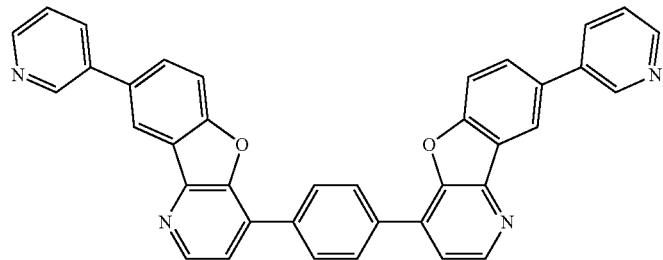
M-109
[Formula 29]
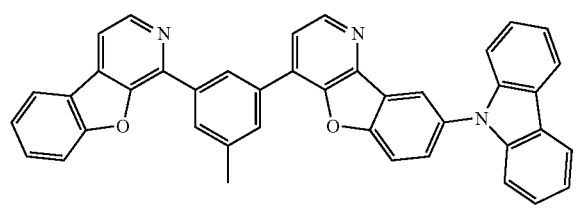
M-110    M-111
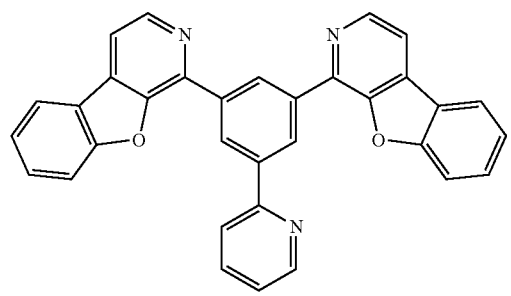
M-112
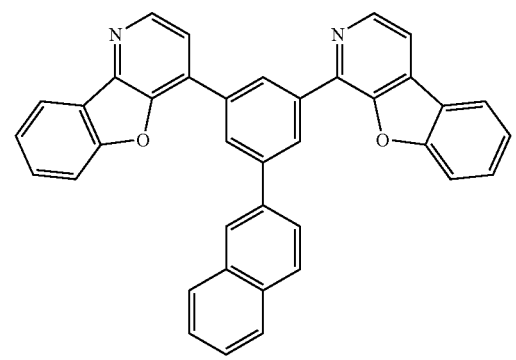
M-113
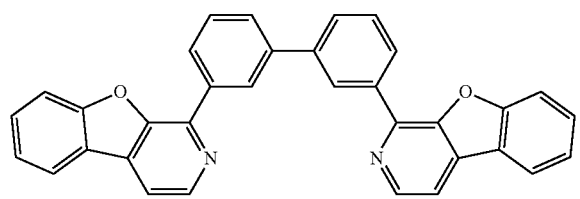
M-114
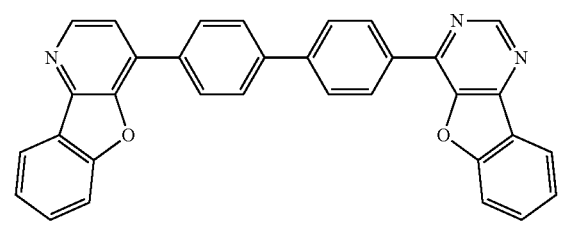
M-115
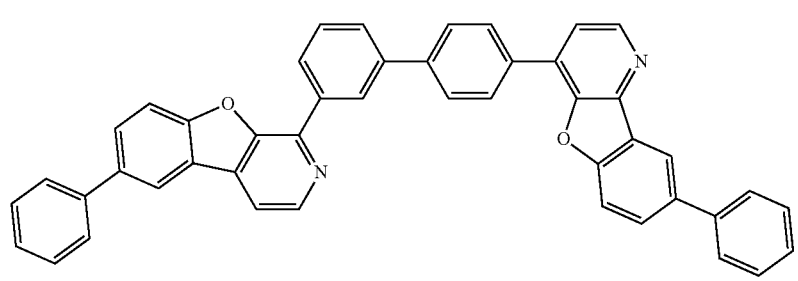
M-116

-continued
[Formula 30]
M-117
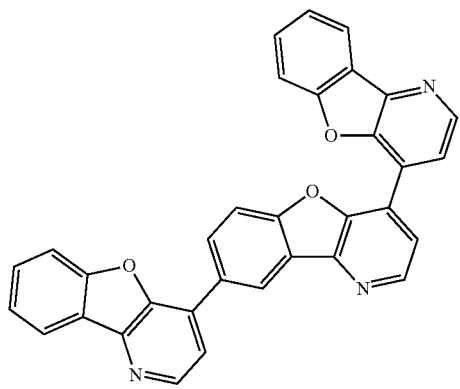
M-118
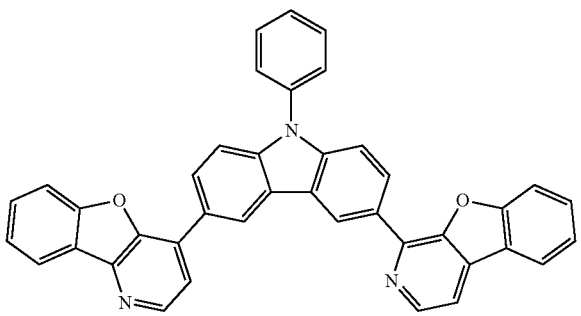
M-119
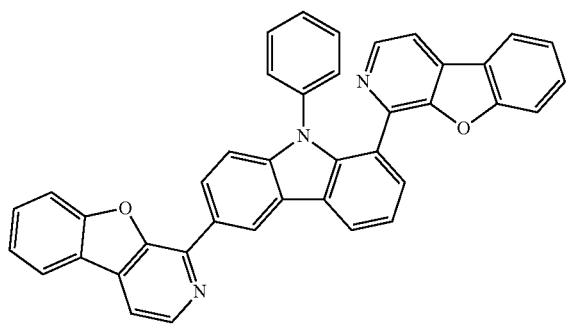
M-120
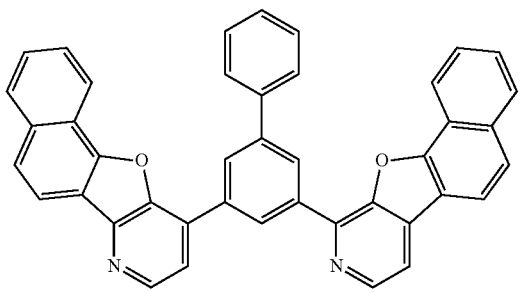
M-121
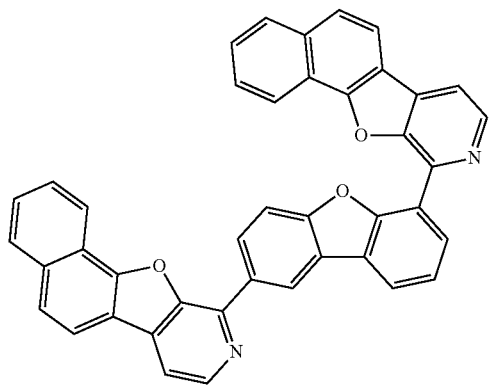
M-122
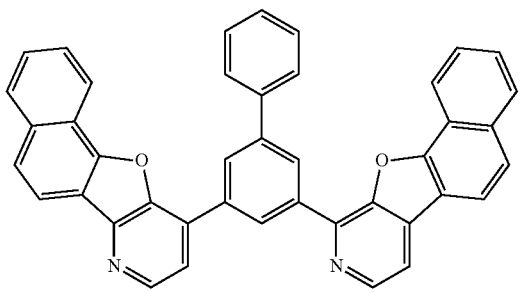
[Formula 31]
M-123
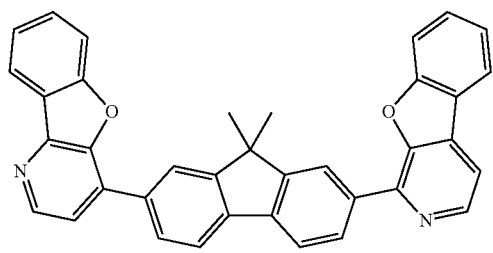
M-124
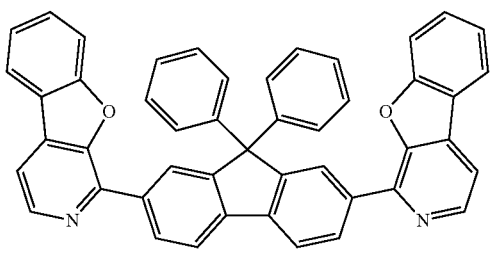

-continued
M-125 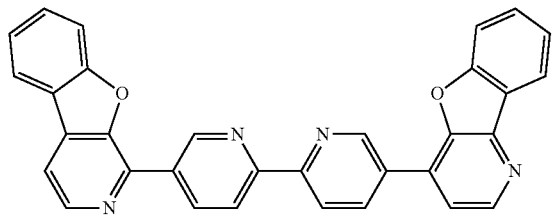
M-126 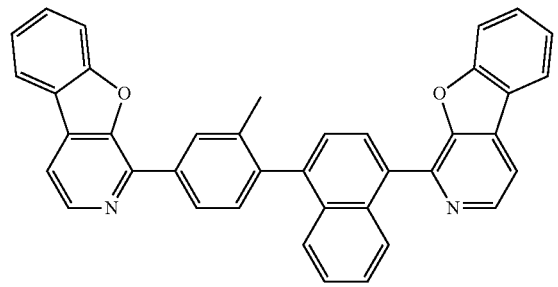
M-127 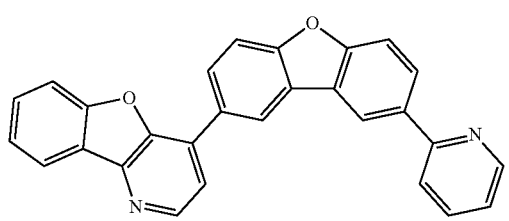
M-128 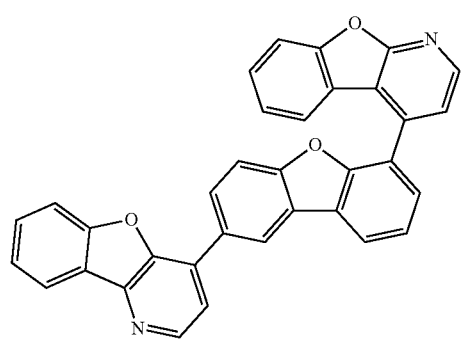
M-129 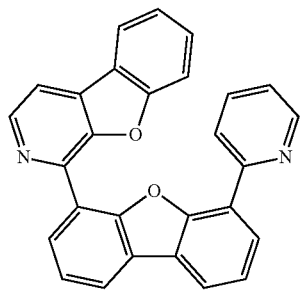
M-130 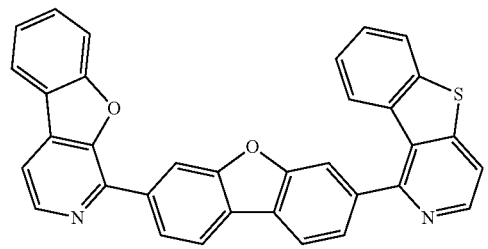
M-131 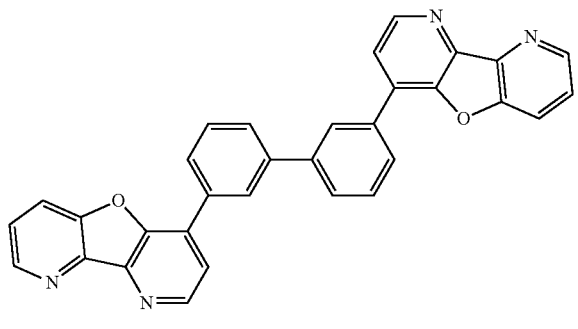
M-132 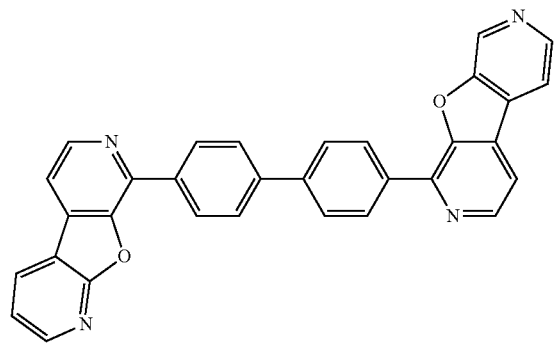

[Formula 32]
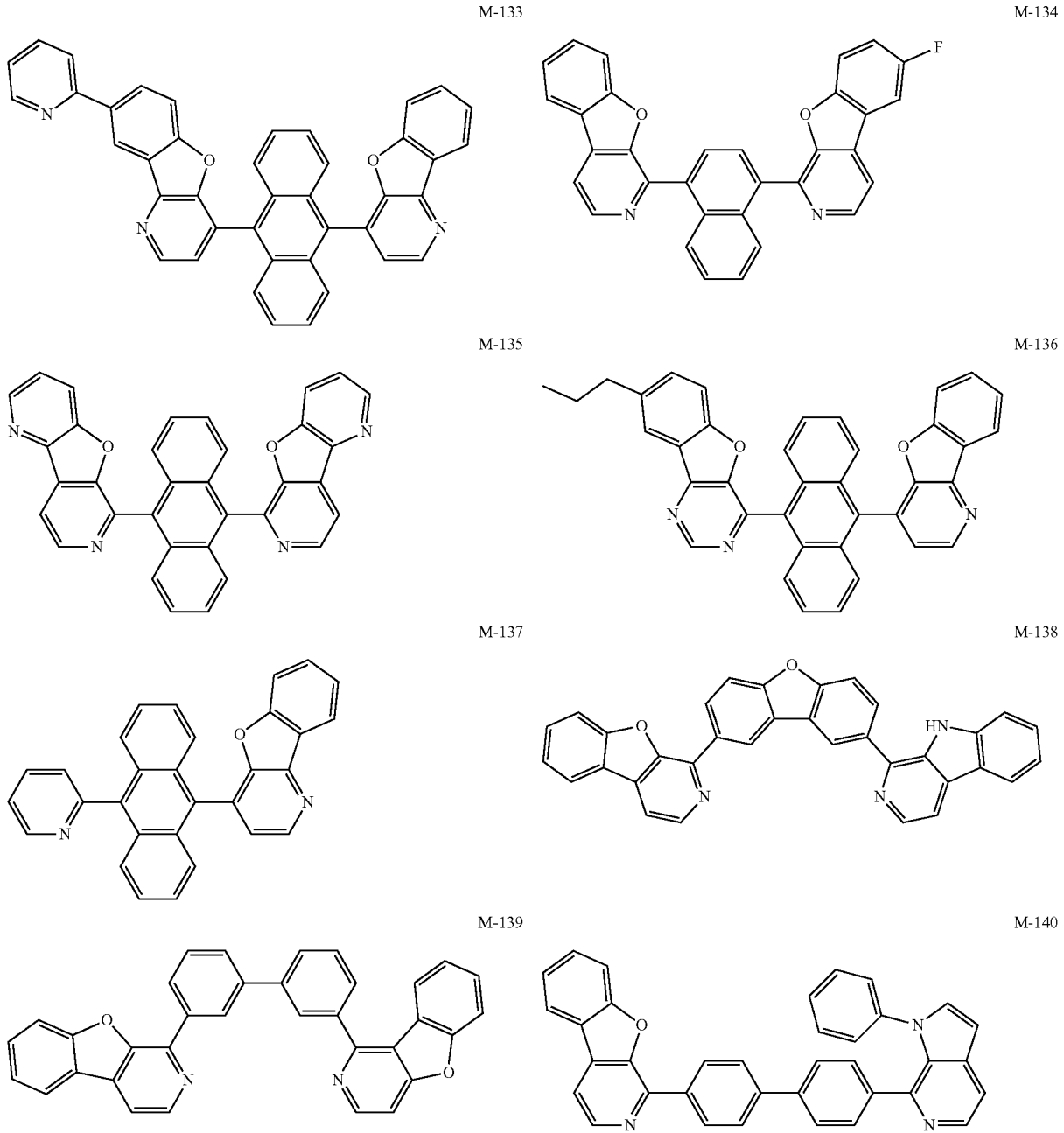
[Formula 33]
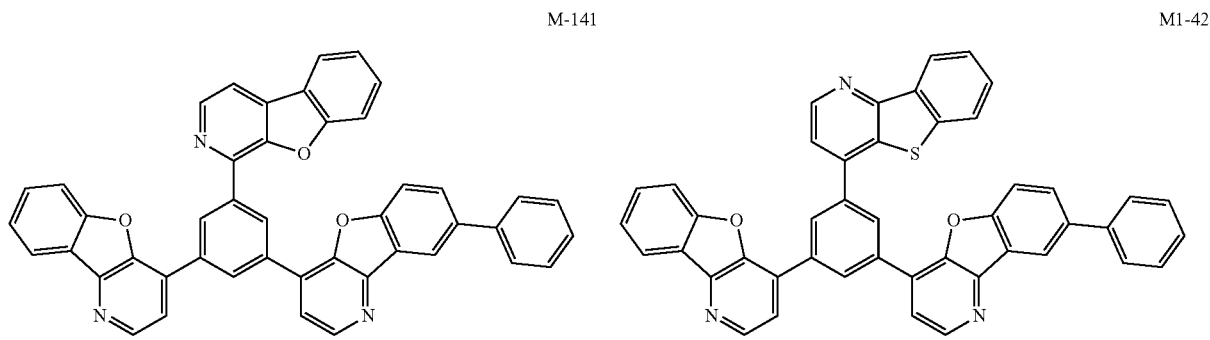

-continued
M-143
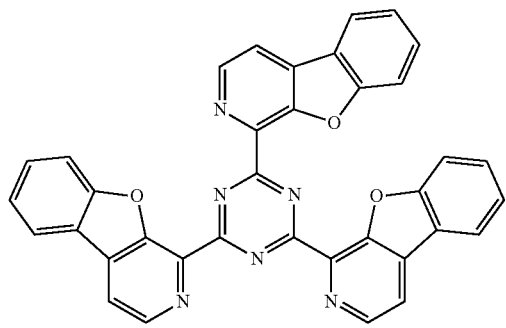
[Formula 34]
M-144
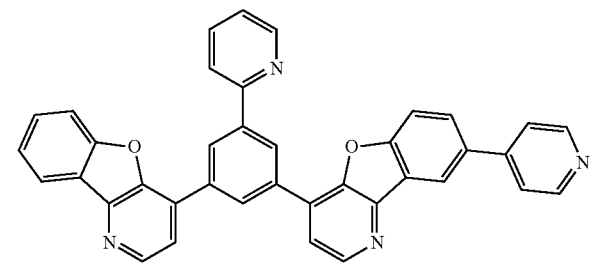
M-145
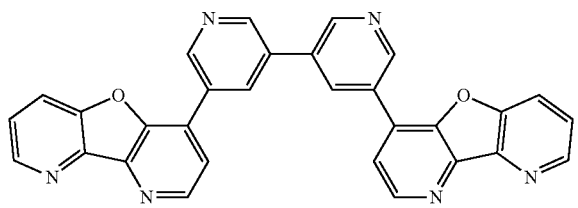
M-146
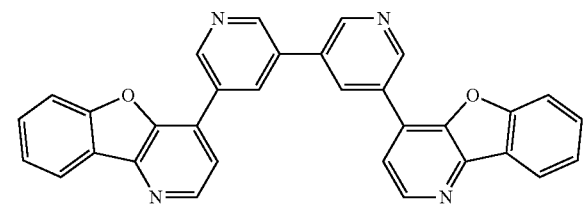
M-147
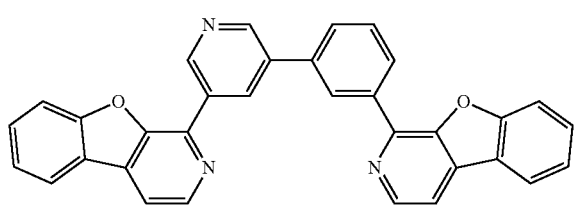
M-148
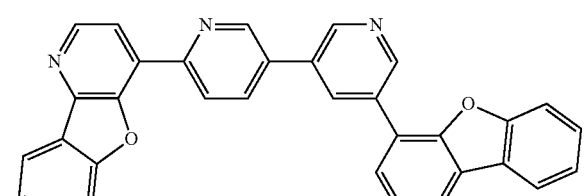
M-149
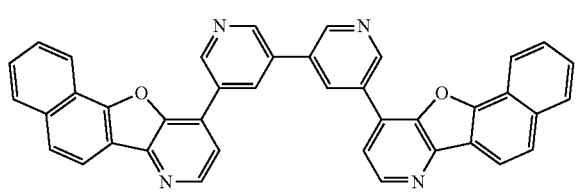
M-150
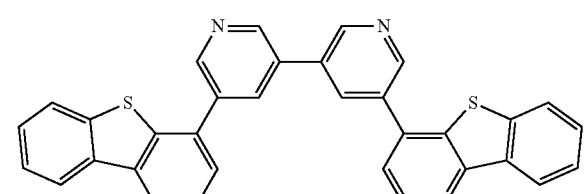
M-151
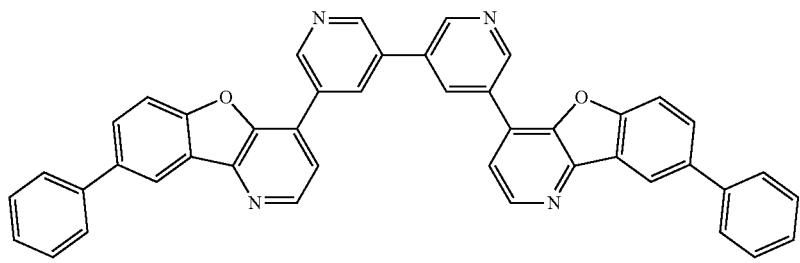
M-152
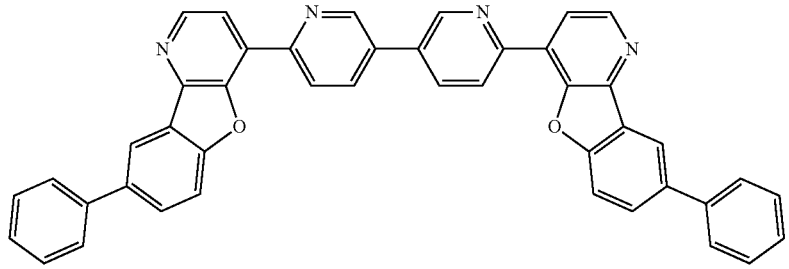

[Formula 35]
M-153
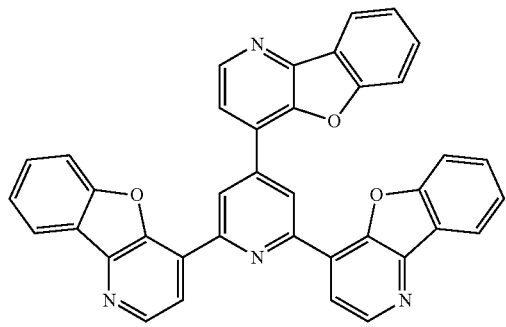
M-154
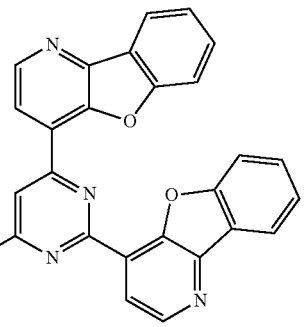
M-155
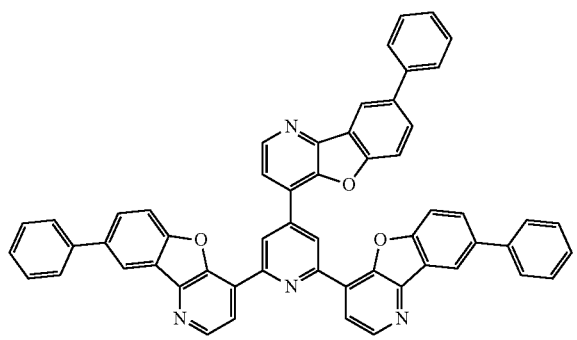
M-156
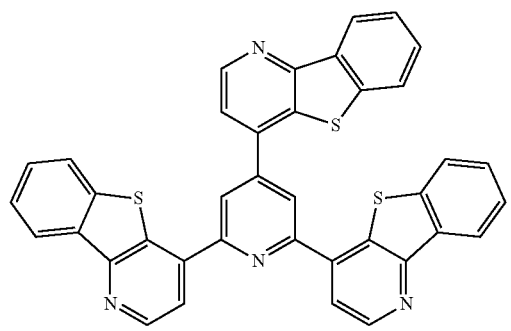
M-157
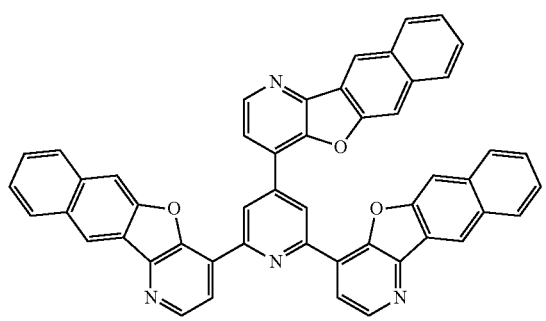
M-158
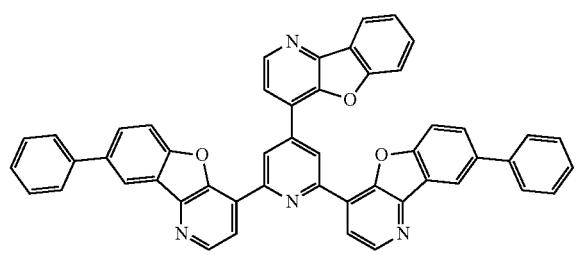
[Formula 36]
M-159
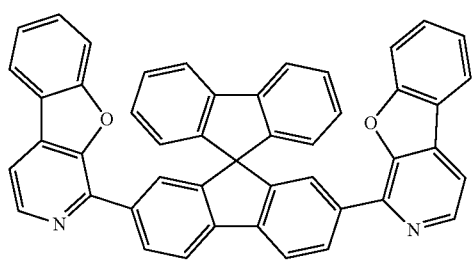
M-160
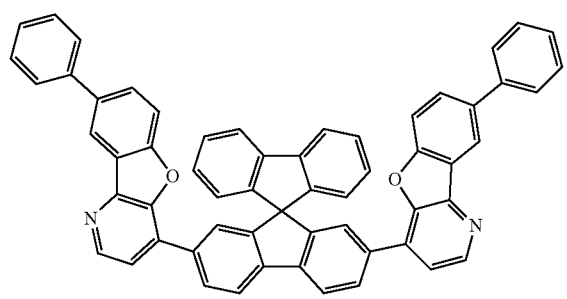

M-161
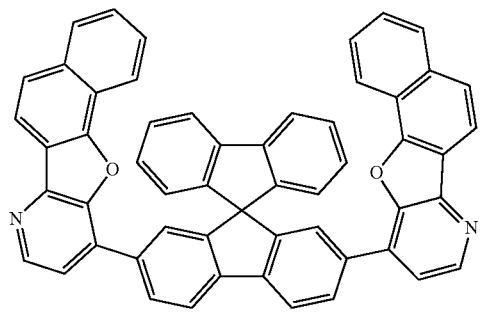
M-162
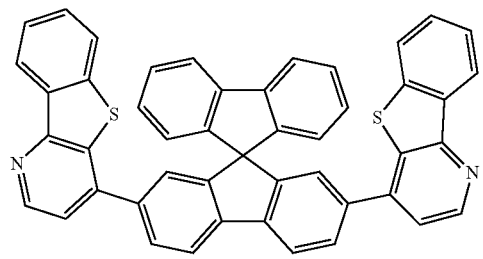
M-163
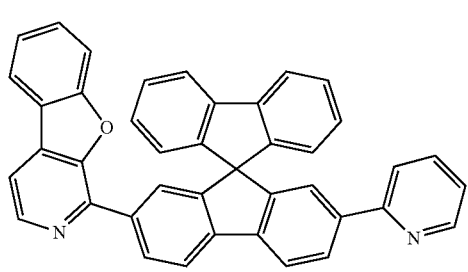
M-164
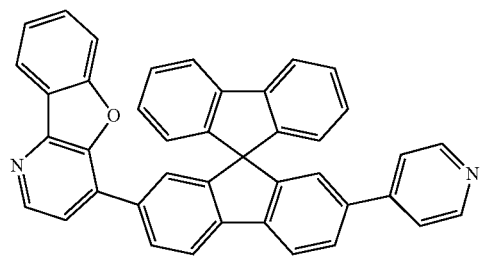
M-165
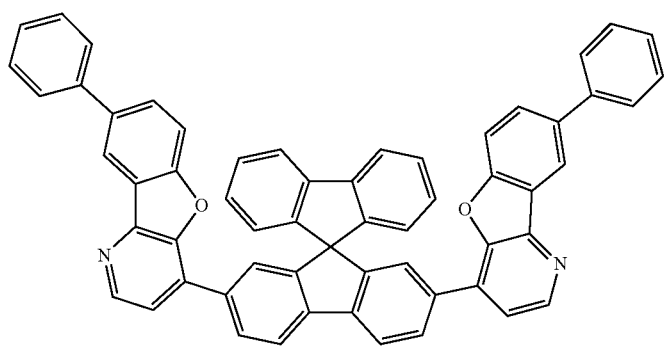
[Formula 37]
M-166
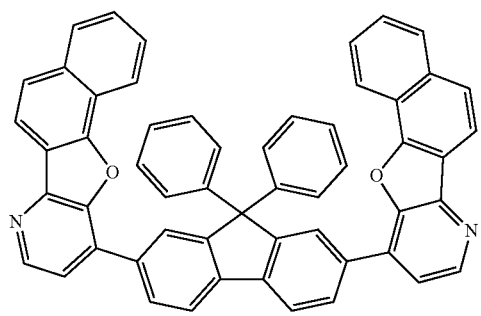
M-167
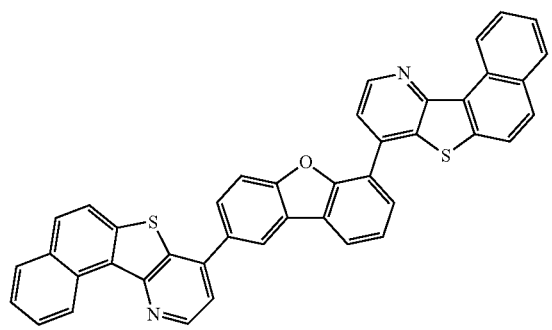
M-168
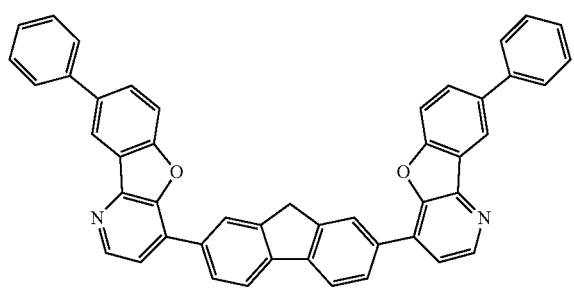
M-169
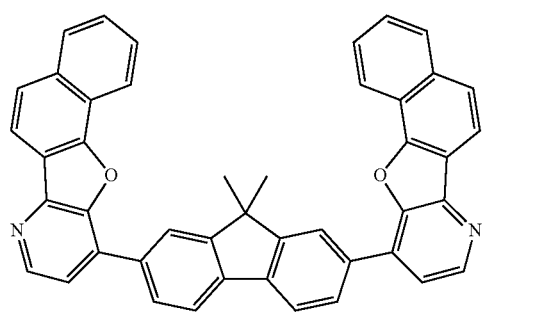

-continued
M-170
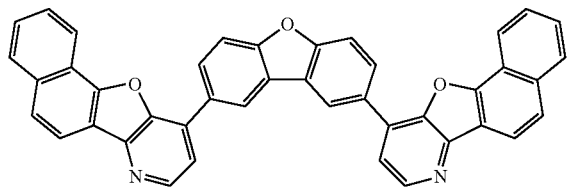
[Formula 38]
M-171
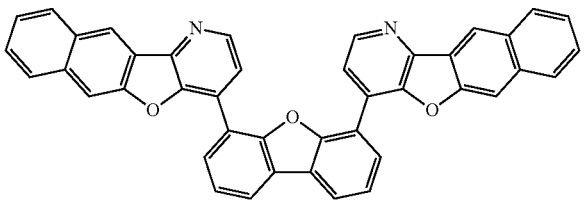
M-172
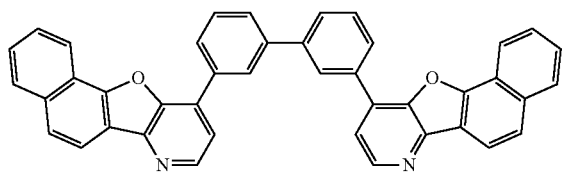
M-173
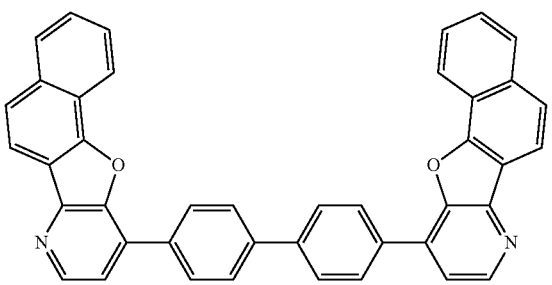
M-174
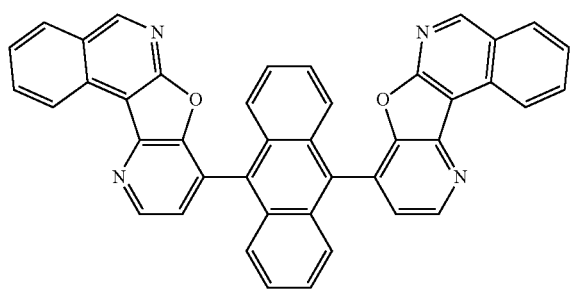
M-175
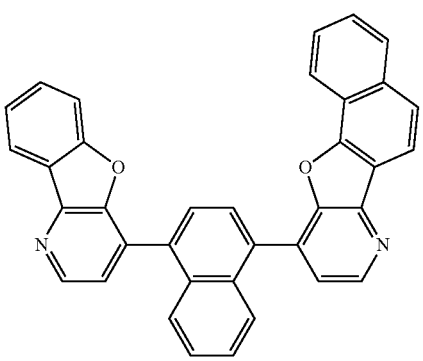
M-176
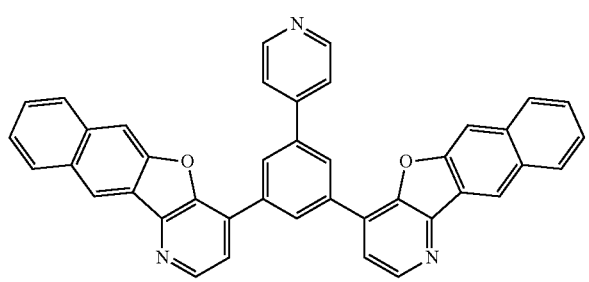
M-177
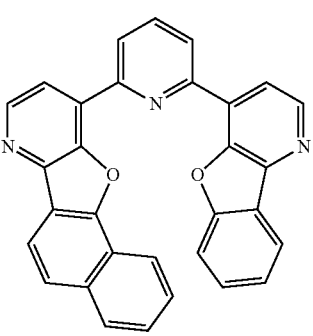
M-178
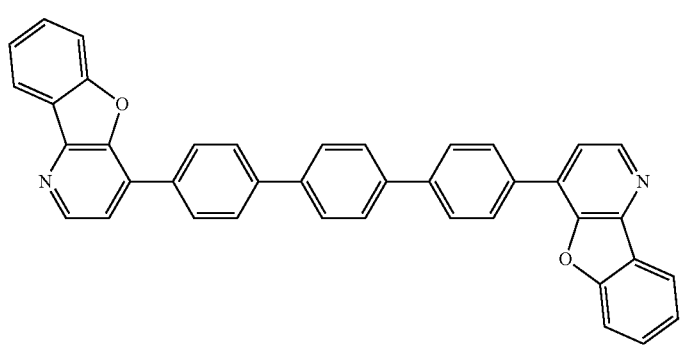

M-179
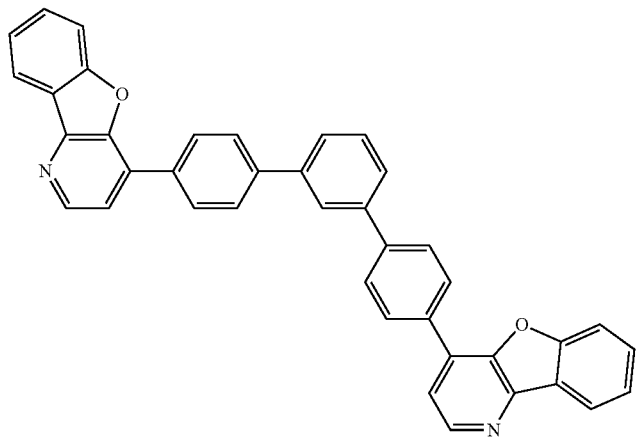
[Formula 39]
M-180
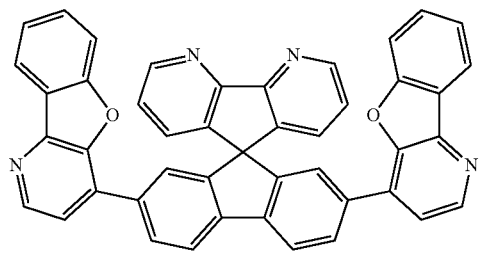
M-181
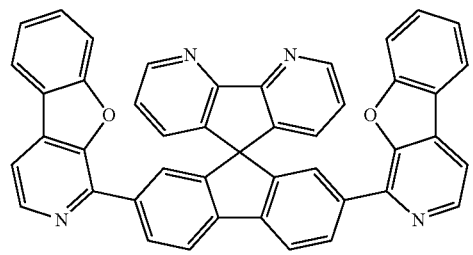
M-182
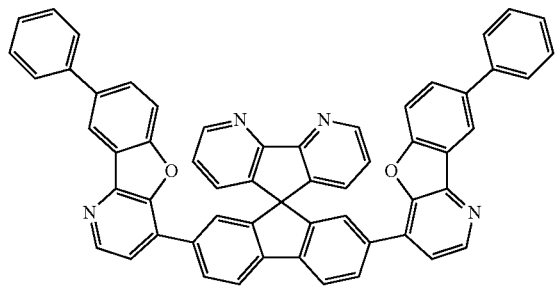
M-183
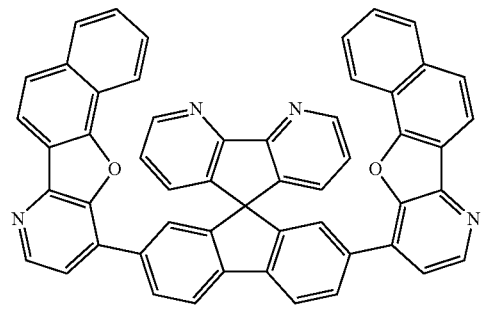
M-184
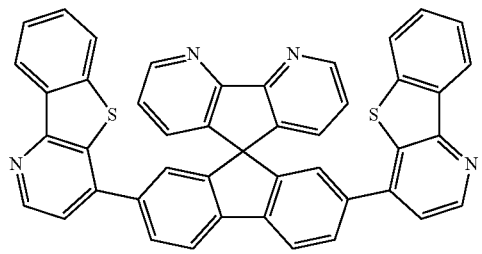
M-185
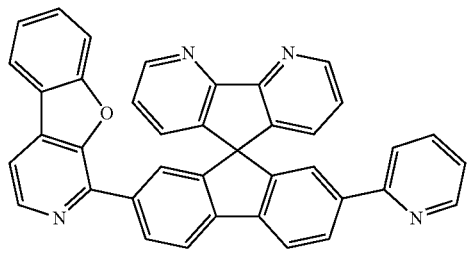
M-186
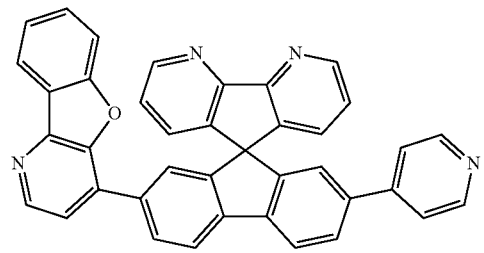

[Formula 40]
M-187
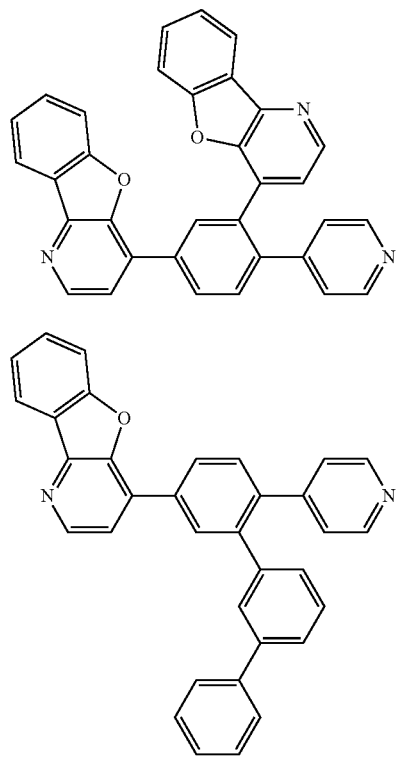
M-188
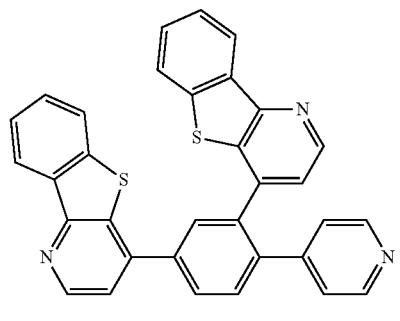
M-189
M-190
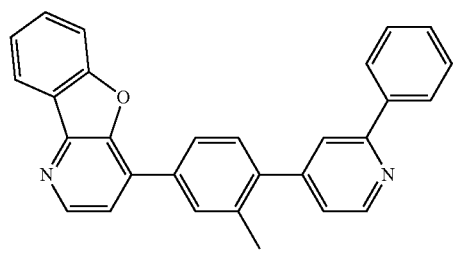
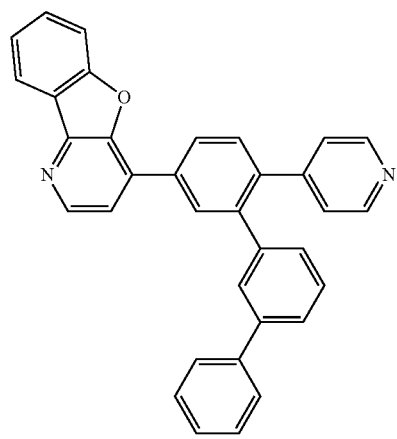
M-191
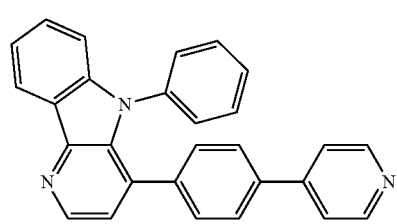
M-192
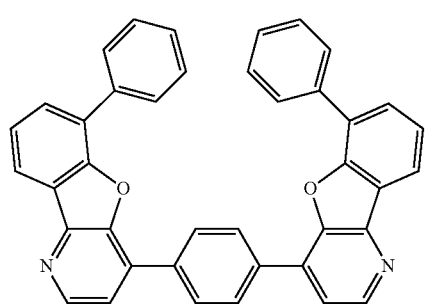
M-193
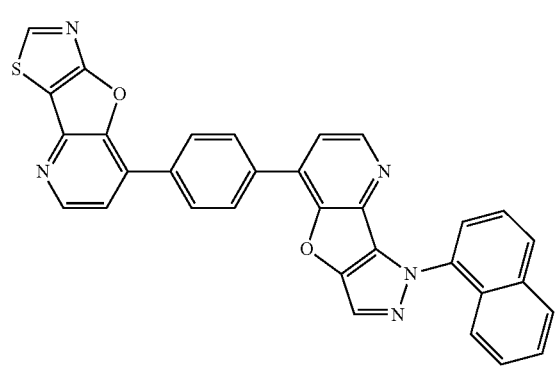
M-194
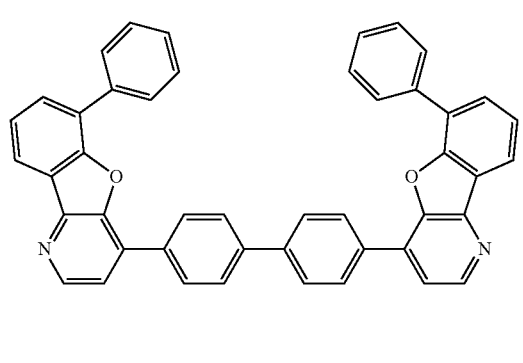

M-195
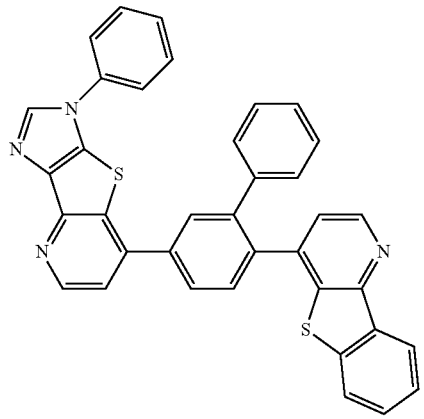
[Formula 41]
M-196
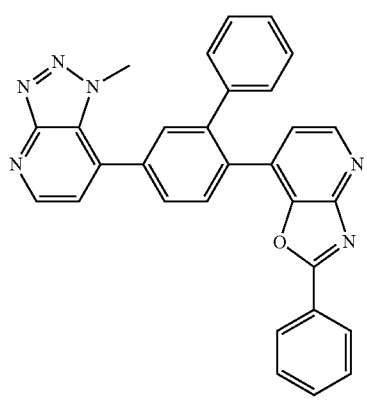
M-197
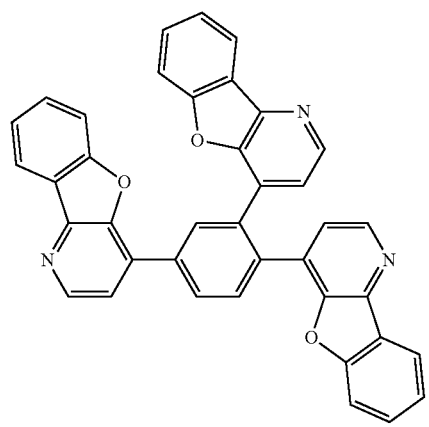
M-198
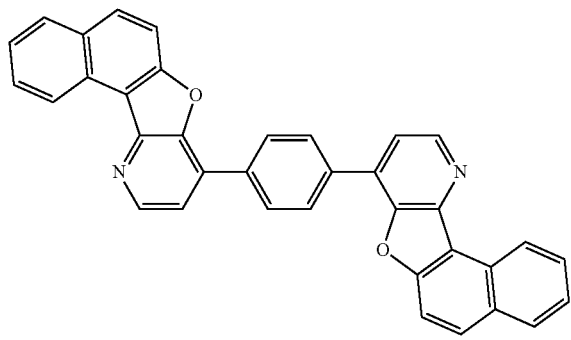
M-199
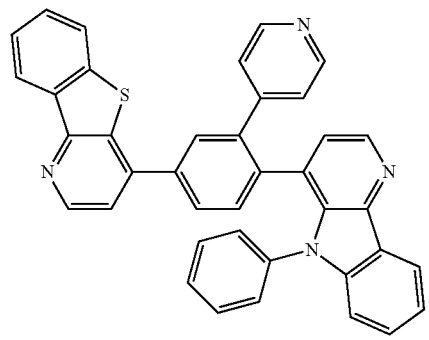
M-200
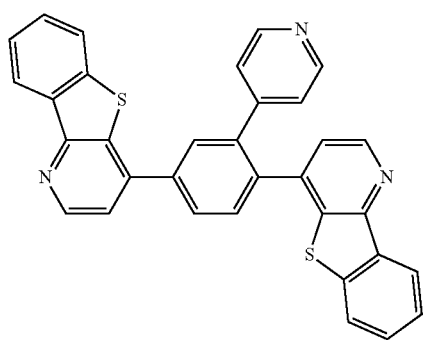
M-201
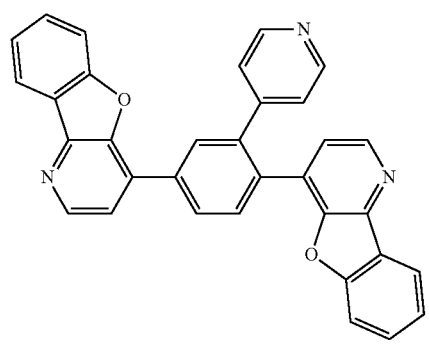

-continued
M-202
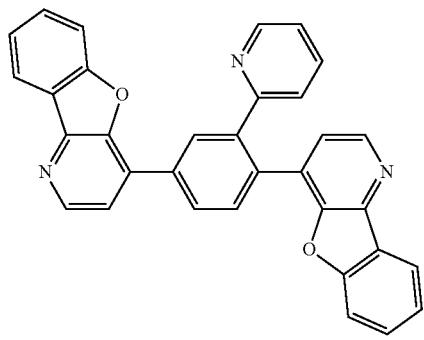
M-203
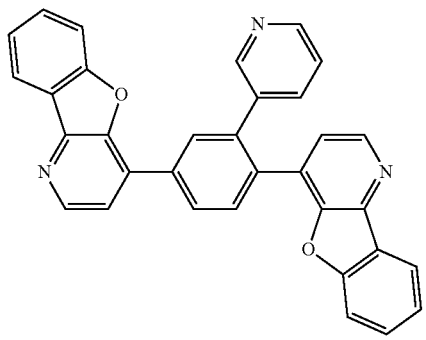
[Formula 42]
M-204
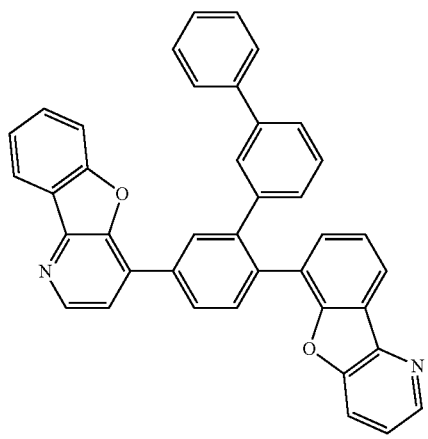
M-205
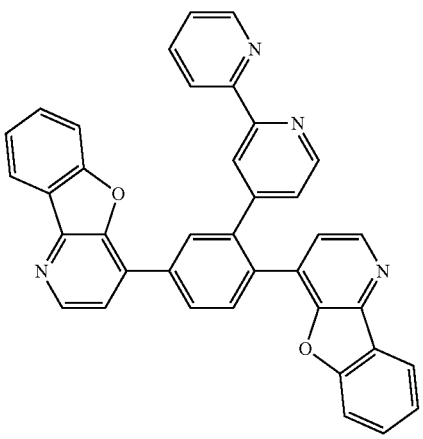
M-206
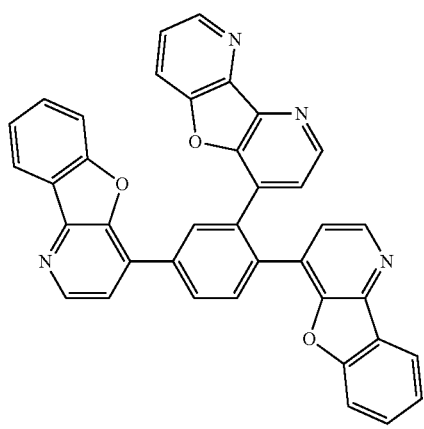
M-207
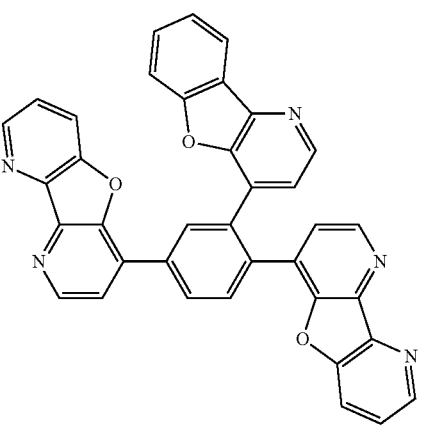
M-208
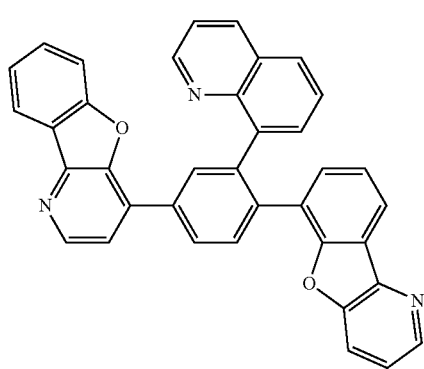
M-209
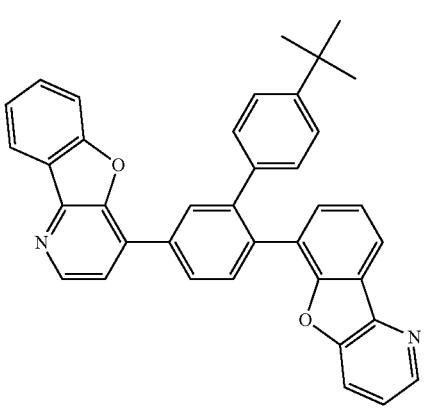

M-210
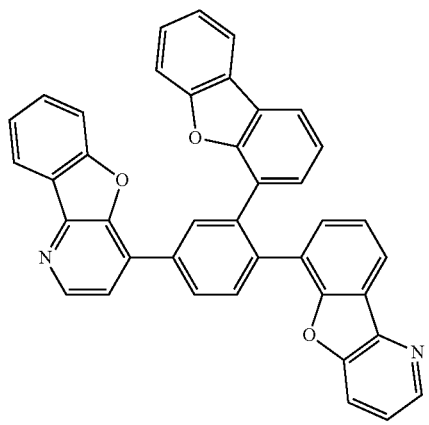
M-211
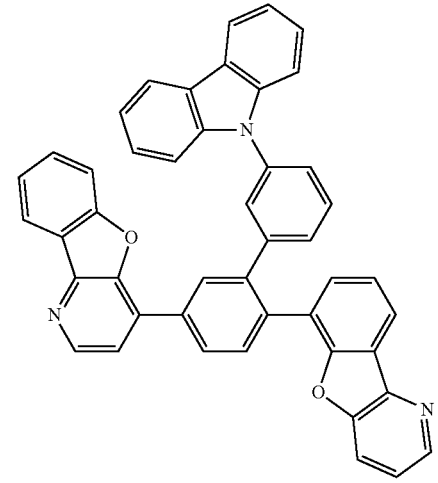
[Formula 43]
M-212
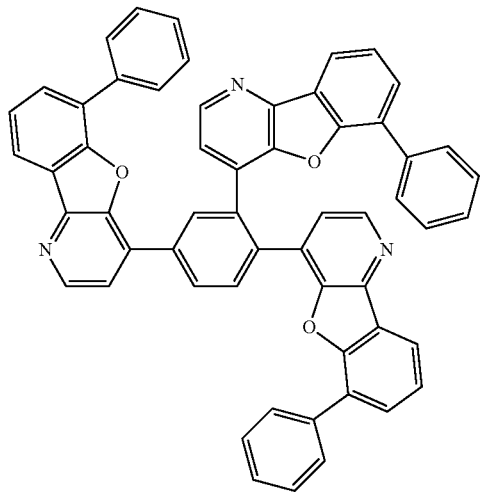
M-213
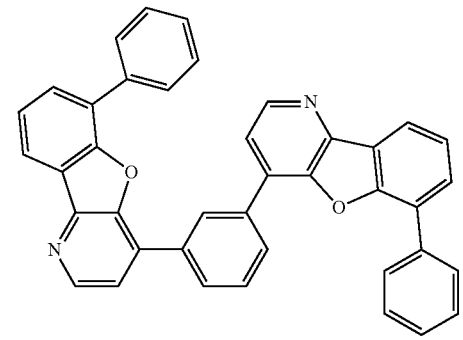
M-214
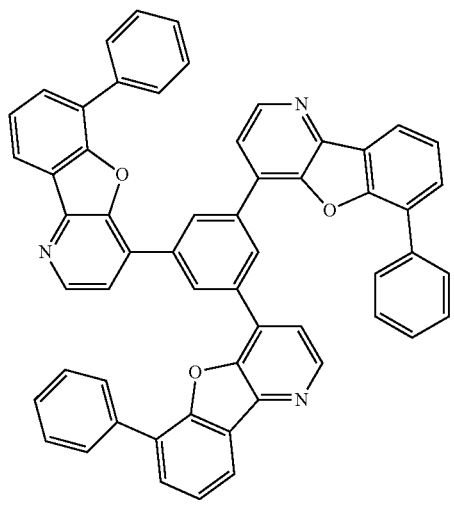
M-215
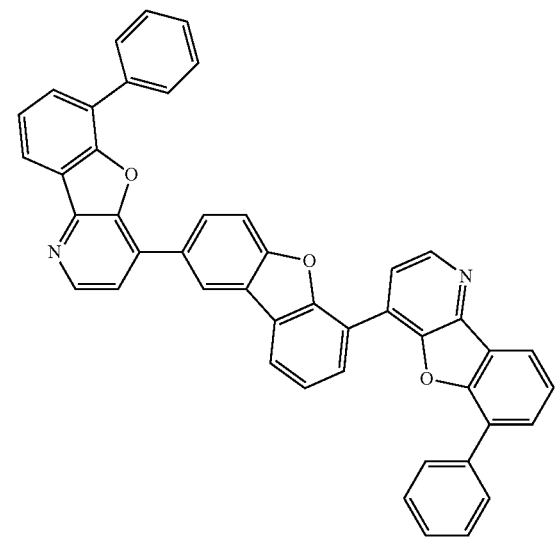

-continued
M-216
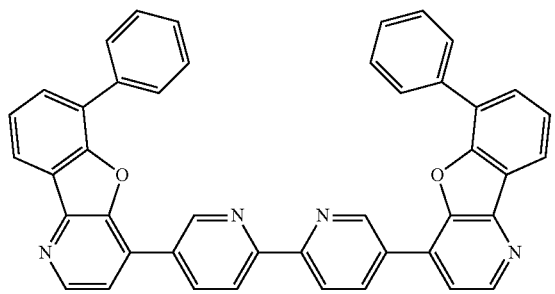
M-217
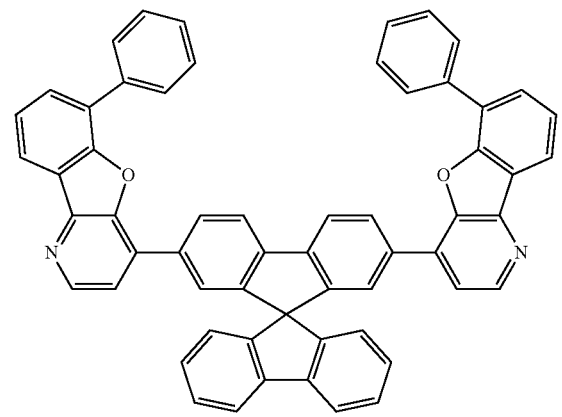
[Formula 44]
M-218
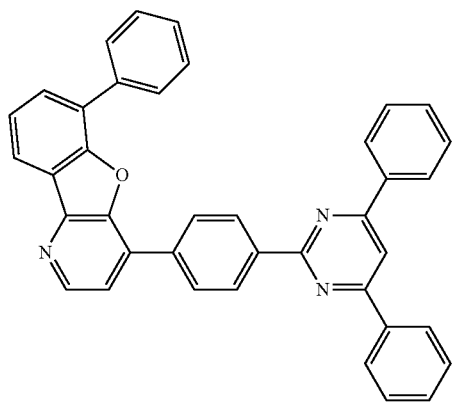
M-219
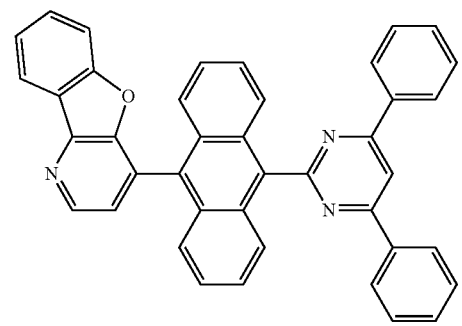
M-220
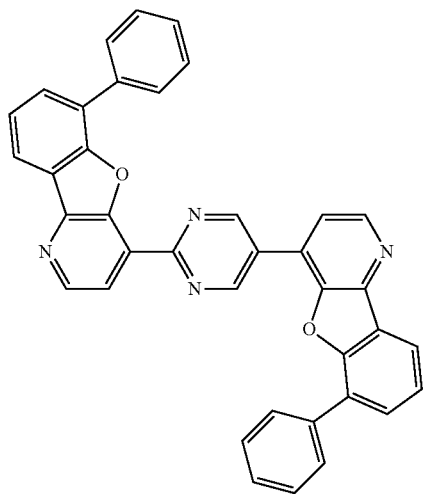
M-221
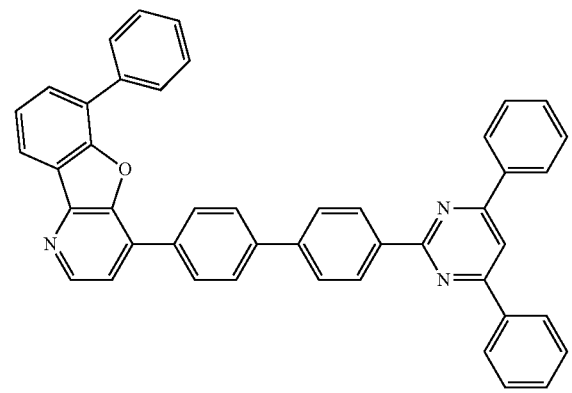

-continued
M-222
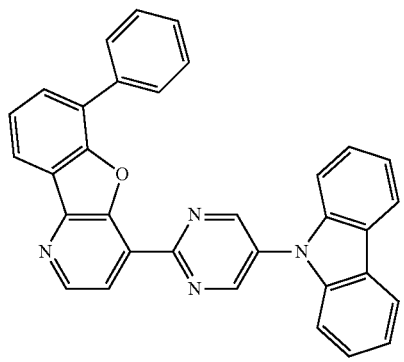
M-223
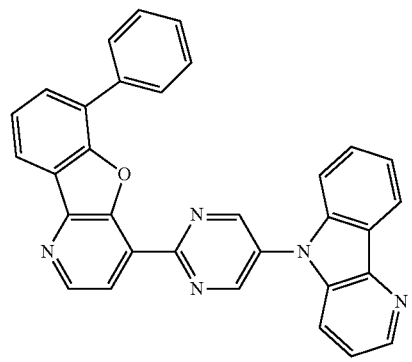
M-224
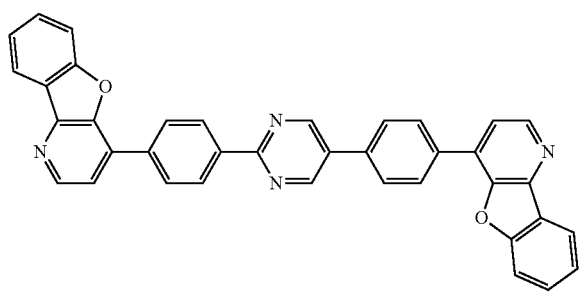
M-225
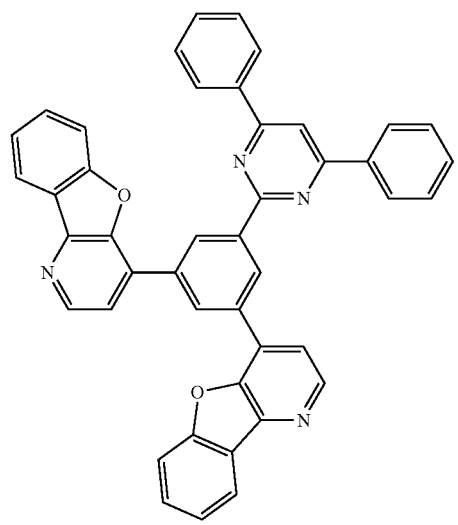
[Formula 45]
M-226
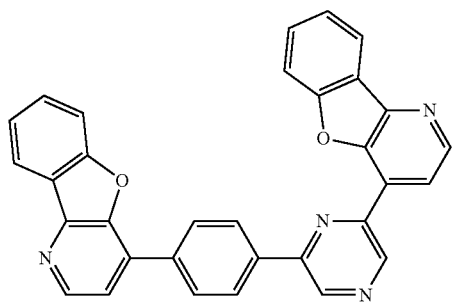
M-227
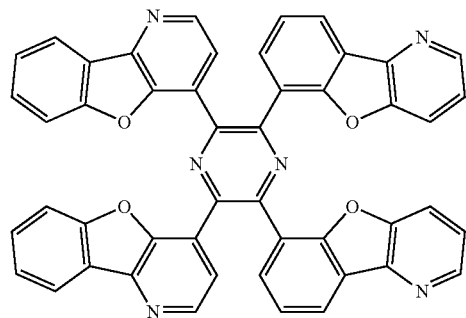

-continued
M-228
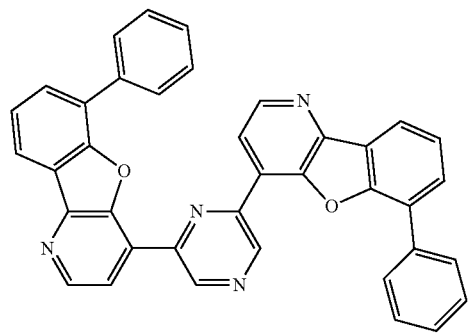
M-229
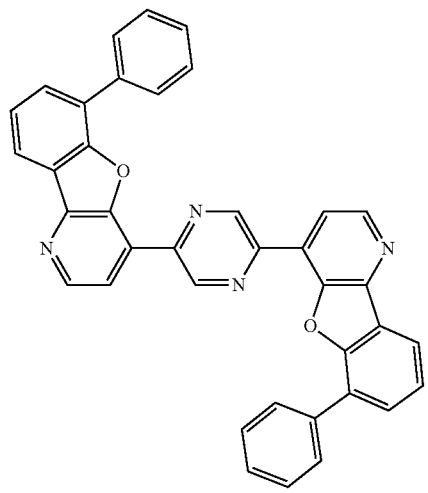
M-230
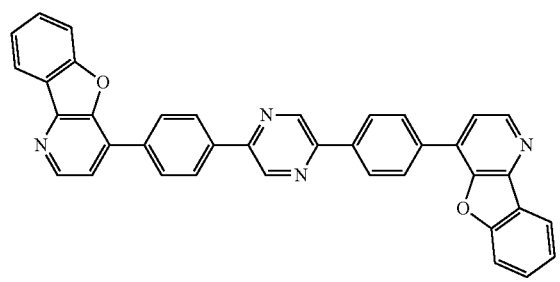
M-231
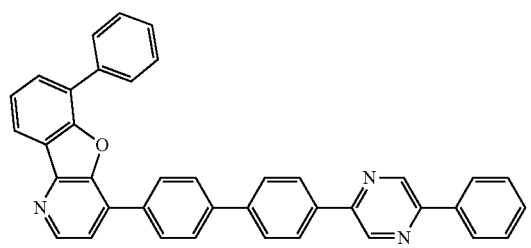
M-232
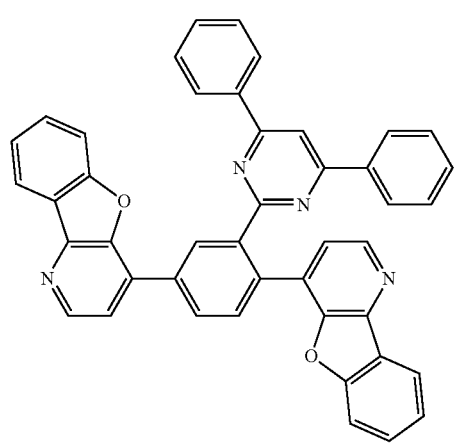
M-233
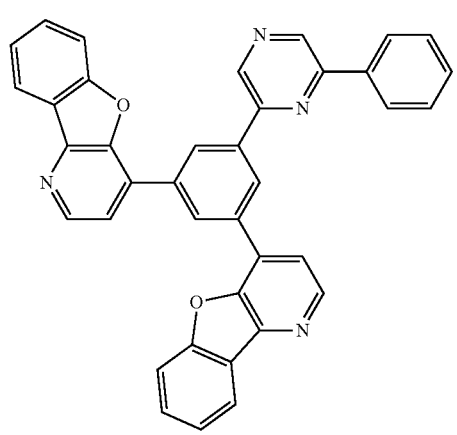

[Formula 46]
M-234
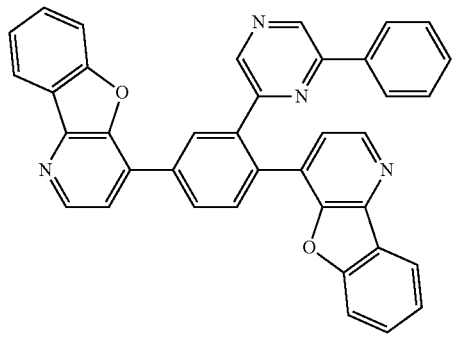
M-235
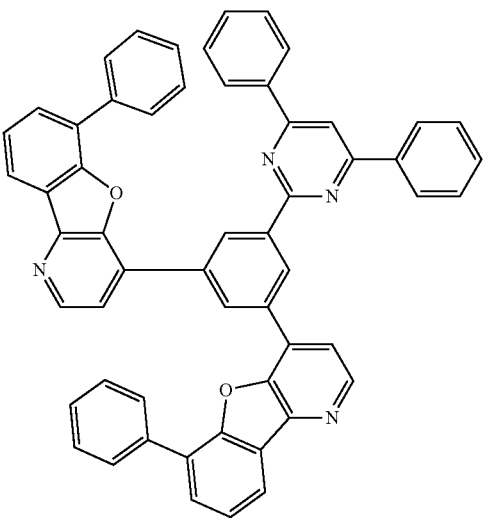
M-236
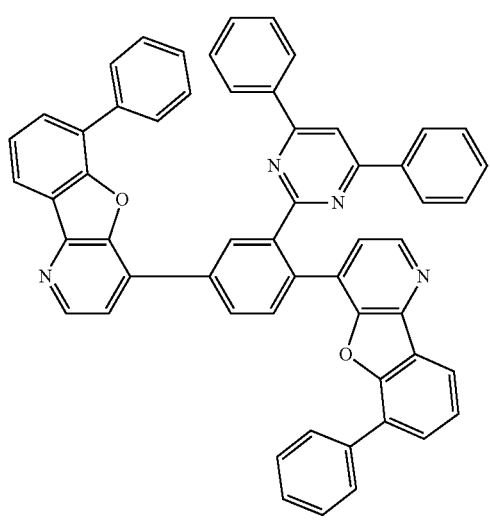
M-237
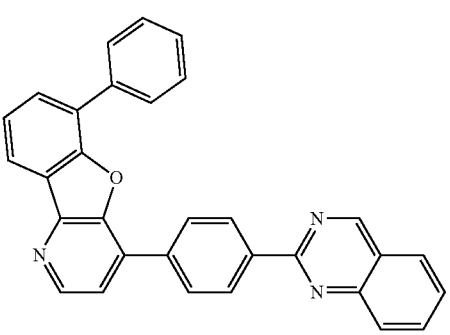
M-238
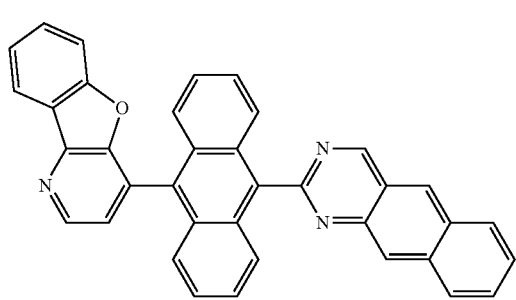
M-239
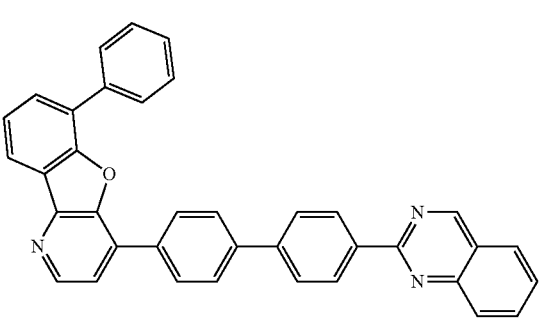

M-240
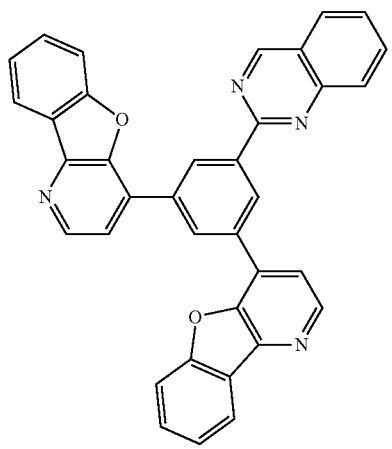
M-241
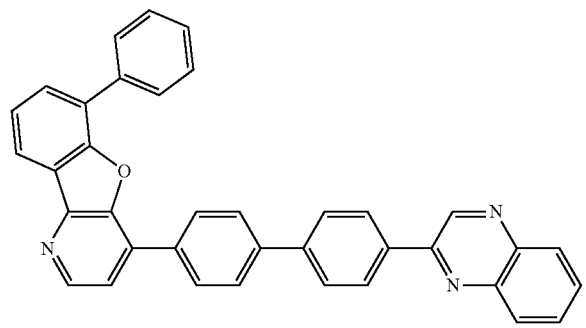
[Formula 47]
M-242
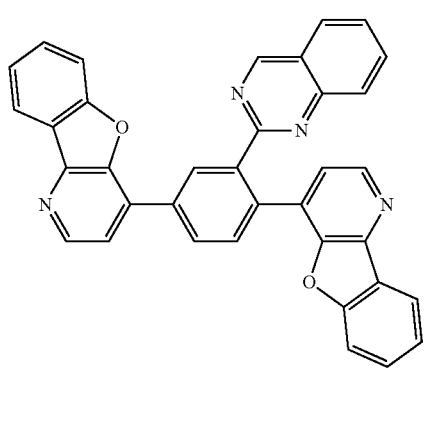
M-243
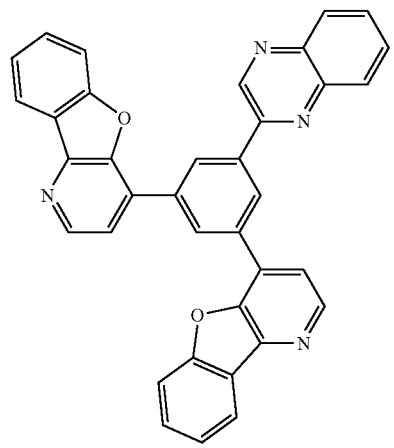
M-244
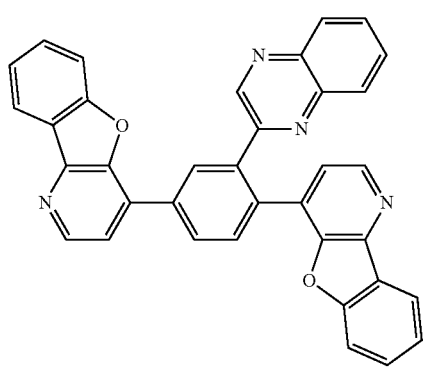
M-245
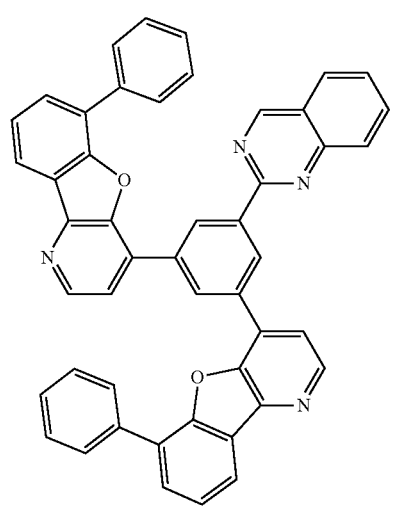

M-246
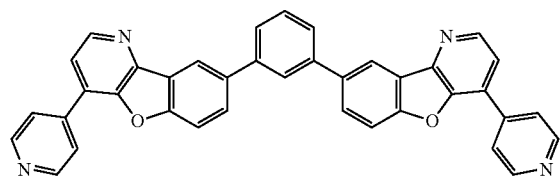
M-247
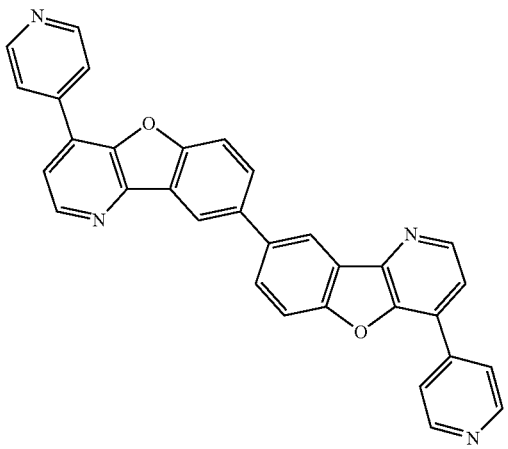
M-248
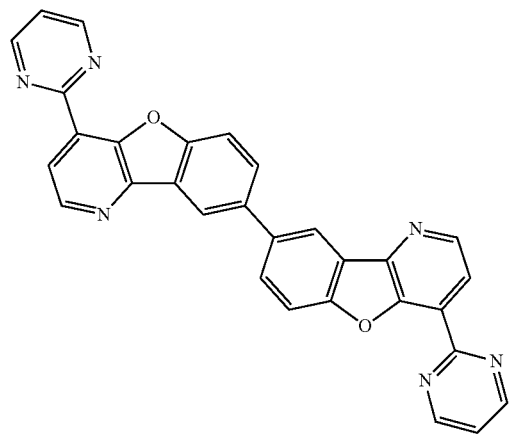
[Formula 48]
M-249
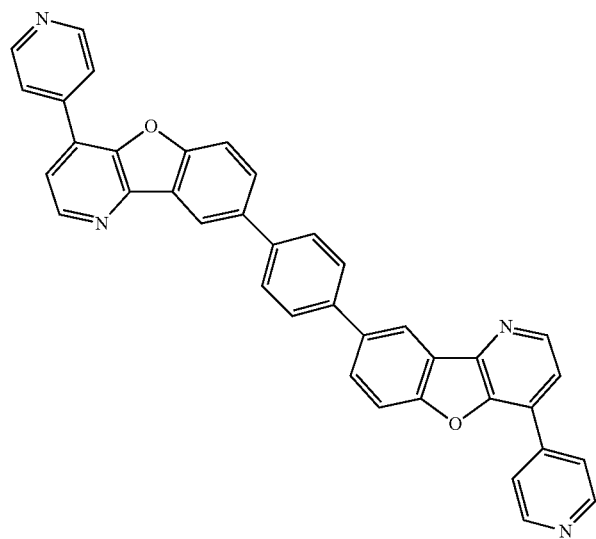
M-250
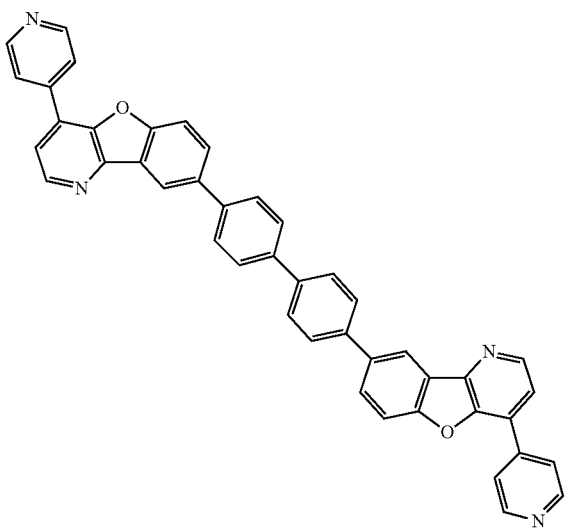

-continued
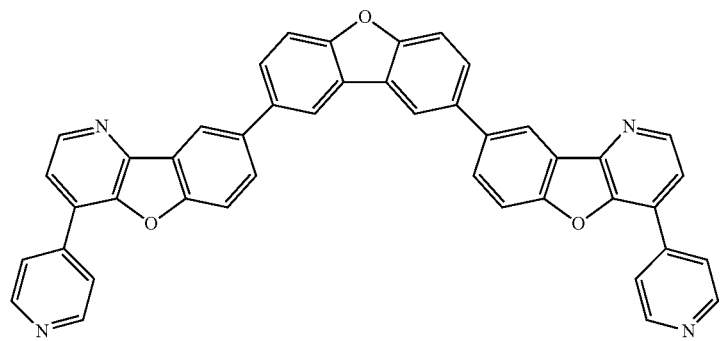
M-251
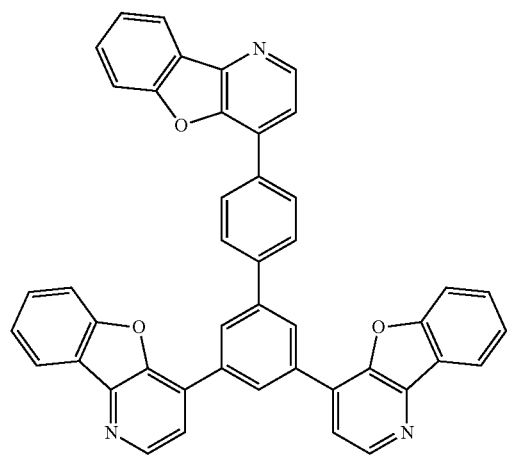
M-252
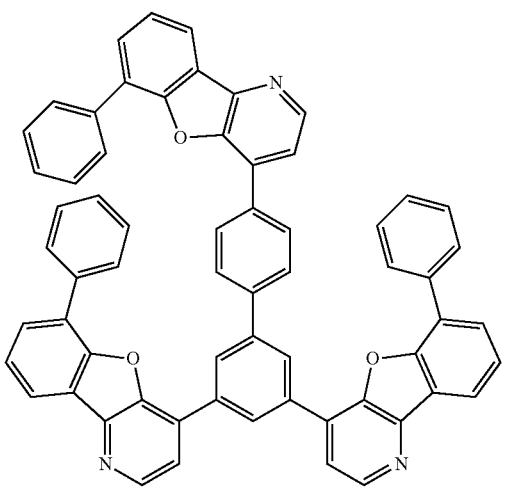
M-253
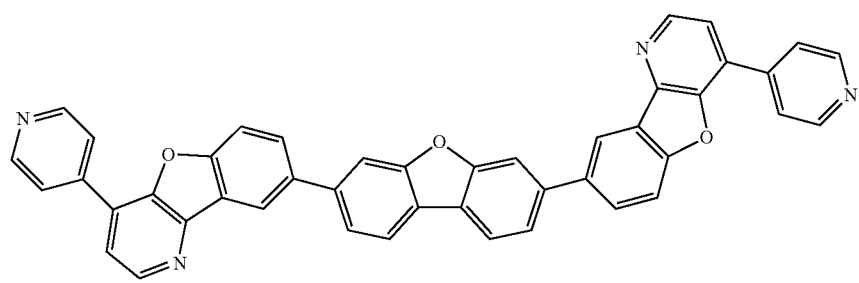
M-254
[Formula 49]
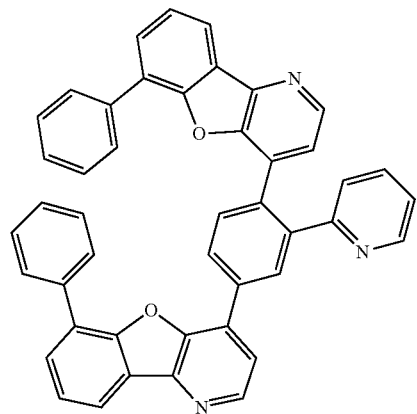
M-255
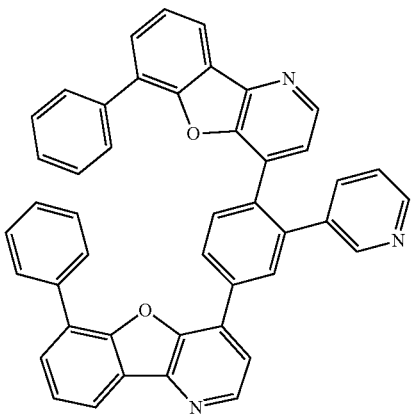
M-256

M-257
M-258
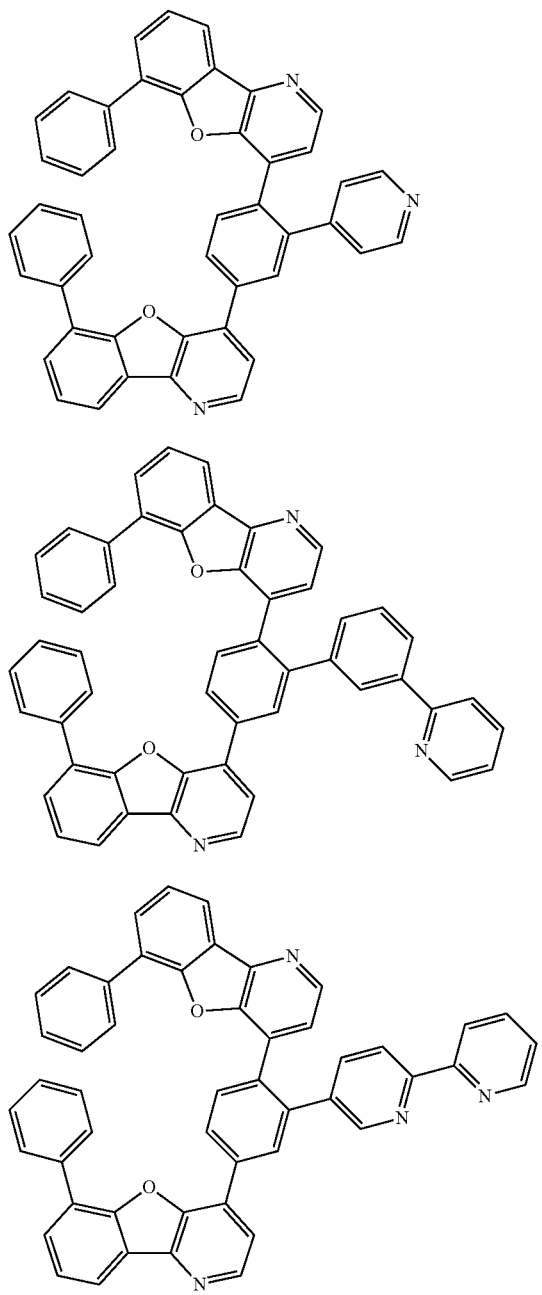
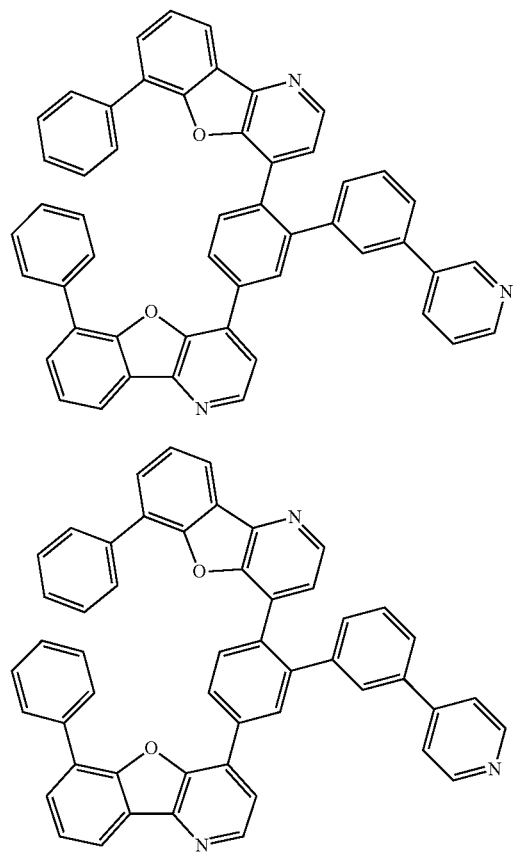
M-259
M-260
M-261
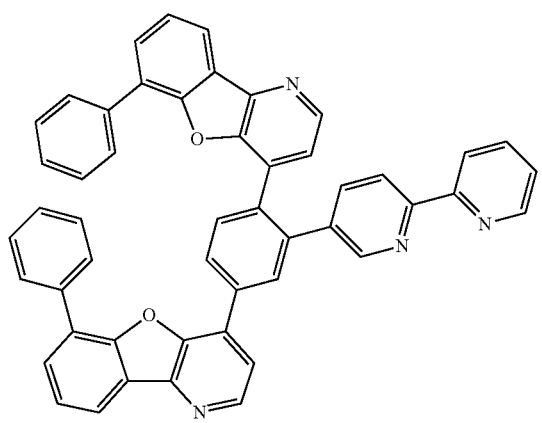
[Formula 50]
M-262
M-263
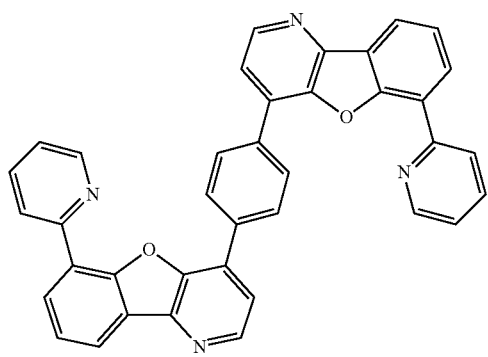
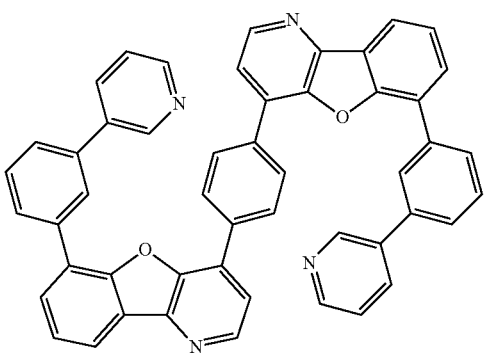

-continued
M-264
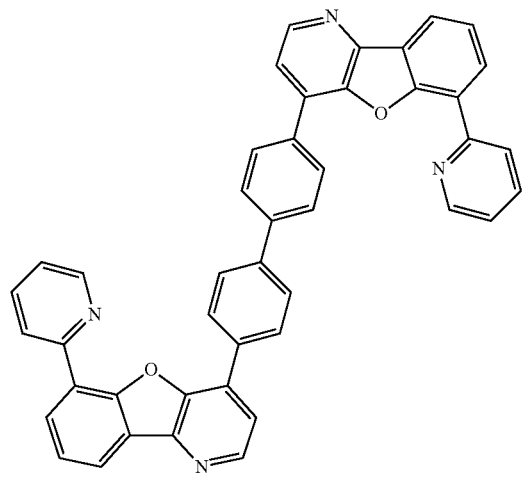
M-265
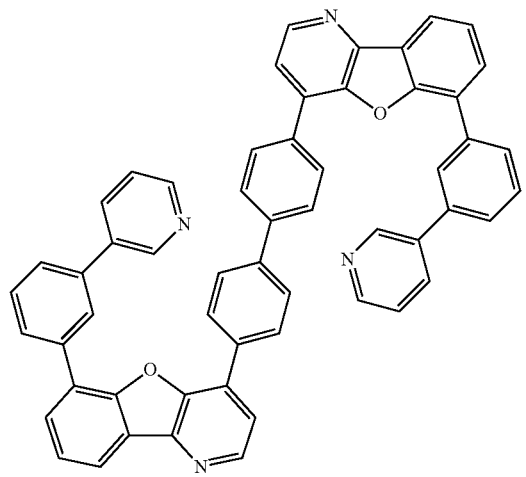
M-266
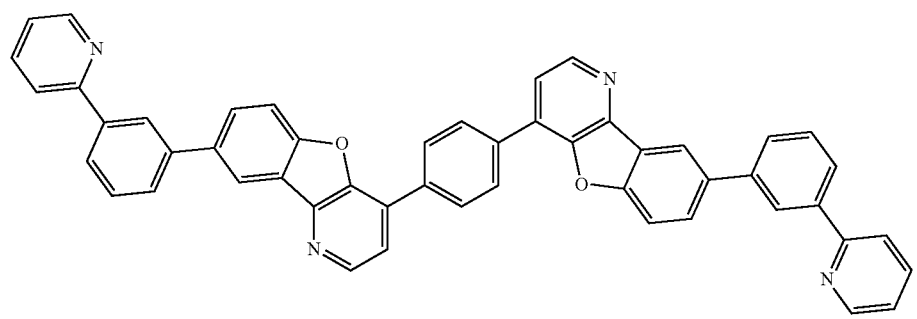
M-267
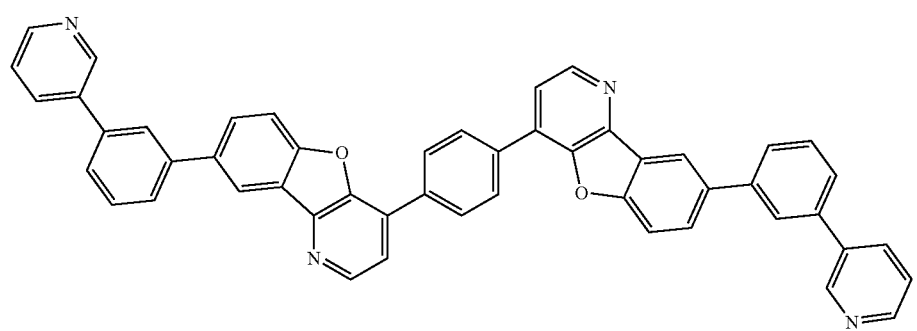
M-268
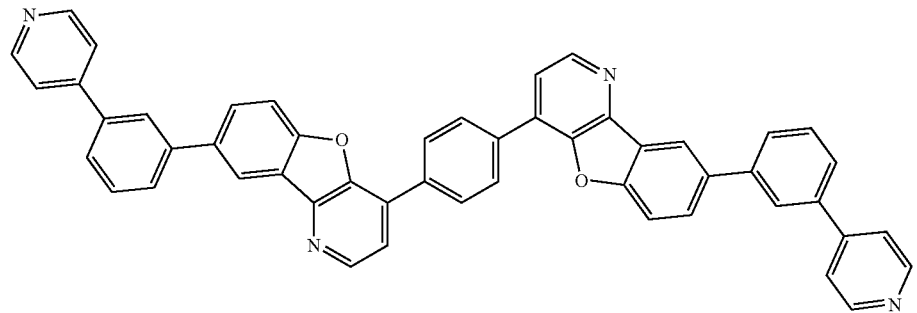

[Formula 51]
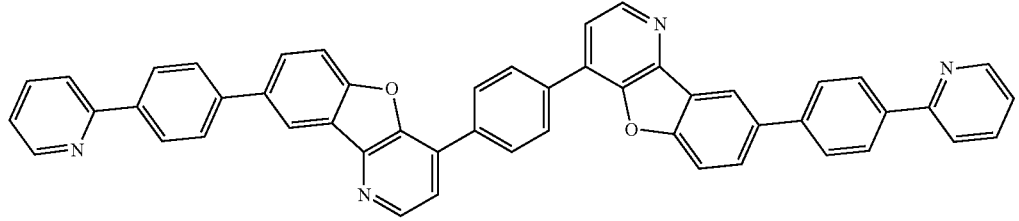
M-269
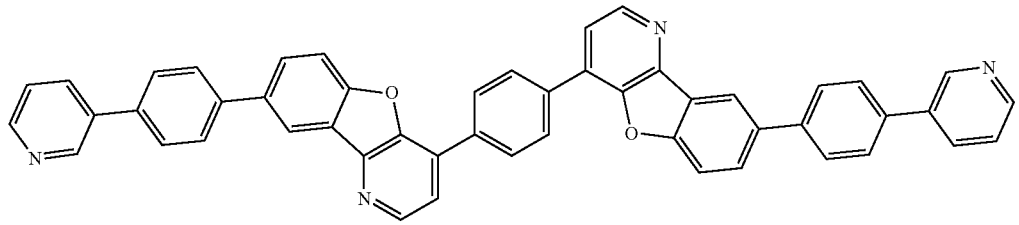
M-270
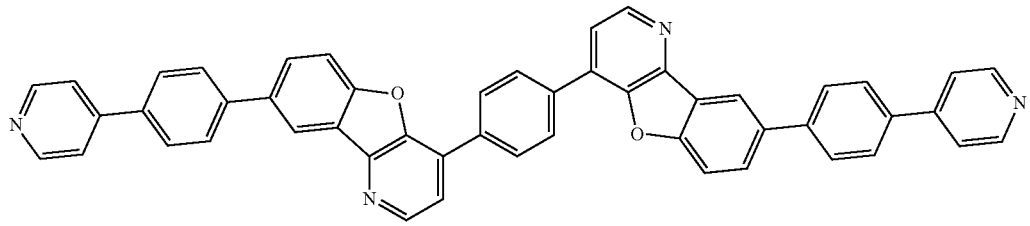
M-271
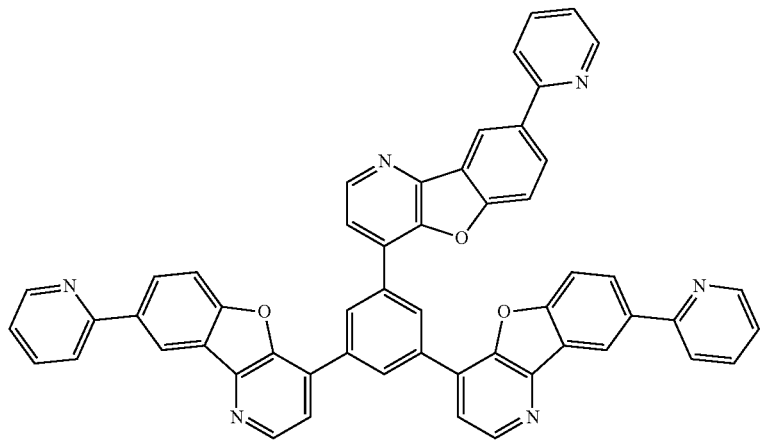
M-272
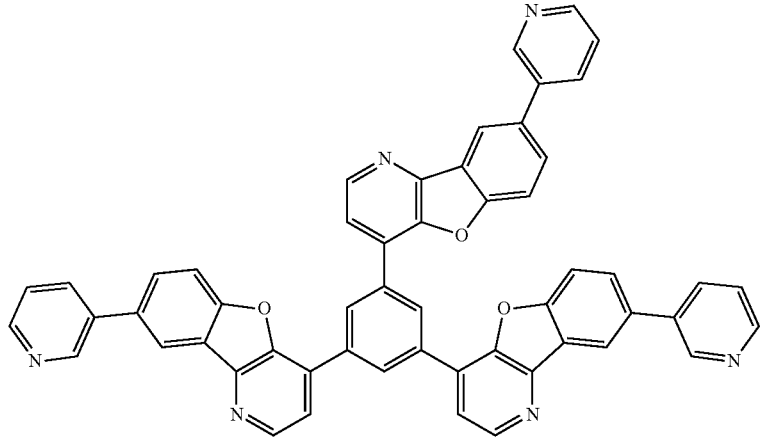
M-273

[Formula 52]
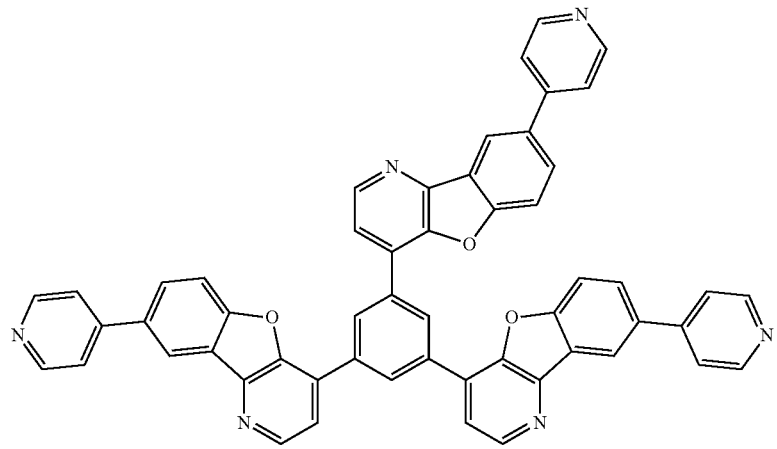
M-274
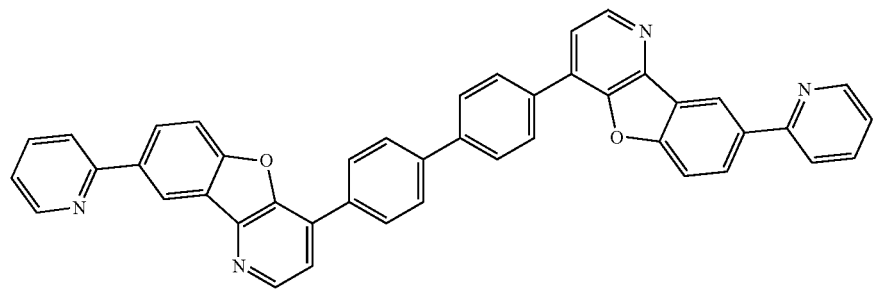
M-275
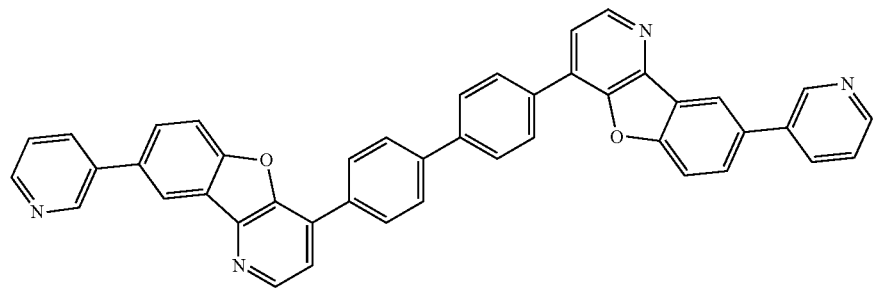
M-276
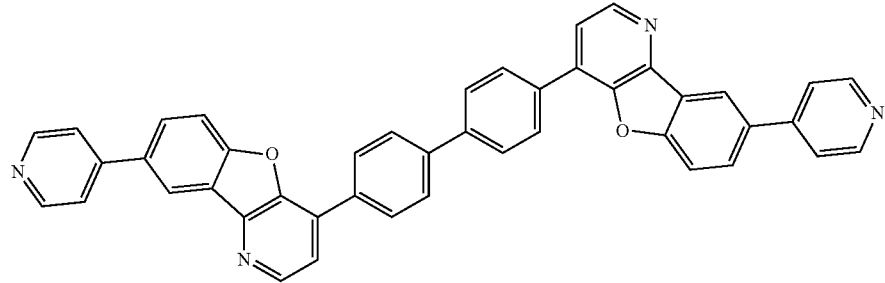
M-277

-continued
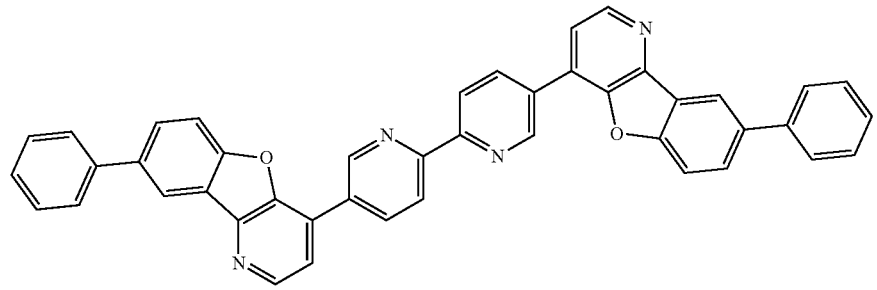
M-278
[Formula 53]
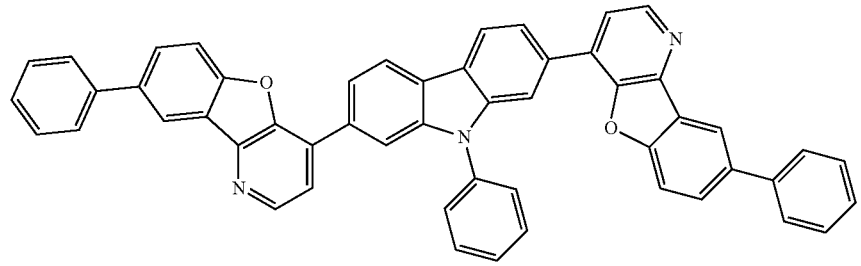
M-279
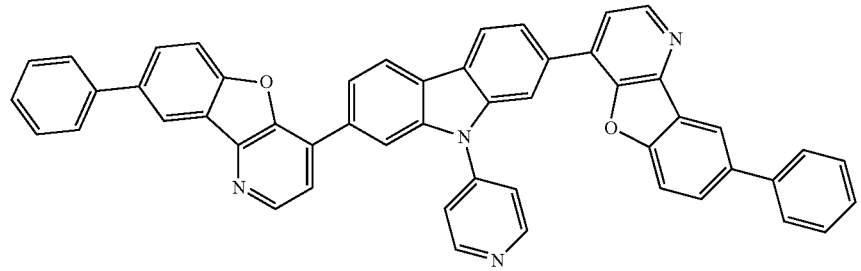
M-280
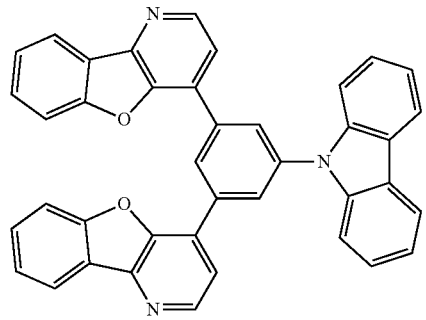
M-281
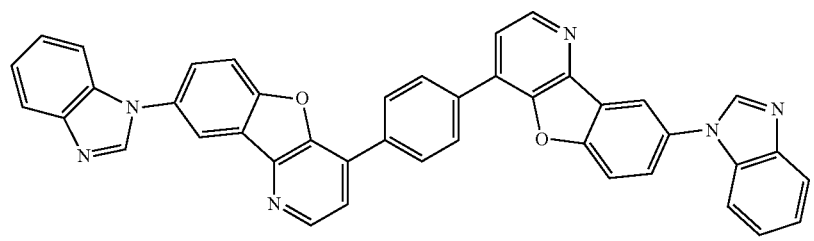
M-282

-continued
M-283
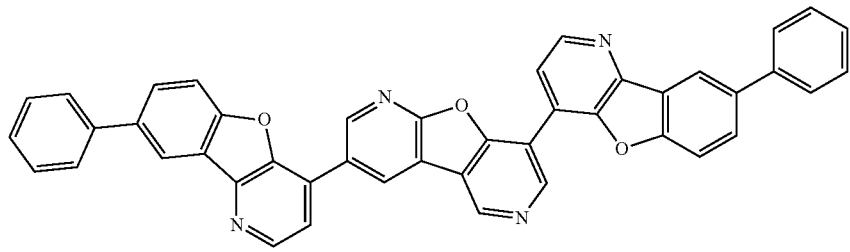
[Formula 54]
M-284
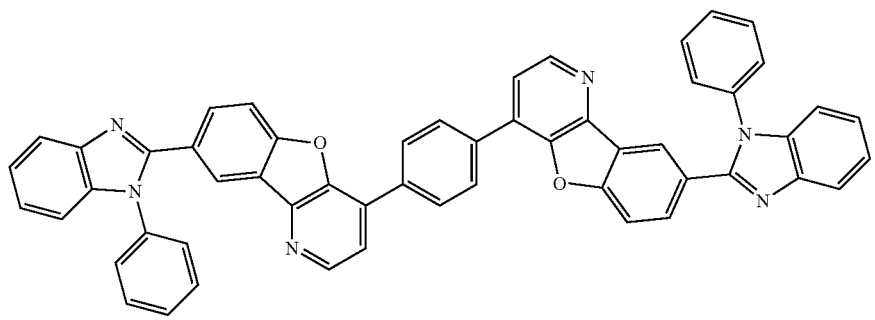
M-285
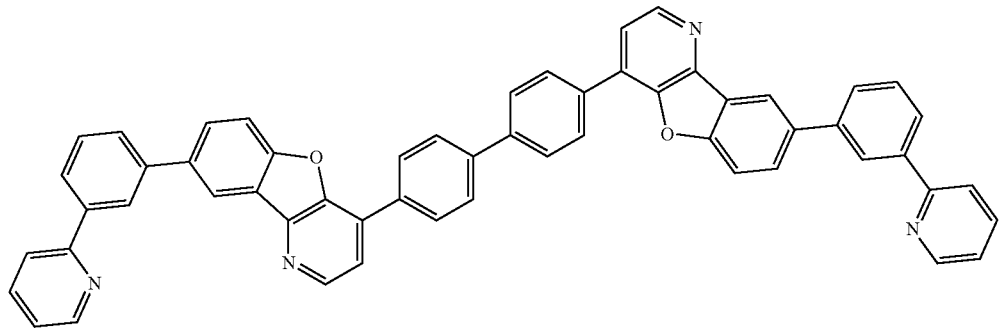
M-286
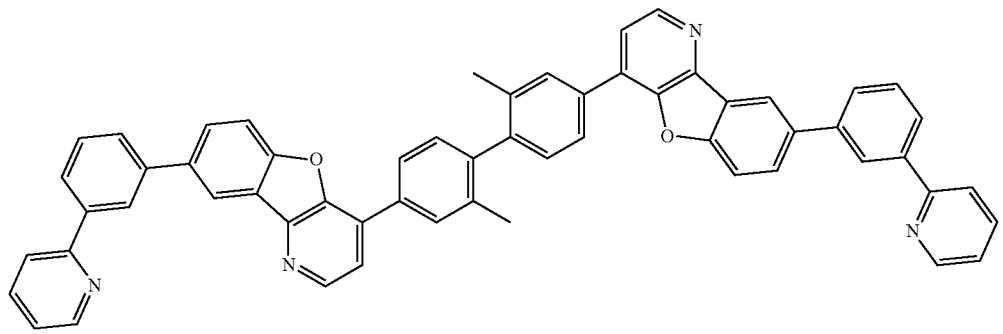
M-287
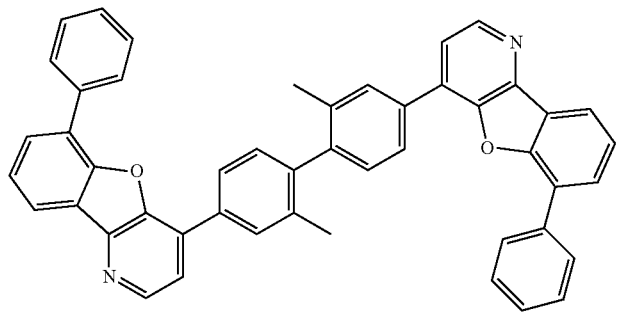

[Formula 55]
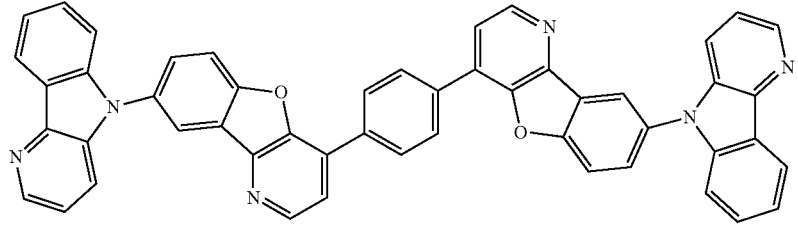
M-288
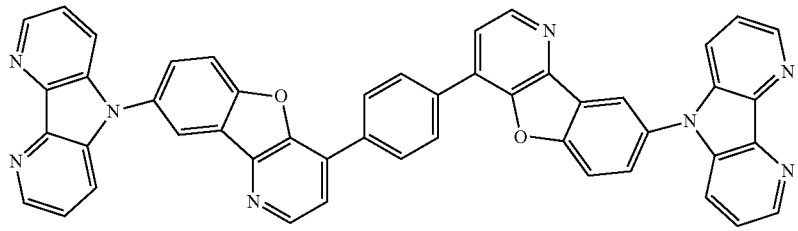
M-289
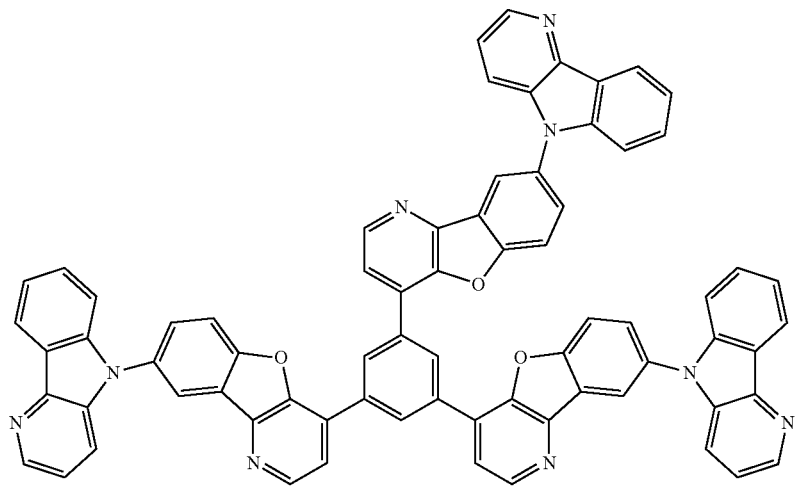
M-290
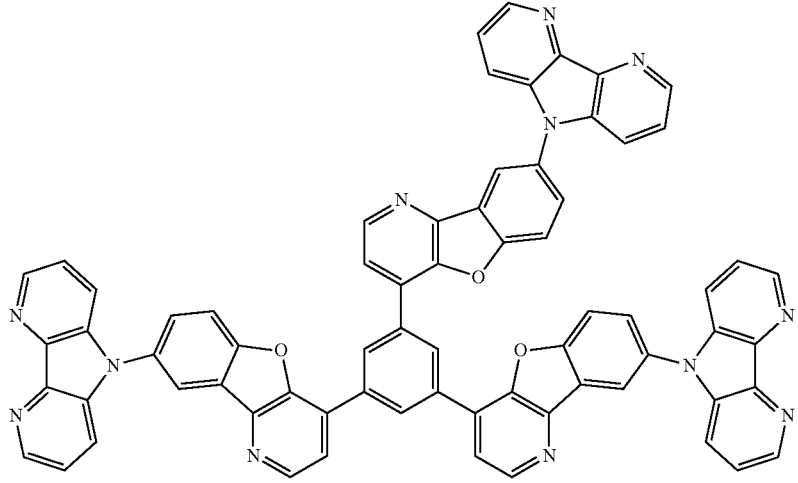
M-291

[Formula 56]
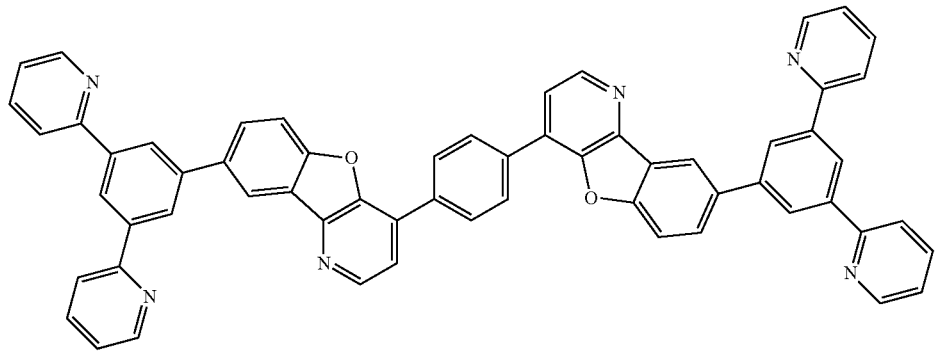
M-292
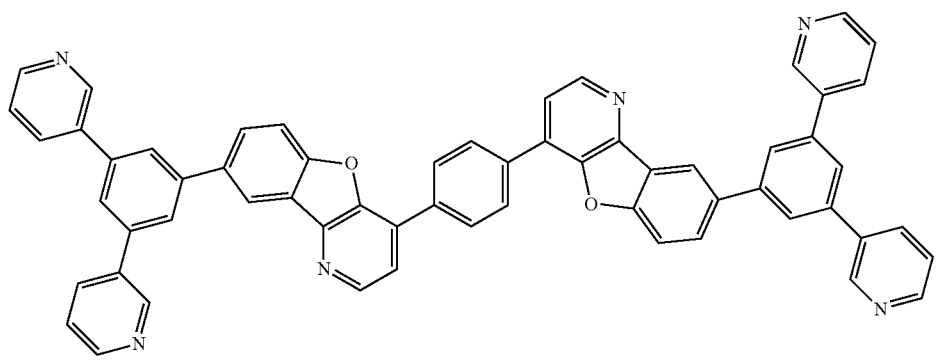
M-293
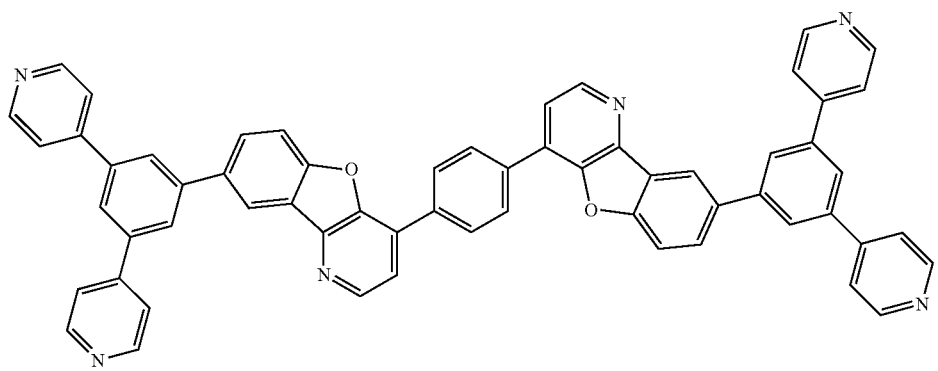
M-294
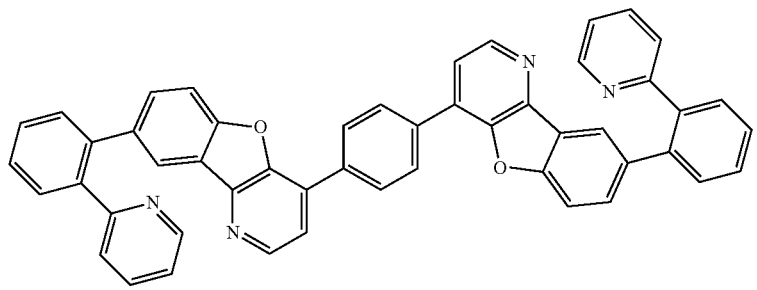
M-295
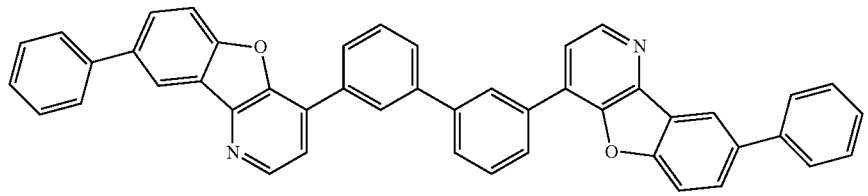
M-296

[Formula 57]
M-297
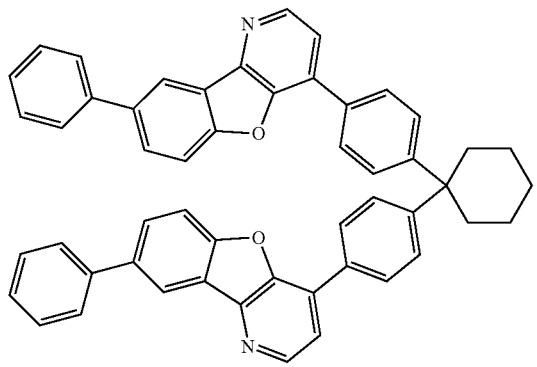
M-298
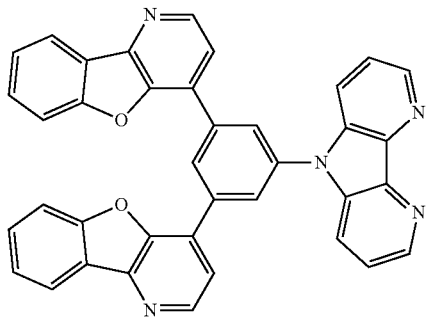
M-299
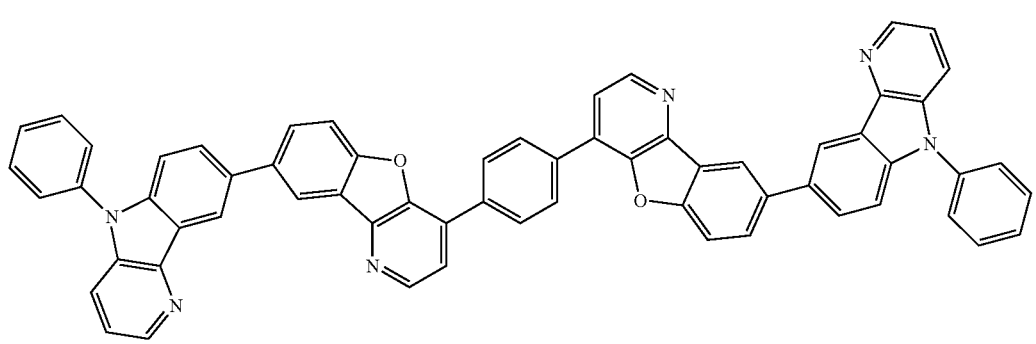
M-300
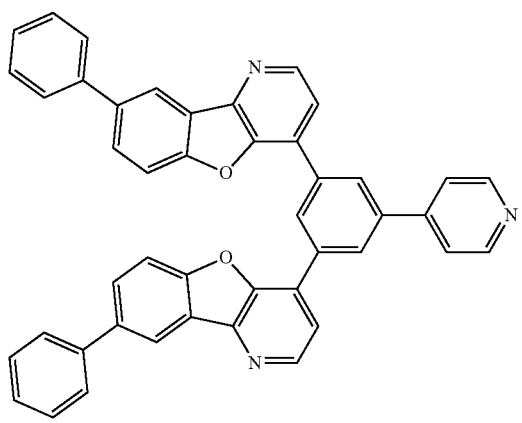
M-301
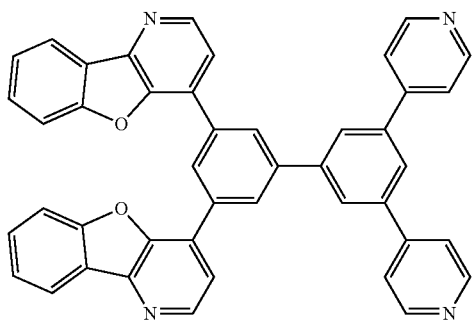
M-302
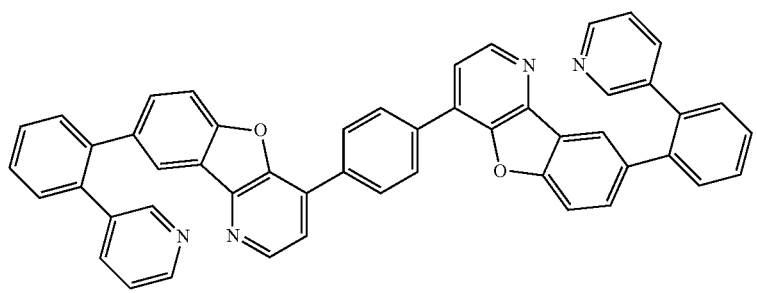

[Formula 58]
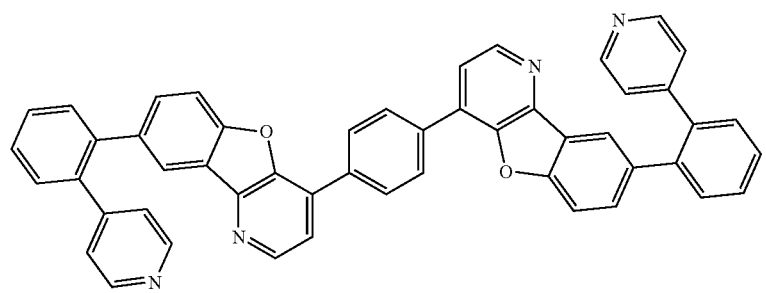
M-303
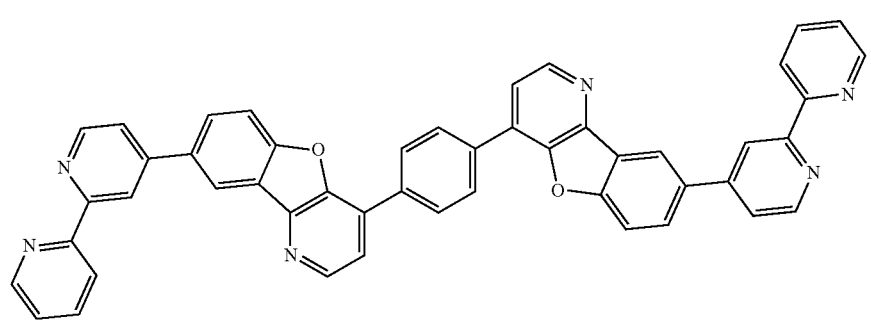
M-304
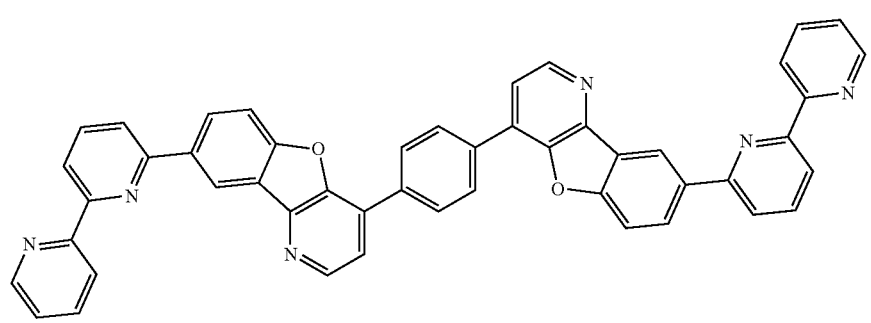
M-305
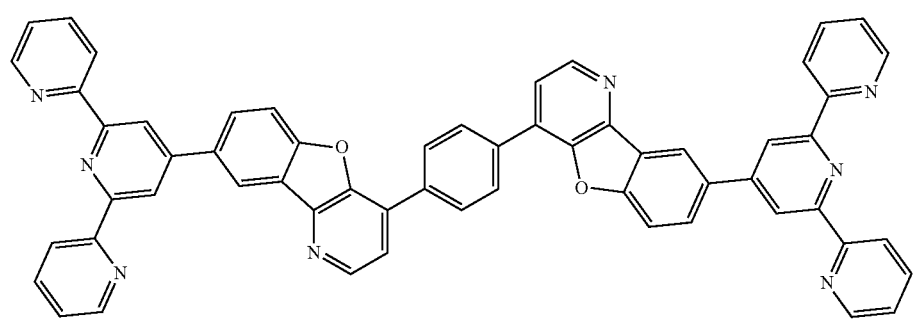
M-306
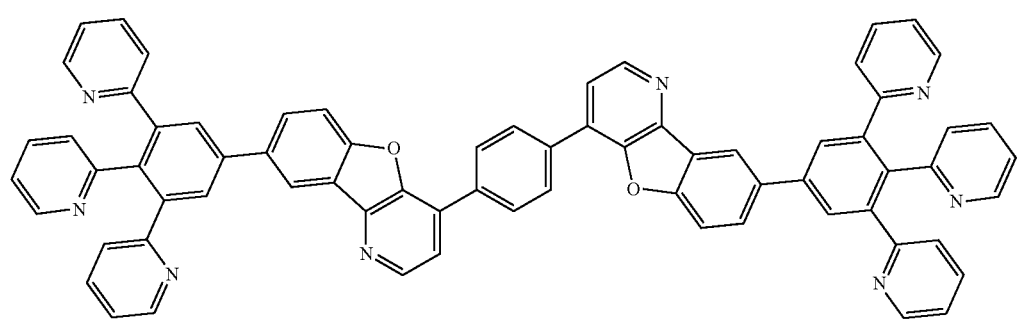
M-307

[Formula 59]
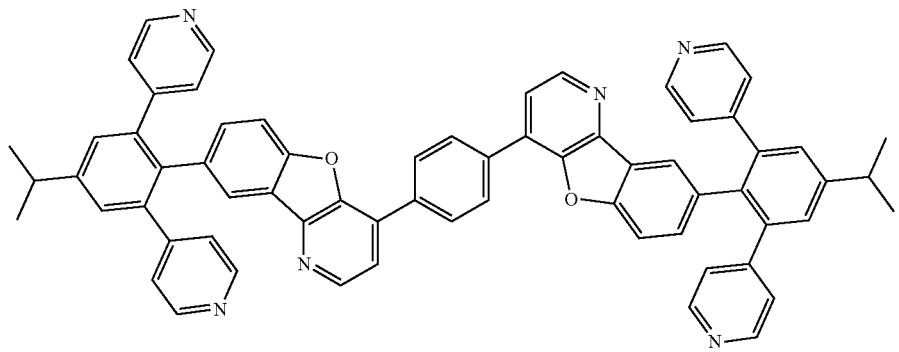
M-308
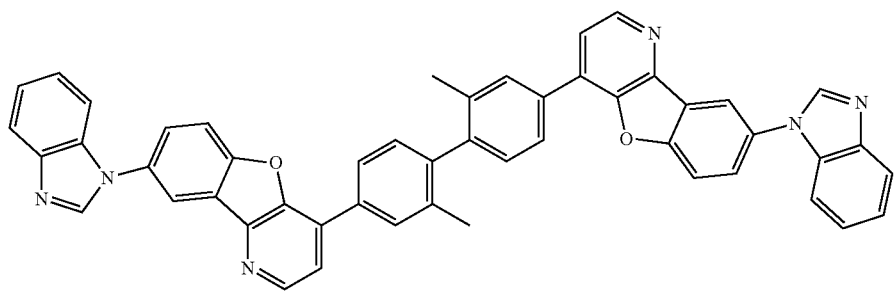
M-309
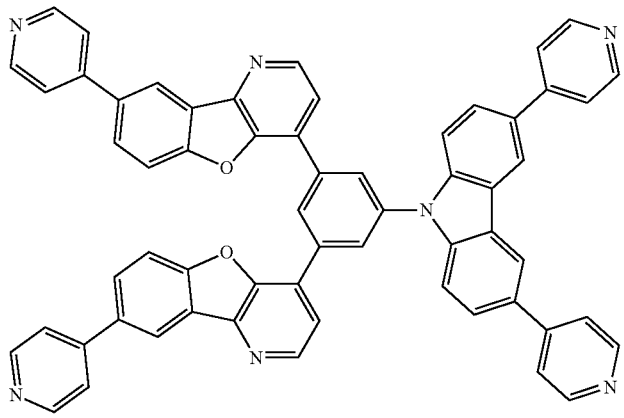
M-310
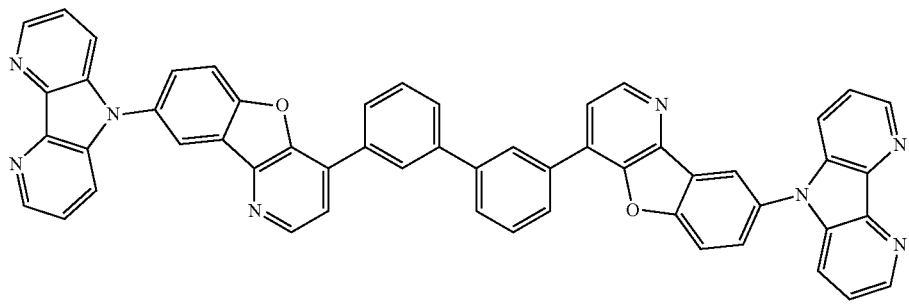
M-311

[Formula 60]
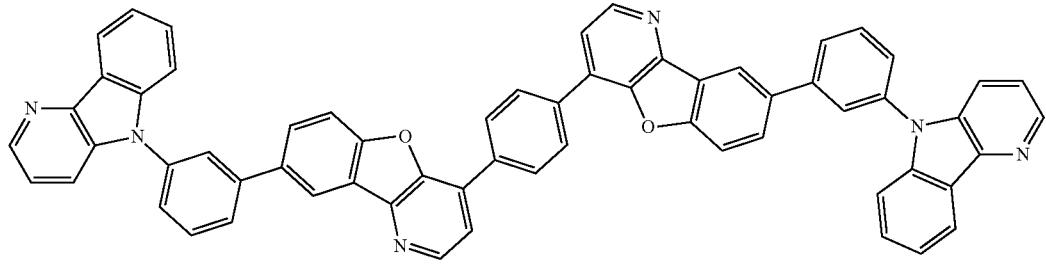
M-312
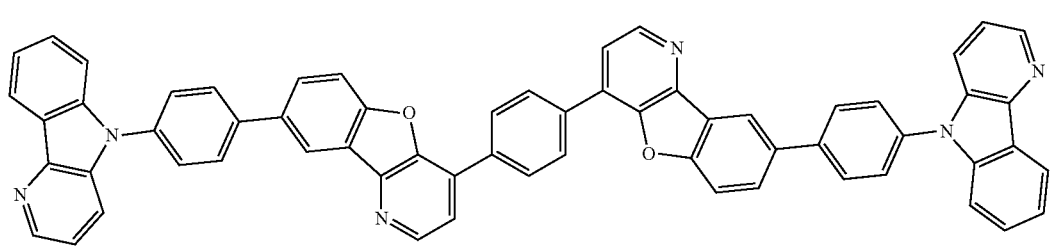
M-313
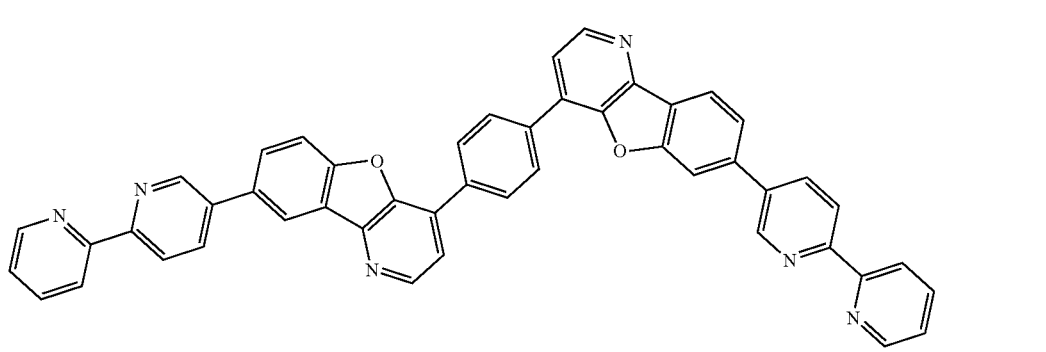
M-314
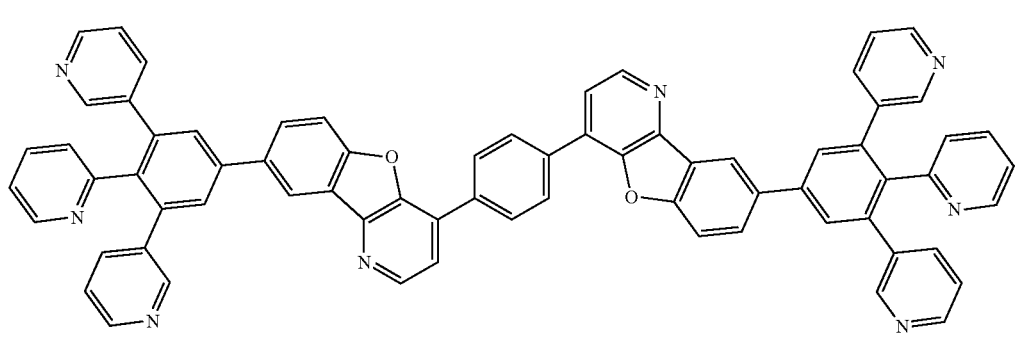
315
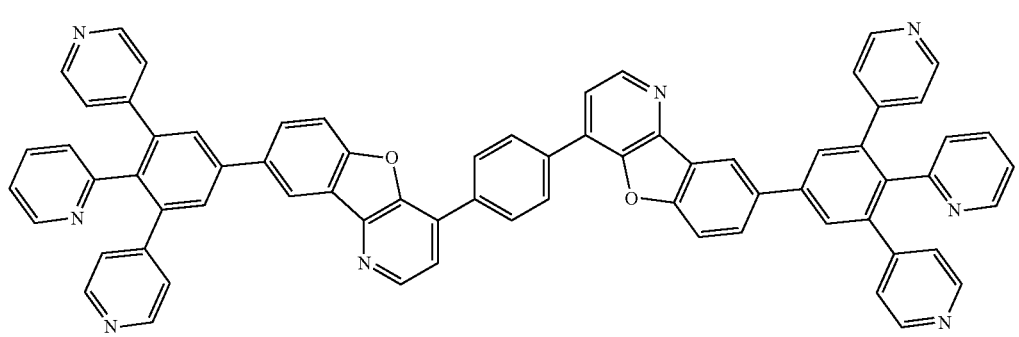
M-316

[Formula 61]
M-317
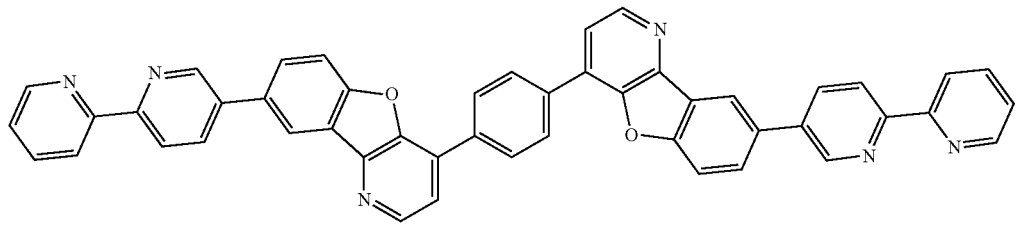
M-318
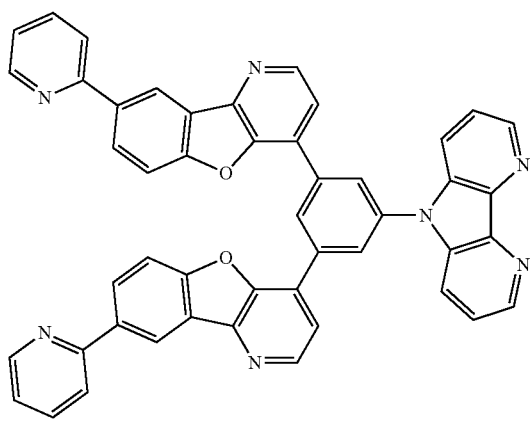
M-319
[Formula 62]
M-320
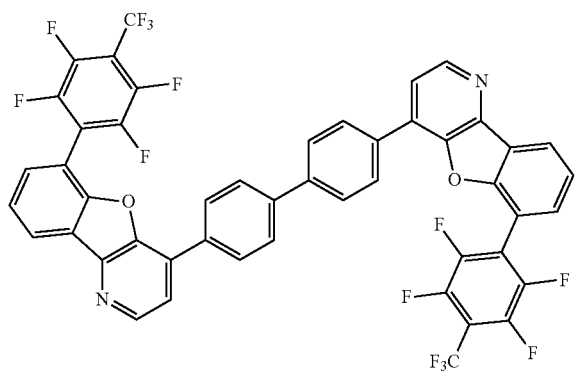
M-321
M-322
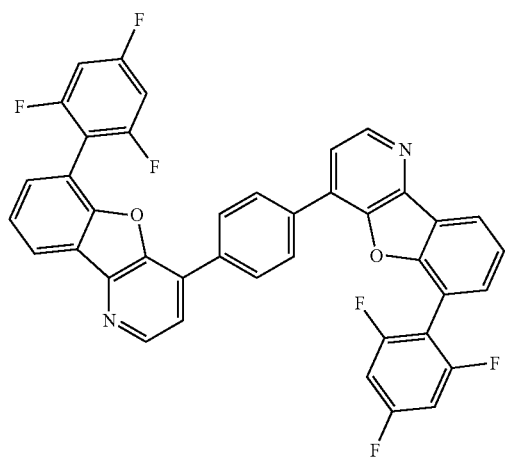
M-323
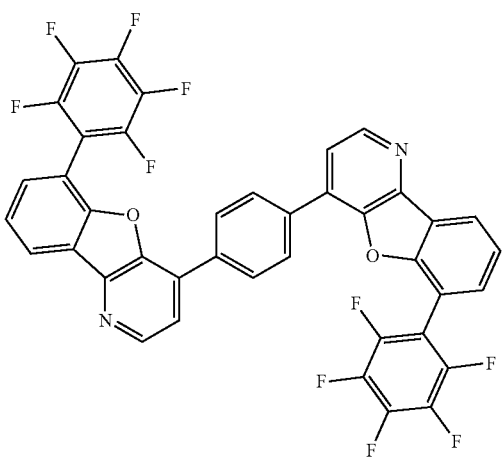

-continued
M-324
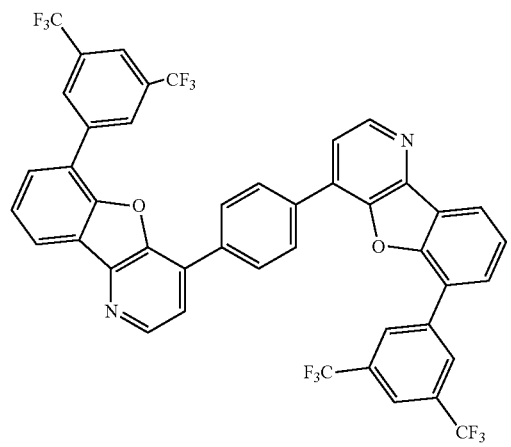
M-325
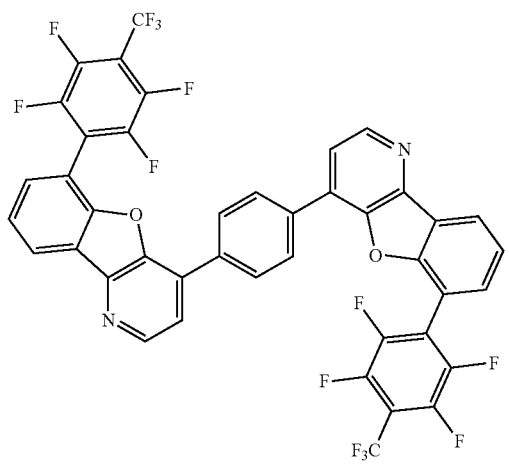
[Formula 63]
M-326
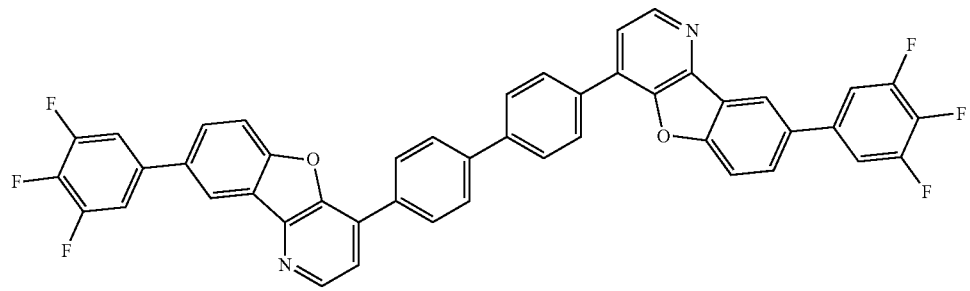
M-327
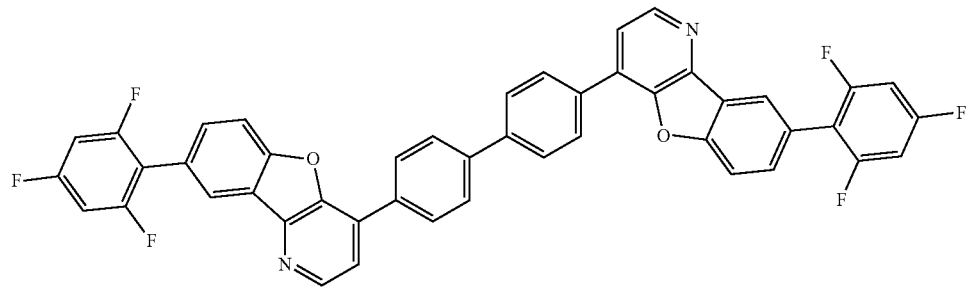
M-328
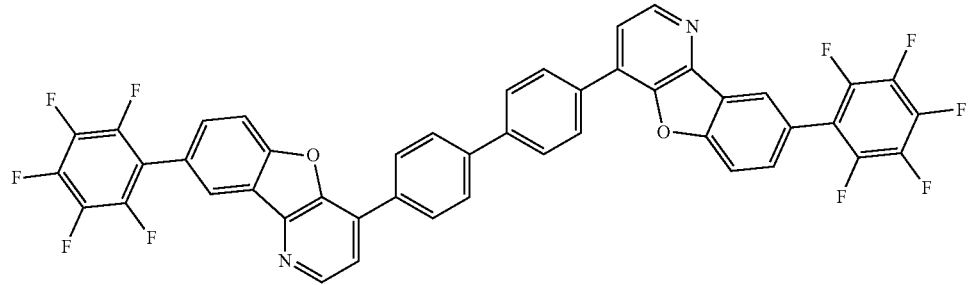

-continued
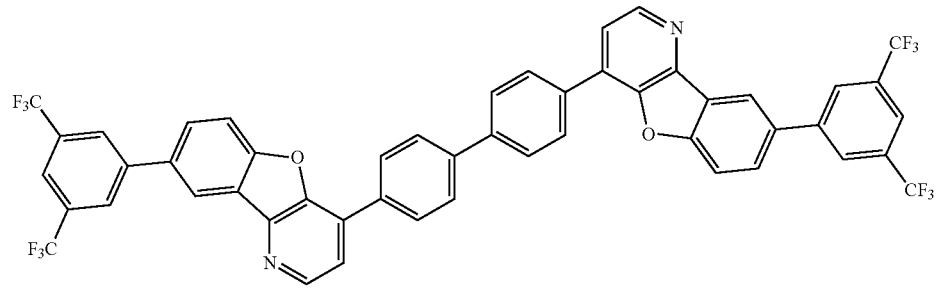
M-329
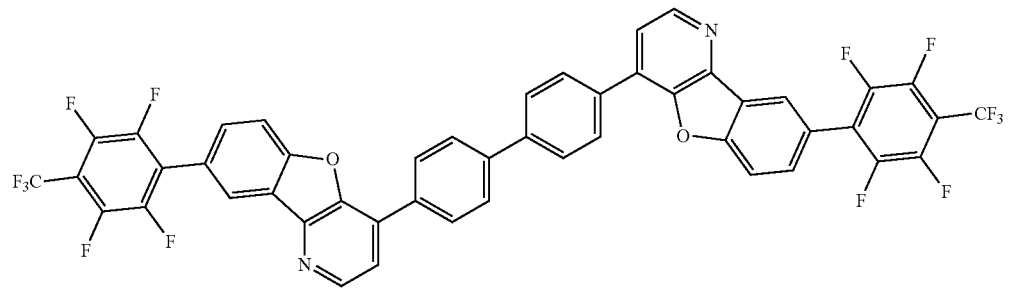
M-330
[Formula 64]
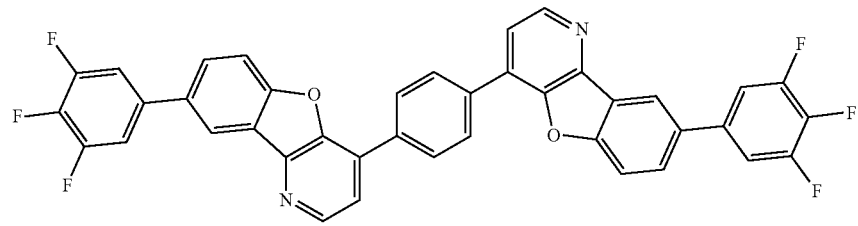
M-331
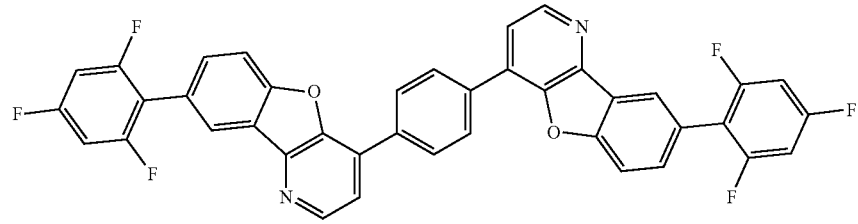
M-332
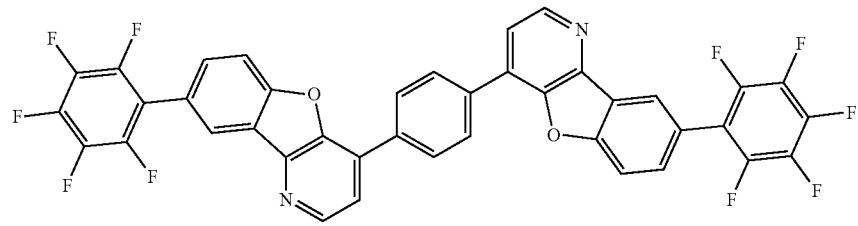
M-333
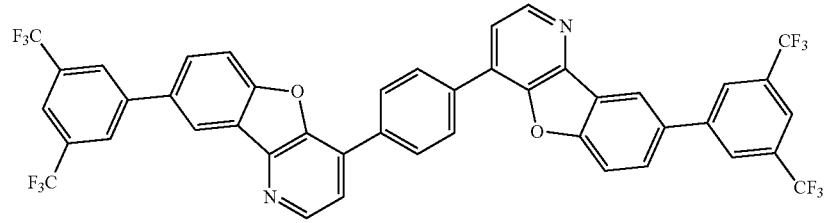
M-334

M-335
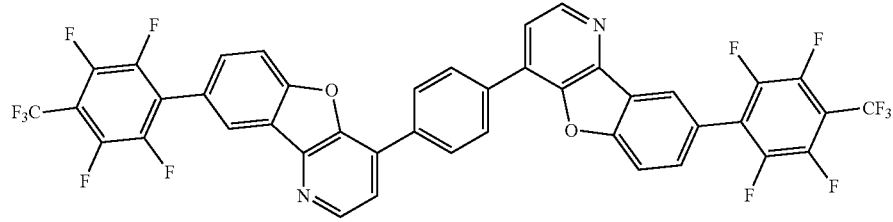
[Formula 65]
M-336
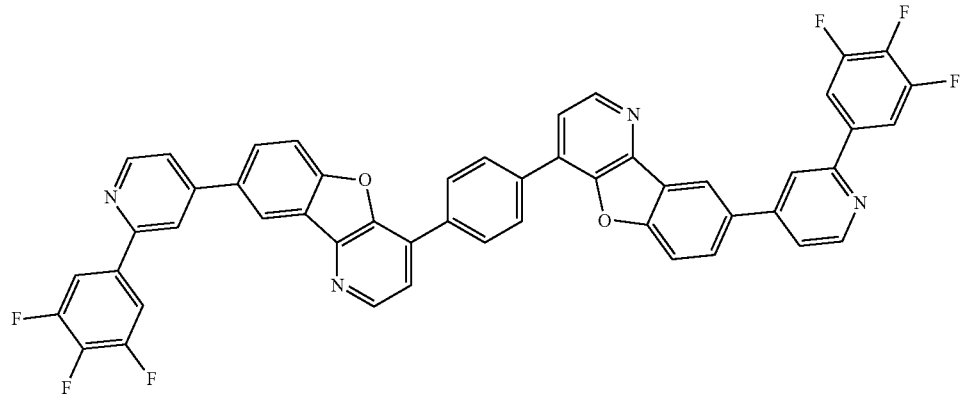
M-337
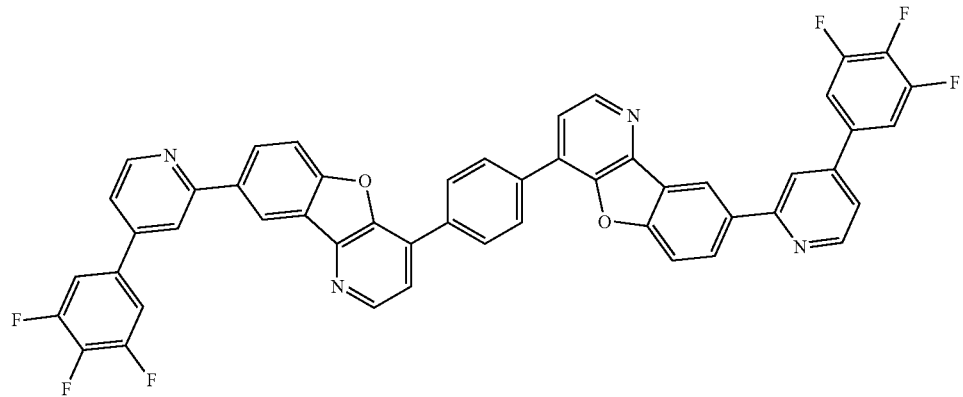
M-338
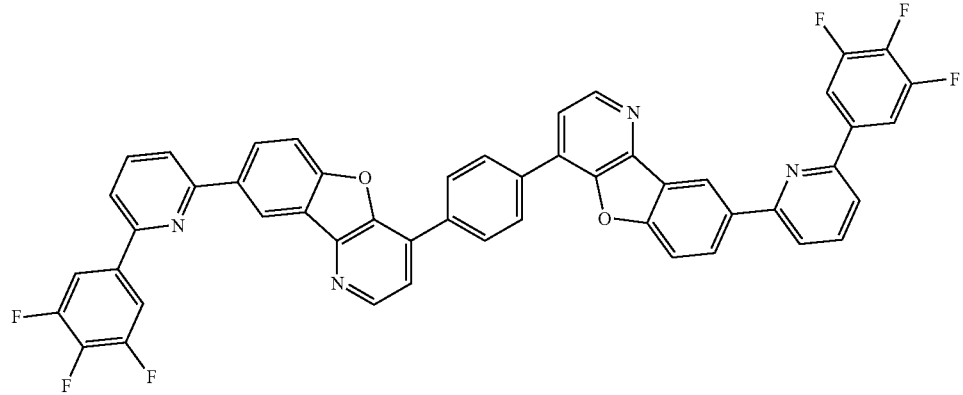

M-339
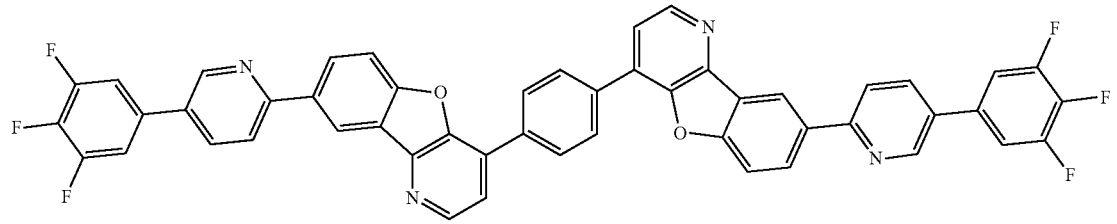
M-340
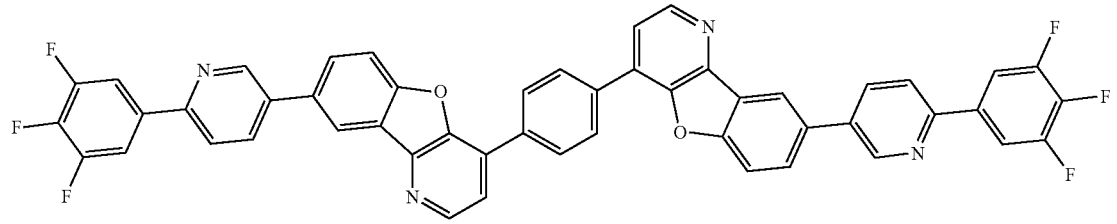
[Formula 66]
M-341
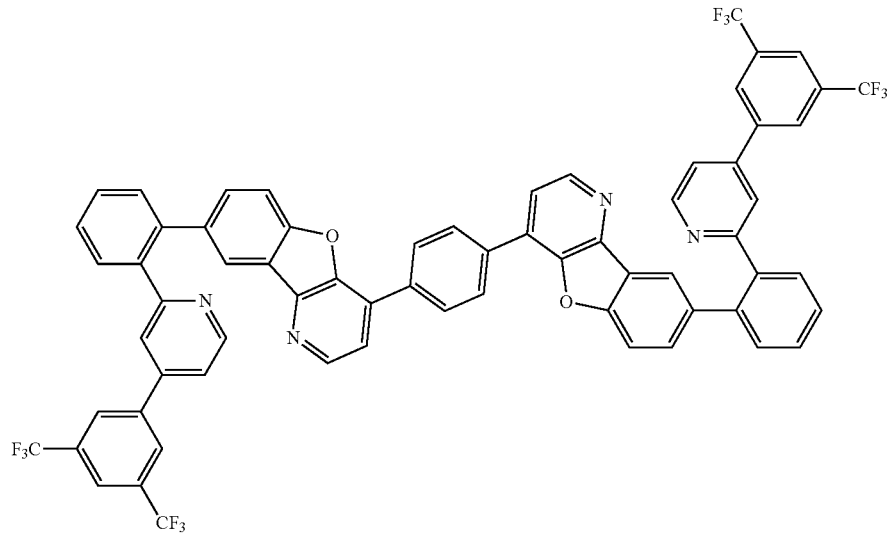
M-342
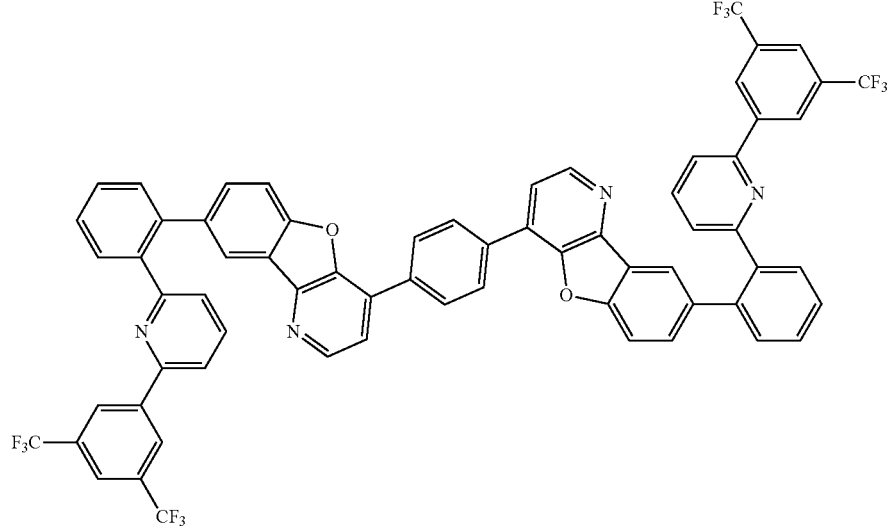

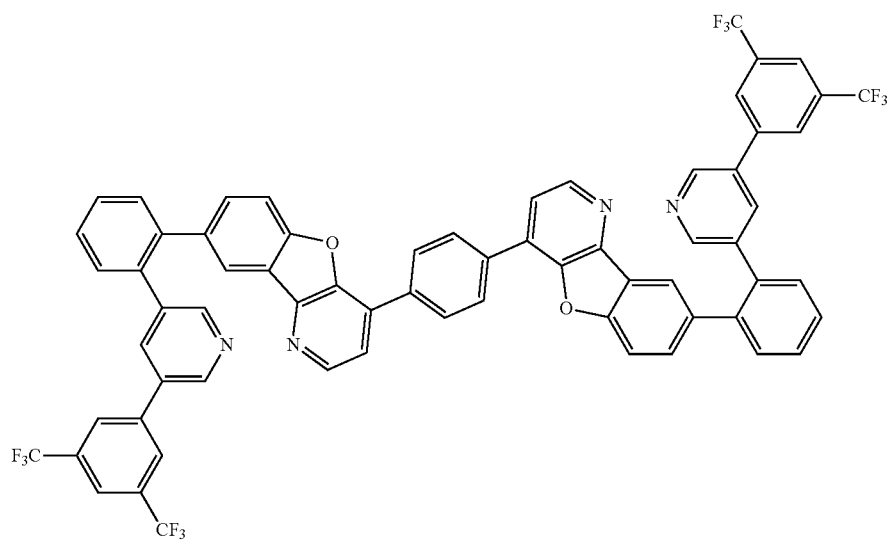
M-343
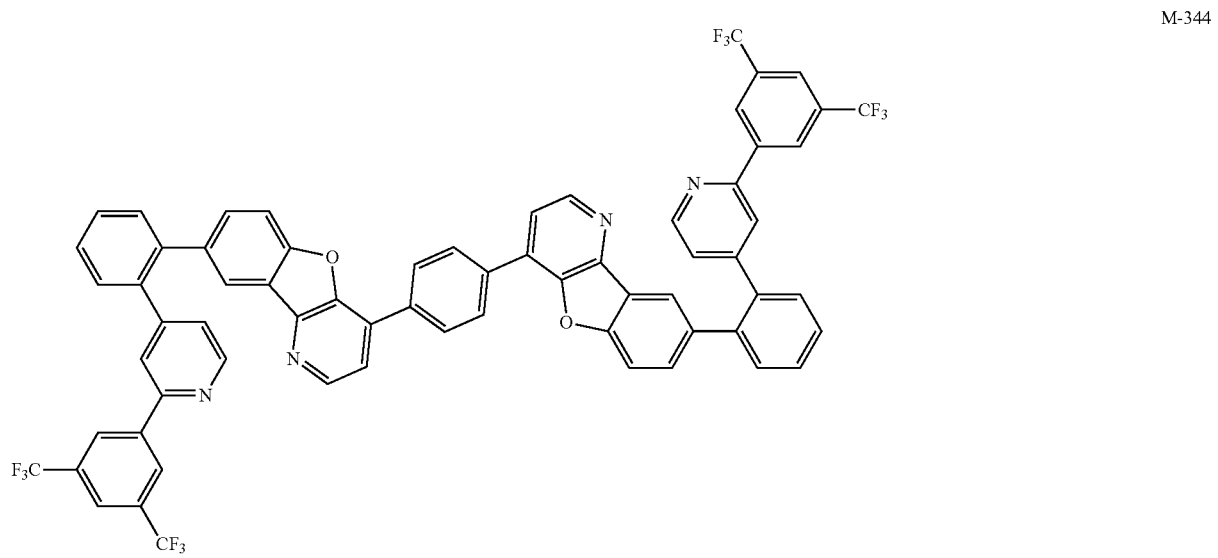
M-344
[Formula 67]
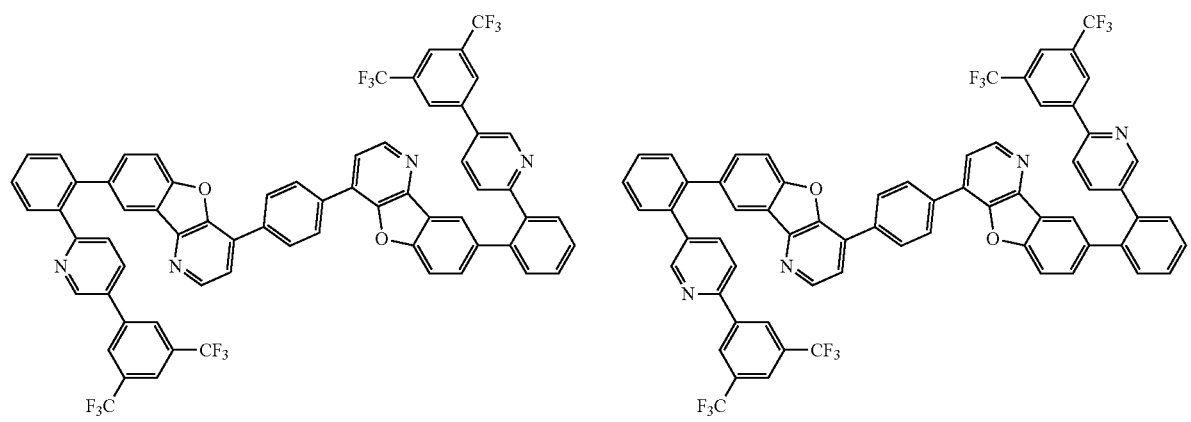
M-345　　M-346

-continued
M-347
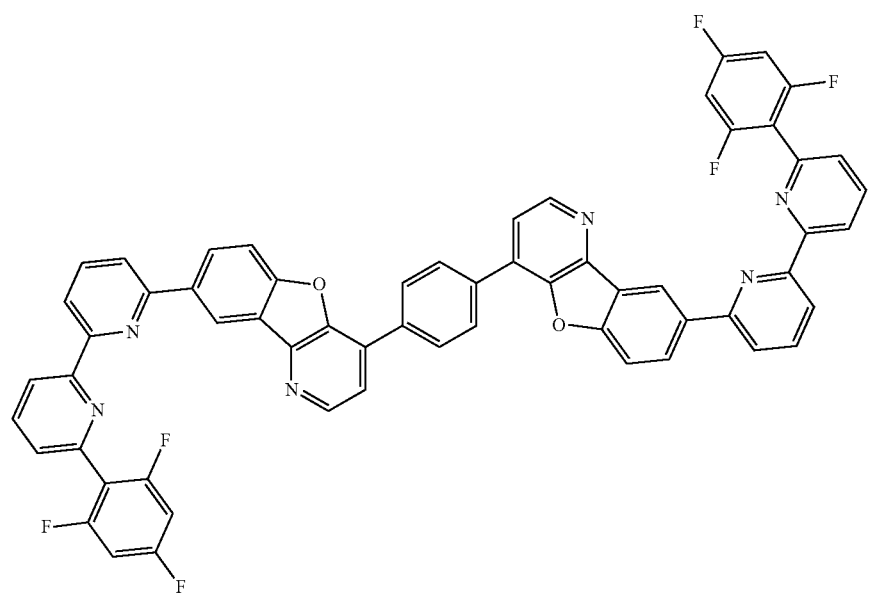
M-348
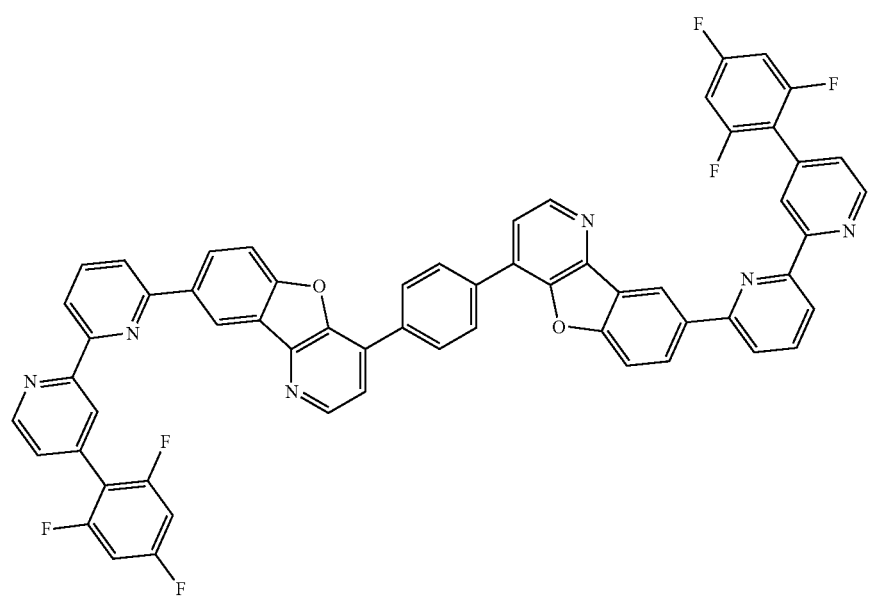

[Formula 68]
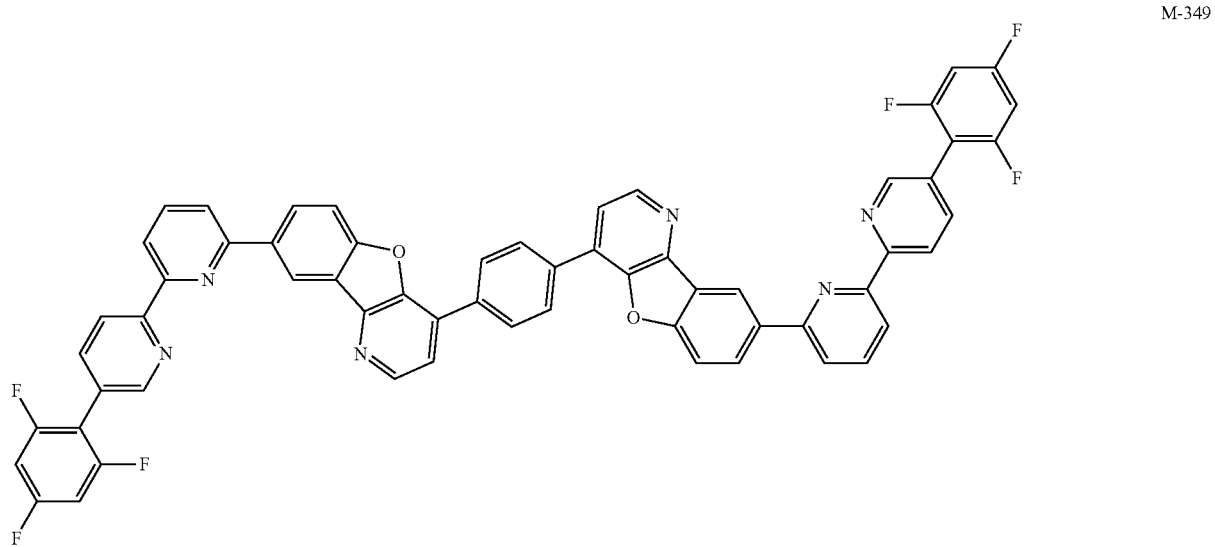
M-349
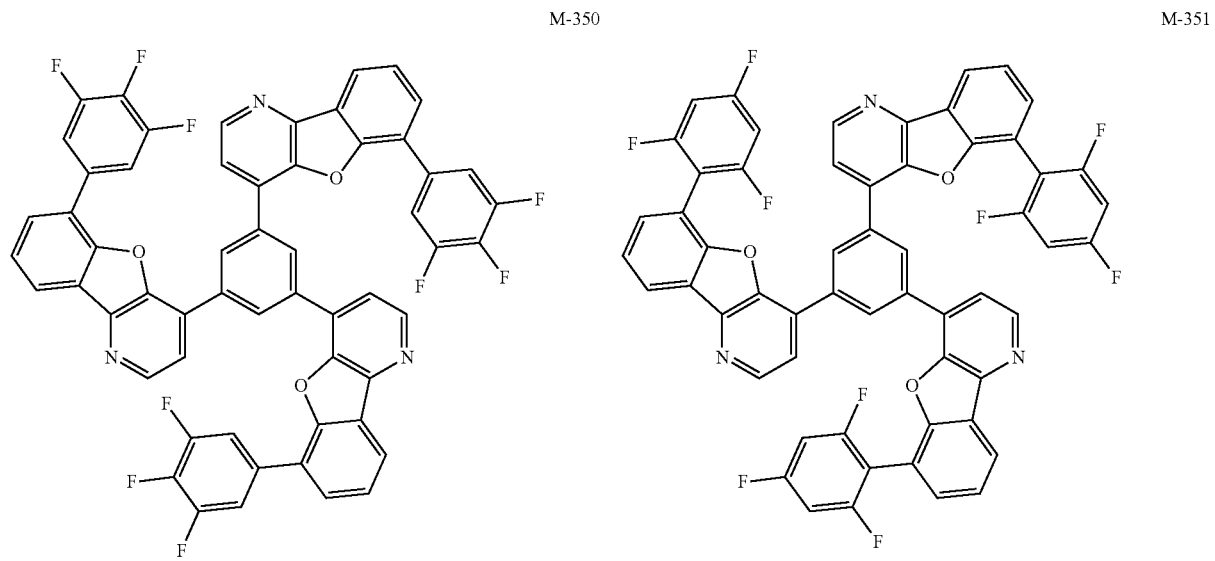
M-350
M-351

M-352
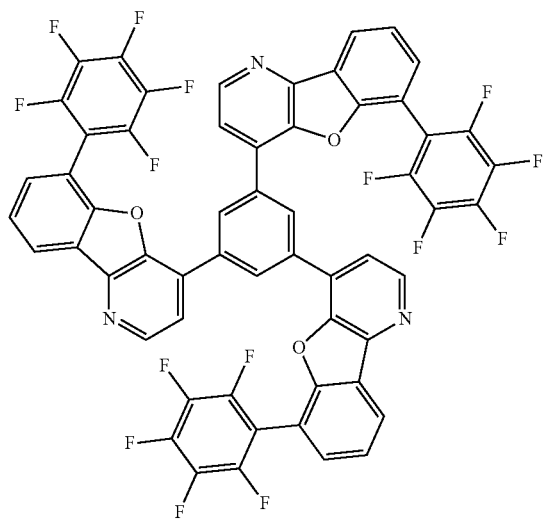
M-353
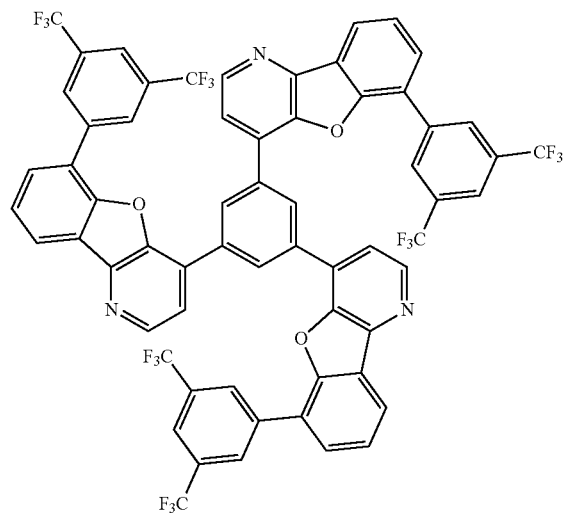
[Formula 69]
M-354
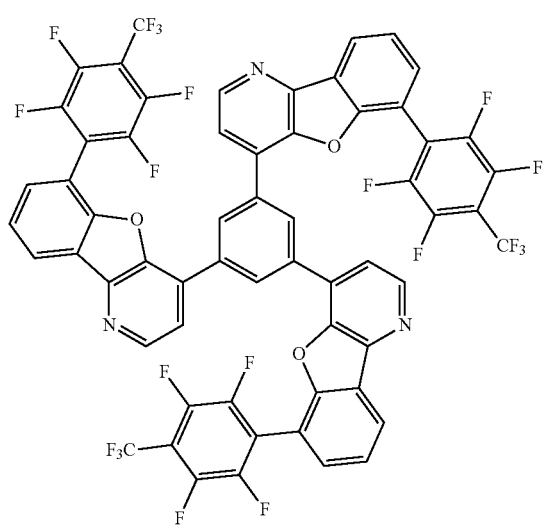
M-355
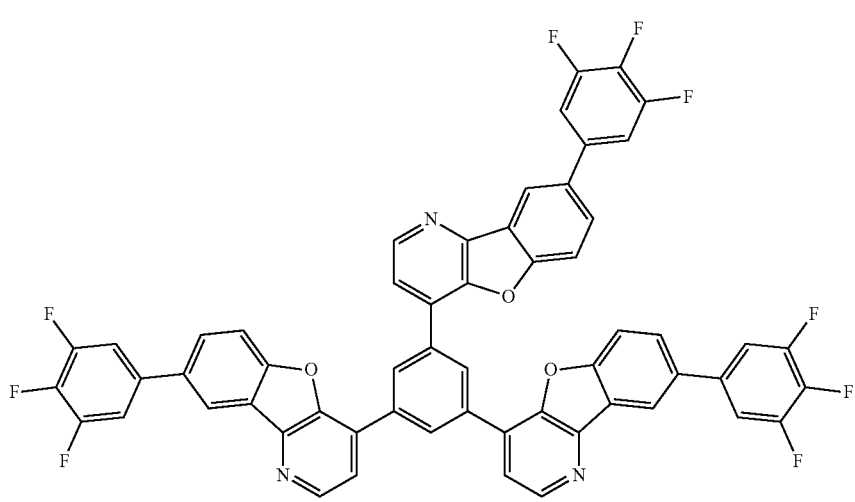

-continued
M-356
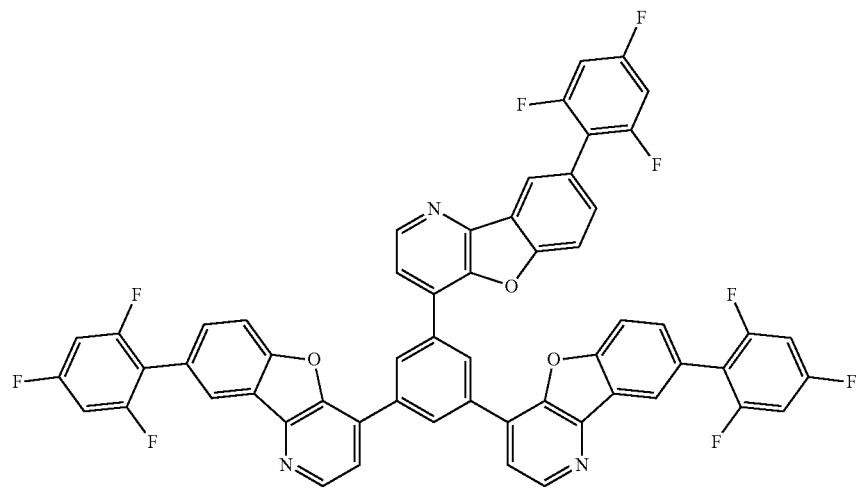
[Formula 70]
M-357
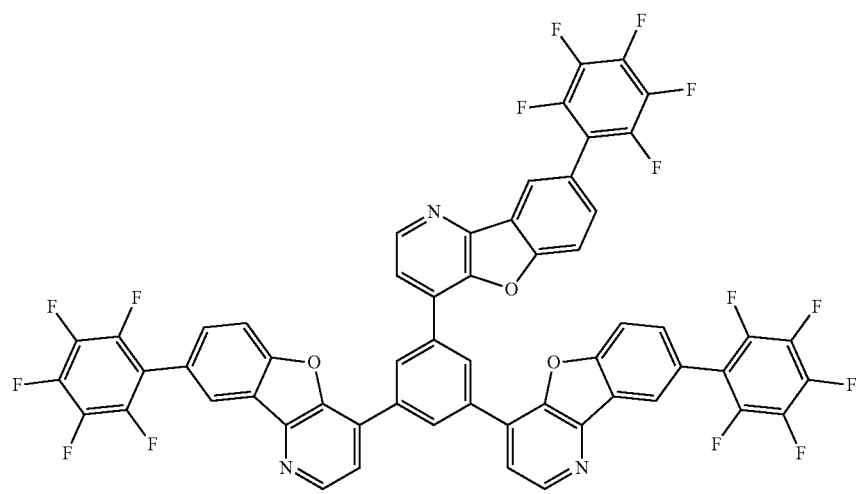
M-358
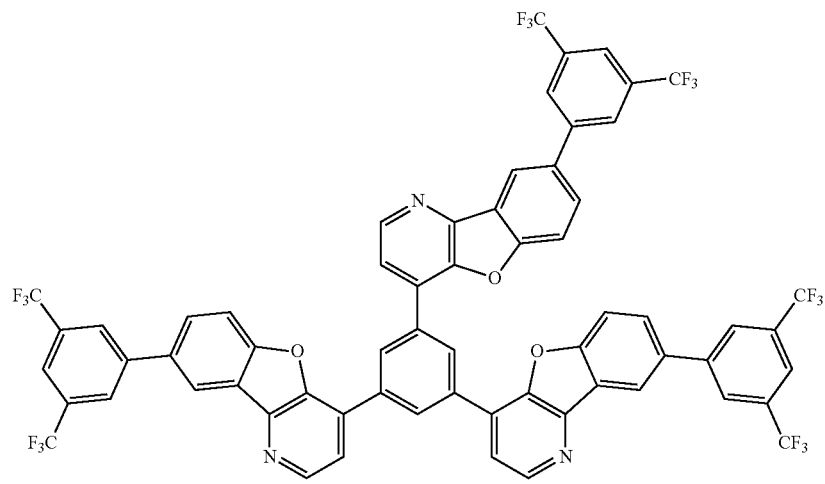

M-359

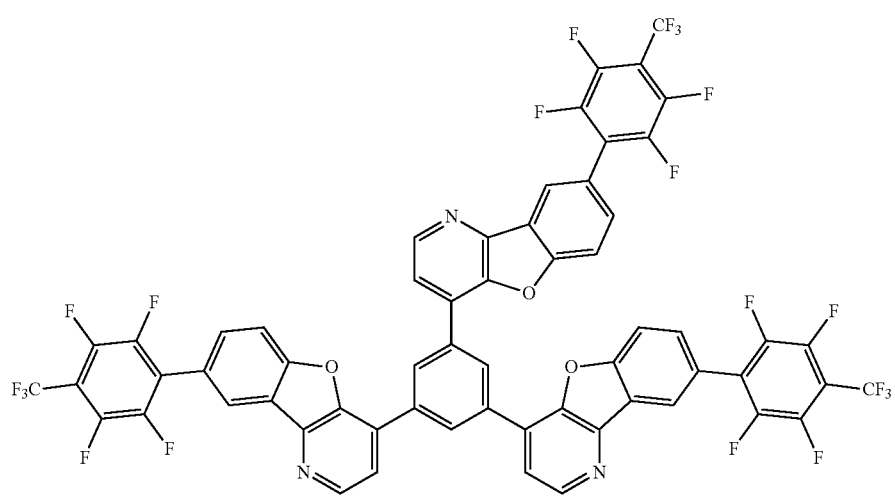

<<Layer Structure of Organic EL Element>>

The layer structure of the organic EL element of the present invention will now be described. Preferable examples of the layer structure of the various organic functional layers sandwiched between the anode and the cathode in the organic EL element of the present invention are shown below. However, the present invention is not limited to these examples.

(i) Anode/light-emitting layer unit/electron transport layer/cathode (ii) Anode/hole transport layer/light-emitting layer unit/electron transport layer/cathode (iii) Anode/hole transport layer/light-emitting layer unit/hole blocking layer/electron transport layer/cathode (iv) Anode/hole transport layer/light-emitting layer unit/hole blocking layer/electron transport layer/cathode buffer layer/cathode (v) Anode/anode buffer layer/hole transport layer/light-emitting layer unit/hole blocking layer/electron transport layer/cathode buffer layer/cathode In addition, the light-emitting layer unit may include a non-luminous intermediate layer between a plurality of light-emitting layers. The light-emitting layer unit may also have a multiphoton unit structure in which the intermediate layer is a charge generating layer. In this case, examples of the charge generating layer include inorganic layers composed of conductive inorganic compounds, such as indium-tin oxide (ITO), indium-zinc oxide (IZO), $ZnO_2$, TiN, ZrN, HfN, TiOx, VOx, CuI, InN, GaN, $CuAlO_2$, $CuGaO_2$, $SrCu_2O_2$, $LaB_6$, and $RuO_2$; double-layer films, such as $Au/Bi_2O_3$ films; multi-layer films, such as $SnO_2/Ag/SnO_2$, ZnO/Ag/ZnO, $Bi_2O_3/Au/Bi_2O_3$, $TiO_2/TiN/TiO_2$, and $TiO_2/ZrN/TiO_2$ films; and organic layers composed of conductive organic compounds, such as fullerenes (such as $C_{60}$), oligothiophene, metal phthalocyanines, metal-free phthalocyanines, metal porphyrins, and metal-free porphyrins.

In the organic EL element of the present invention, the light-emitting layer is preferably a white-light-emitting layer, and a lighting device using such a white-light-emitting layer is preferred.

The individual layers constituting the organic EL element of the present invention will now be described.

<<Organic Functional Layer>>

The organic EL element of the present invention comprises an anode, a plurality of organic functional layers including a light-emitting layer, and a cathode in that order. The organic functional layer according to the present invention is characterized by being positioned between the anode and the cathode.

The organic EL element of the present invention comprises a plurality of organic functional layers, and those organic functional layers include a light-emitting layer. The light-emitting layer may be one layer or a plurality of layers.

Further, the organic functional layer is preferably a layer containing the above-mentioned compound having a structure represented by the general formula (1) and an electron injection material. More specifically, it is also preferable for a compound having a structure represented by the general formula (1) to be contained in the electron injection layer.

In addition, it is also preferable for the organic functional layer containing the compound having a structure represented by the general formula (1), the electron injection layer containing an electron injection material, and the cathode to be stacked in that order.

<<Light-Emitting Layer>>

The light-emitting layer according to the present invention emits light through the recombination of electrons and holes, which are injected from the electrodes or the electron transport layer and hole transport layer. The site of light emission may be the interior of the light-emitting layer or the interface between the light-emitting layer and an adjoining layer.

The total thickness of the light-emitting layer is not particularly limited, but from the viewpoint of film uniformity, preventing application of an unnecessarily high voltage during light emission, and improving the stability of emitted colors based on the drive current, the total thickness is preferably in the range of 2 nm to 5 μm, more preferably in the range of 2 to 200 nm, and particularly preferably in the range of 5 to 100 nm.

The light-emitting layer can be deposited and formed using the light-emitting dopant and host compound (described below) by, for example, a vacuum vapor deposition method or a wet method (also referred to as a wet process; for example, spin coating, casting, die coating, blade coating, roll coating, inkjet printing, printing, spray coating, curtain coating, and Langmuir Blodgett (LB) coating), and the like.

The light-emitting layer of the organic EL element of the present invention preferably contains a light-emitting dopant (phosphorescence emitting dopant, fluorescence emitting dopant, etc.) compound and a host compound.

(1) Light-Emitting Dopant

The light-emitting dopant (also referred to as light-emitting dopant, dopant compound, or simply as dopant) will now be described.

As the light-emitting dopant, a fluorescent emitting dopant (also referred to as fluorescence dopant, fluorescent compound, fluorescence emitting compound), a phosphorescence emitting dopant (also referred to as phosphorescent dopant, phosphorescence compound, phosphorescence emitting compound, etc.) can be used.

(1.1) Phosphorescent Dopant

A phosphorescent dopant is a compound from which emission from the excited triplet state is measured. Specifically, a phosphorescent dopant is defined as a compound emitting phosphorescent light at room temperature (25° C.) and having a phosphorescent quantum yield of 0.01 or more at 25° C. A preferred phosphorescent quantum yield is 0.1 or more.

The phosphorescent quantum yield is determined by the method described on page 398 of *Bunko II of Jikken Kagaku Koza* 7 (Spectroscopy II, Experimental Chemistry 7) (4th Edition, 1992, published by Maruzen). The phosphorescent quantum yield in a solution can be determined using various solvents, but the phosphorescent dopant used in the present invention has the above-mentioned phosphorescent quantum yield (0.01 or more) in any arbitrary solvent.

There are two types of light emission mechanisms for phosphorescent dopants. One is energy-transfer emission, in which carriers transported to the host compound are recombined therein to excite the light-emitting host compound, and the energy of the excited light-emitting host compound is transferred to the phosphorescent dopant to emit light from the phosphorescent dopant. The second type is carrier-trap emission, in which the phosphorescent dopant serves as a carrier trap to recombine carriers on the phosphorescent dopant, whereby light is emitted from phosphorescent dopant. In both cases, the excitation energy of the phosphorescent dopant should be lower than the excitation energy of the host compound.

(1.2) Fluorescent Dopant

Examples of fluorescent dopants include coumarin dyes, pyran dyes, cyanine dyes, croconium dyes, squarylium dyes, oxobenzanthracene dyes, fluorescein dyes, rhodamine dyes, pyrylium dyes, perylene dyes, stilbene dyes, polythiophene dyes, fluorescent rare earth element complexes, and compounds having high fluorescent quantum yields, represented by laser dyes.

[Combined Use with Conventionally-Known Dopants]

Further, the light-emitting dopant used in the present invention may be used in combination with a plurality of types of compounds, and may also be used by combining phosphorescent dopants having different structures or by combining a phosphorescent dopant and a fluorescent dopant.

As the light-emitting dopant, the conventionally known compounds described in International Publication No. WO 2013/061850 can be suitably used, but the present invention is not limited thereto.

[Host Compound]

The host compound (also referred to as a light-emitting host, a light-emitting host compound) that can be used in the present invention has a mass ratio in the light-emitting layer of 20% or more of the compounds contained in the layer.

The host compound is defined as a compound having a phosphorescent quantum yield of phosphorescence at room temperature (25° C.) of less than 0.1. Preferably, the phosphorescent quantum yield is less than 0.01. Further, among the compounds contained in the light-emitting layer, the mass ratio of the host compound in the layer is preferably 20% or more.

The host compound that can be used in the present invention is not particularly limited, and compounds conventionally used in organic EL elements can be used. Representative examples include compounds having a basic skeleton of a carbazole derivative, a triarylamine derivative, an aromatic derivative, a nitrogen-containing heterocyclic compound, a thiophene derivative, a furan derivative, an oligoarylene compound, and the like, or a carboline derivative or a diazacarbazole derivative (here, diazacarbazole derivative refers to a compound in which one of the carbon atoms of the hydrocarbon ring constituting the carboline ring is replaced with a nitrogen atom), and the like.

As a known host compound which can be used in the present invention, a compound that is capable of transporting holes and electrons, that prevents a lengthening in the emission wavelength, and that has a high Tg (glass transition temperature) is preferable.

Further, in the present invention, conventionally known host compounds may be used alone or in combination of a plurality of kinds. Using a plurality of kinds of host compound enables charges movement to be adjusted and the efficiency of the organic EL element to be increased. In addition, by using a plurality of conventionally known compounds, different emissions can be mixed, which enables arbitrary emission colors to be obtained.

The host compound used in the present invention may be a low molecular weight compound or a polymer compound having a repeating unit. The host compound used in the present invention may even be a low molecular weight compound (polymerizable host compound) having a polymerizable group such as a vinyl group or an epoxy group, and one kind or a plurality of kinds of such compounds may be used.

Specific examples of known host compounds include the compounds described in the following documents.

Japanese Patent Laid-Open Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

<<Cathode>>

For the cathode, a metal (referred to as electron injecting metal), an alloy, or a conductive compound having a small work function (4 eV or less), or a mixture thereof is used as an electrode substance. Specific examples of such an electrode substance include sodium, sodium-potassium alloys, magnesium, lithium, mixtures of magnesium/copper, mixtures of magnesium/silver, mixtures of magnesium/aluminum, mixtures of magnesium/indium, mixtures of aluminum/aluminum oxide ($Al_2O_3$), indium, mixtures of lithium/aluminum, and rare earth element metals. Among these, from the viewpoints electron injection properties and durability against oxidation and the like, preferred are mixtures of electron injecting metals and stable second metals having a larger work function, such as mixtures of magnesium/silver, mixtures of magnesium/aluminum, mixtures of magnesium/indium, mixtures of aluminum/aluminum oxide (Al$_2$O$_3$), mixtures of lithium/aluminum, aluminum, and the like.

In particular, it is preferable that silver be contained as a main component. Examples of alloys containing silver as a main component include silver magnesium (AgMg), silver copper (AgCu), silver palladium (AgPd), silver palladium copper (AgPdCu), silver indium (AgIn), and the like.

In the present invention, "main component" means the content of that component is 50% by mass or more in the film or layer, preferably 80% by mass or more, and more preferably 90% by mass or more.

The cathode using an alloy containing silver as a main component may have a structure in which the cathode is stacked by optionally dividing it into a plurality of layers.

The cathode has a thickness selected in the range of usually 10 nm to 5 µm, and preferably 50 to 200 nm. In the case of using an alloy containing silver as a main component, the thickness is preferably 15 nm or less, and preferably in the range of 4 to 12 nm. When the thickness is within the above range, the amount of light components that are absorbed or reflected by the film can be reduced, light transmittance can be maintained, and the conductivity of the layer can be ensured.

As described above, when the cathode contains silver as a main component, it is preferable for the cathode to be adjacent to the organic functional layer containing the compound having a structure represented by the general formula (1).

The organic functional layer containing the compound having a structure represented by the general formula (1) is preferably adjacent to the cathode, and even when the cathode is formed on the organic functional layer, the organic functional layer may be formed on the cathode. Further, the cathode may be formed on the organic functional layer, an organic functional layer may be formed on the cathode, and the cathode may be sandwiched between two organic functional layers.

When depositing a cathode mainly composed of silver on an upper portion of the organic functional layer, the silver atoms constituting the cathode interact with the compound having a structure represented by the general formula (1) contained in a metal affinity layer, the diffusion distance of the silver atoms on the surface of the organic functional layer decreases, and agglomeration (migration) of silver at a specific site can be suppressed.

More specifically, the silver atoms are deposited by undergoing layered growth (Frank-van der Merwe: FM growth) in which the silver atoms first form two-dimensional cores on the surface of the organic functional layer, which has an atom with an affinity for silver atoms, and then a two-dimensional single crystal layer is formed around the cores.

In general, it is thought that the silver atoms adhered to the surface of the organic functional layer tend to be deposited in an island-like manner by undergoing island-type growth (Volumer-Weber growth: VW growth) in which the silver atoms bind together while their surfaces spread out to form three-dimensional cores, which grow into three-dimensional islands.

However, in the present invention, it is presumed that the island-like growth is suppressed and the layered growth is promoted by the compound having a structure represented by the general formula (1) contained in the organic functional layer.

Therefore, it is possible to obtain a cathode of uniform thickness even at a thin thickness. Consequently, it is possible to obtain a transparent electrode ensuring conductivity while maintaining optical transparency as a result of its thin thickness.

In addition, when the organic functional layer is deposited on an upper portion of the cathode, it is thought that the silver atoms constituting the cathode interact with atoms having an affinity for silver atoms contained in the organic functional layer, thereby suppressing mobility. This improves the surface smoothness of the cathode, which enables irregular reflection to be suppressed and improves light transmittance.

Through such interactions, it is believed that changes in the film quality of cathode in response to physical stimuli such as heat and temperature can be suppressed, and durability can be improved.

The cathode can be prepared by forming a thin film from, in addition to an alloy containing silver as a main component, ordinary electrode substances, by a method such as vapor deposition, sputtering, or the like. The cathode preferably has a sheet resistance value of several hundred n/sq. or less, and particularly preferably 25 n/sq. or less.

In order to transmit the emitted light, if either the anode or the cathode of the organic EL element is transparent or translucent, emission luminance is improved, which is favorable. The cathode preferably has a light transmittance of 50% or more.

Further, a transparent or translucent cathode can be prepared by forming the above-mentioned metal on the cathode to a thickness of 1 to 20 nm, and then forming a conductive transparent material (described below in the explanation of the anode) thereon. By applying such a cathode, it is possible to prepare elements in which both the anode and the cathode are transparent.

<<Electron Transport Layer>>

The electron transport layer is composed of a material having a function of transporting electrons, and as described above, preferably contains a compound having a structure represented by the general formula (1). In a broad sense, the electron injection layer and the hole blocking layer are included in the term electron transport layer. The electron transport layer can have a single layer or multi-layer structure. In addition, an electron injection and transport layer also containing the material included in the electron injection layer (described later) may be provided.

The electron transport layer transfers electrons injected from the cathode to the light-emitting layer. As the constituent material for the electron transport layer, any material can be selected from known compounds. These compounds can also be used in combination.

Examples of conventionally known materials for the electron transport layer (hereinafter, referred to as electron transport material) include polycyclic aromatic hydrocarbons, such as nitro-substituted fluorene derivatives, diphenylquinone derivatives, thiopyran dioxide derivatives, naphthalene, and perylene; heterocyclic tetracarboxylic anhydrides; carbodiimide; fluorenylidenemethane derivatives; anthraquinodimethane and anthrone derivatives; oxadiazole derivatives; derivatives with a ring structure such as carboline derivatives or carboline derivatives having carboline rings in which at least one of carbon atoms of the hydrocarbon ring is replaced with a nitrogen atom; hexaazatriphenylene derivatives; and the like.

Further, in the above-mentioned oxadiazole derivative, a thiadiazole derivative in which the oxygen atom of the oxadiazole ring is replaced with a sulfur atom, and a quinoxaline derivative having a quinoxaline ring known as an electron withdrawing group can also be used as an electron transport material.

Polymer materials containing these materials in their polymer chains or having main chains composed of these materials can also be used.

Further, the following electron transport materials can also be used: metal complexes of 8-quinolinol derivatives, such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, and bis(8-quinolinol)zinc (Znq), or these metal complexes in which the central metal has been replaced with In, Mg, Cu, Ca, Sn, Ga, or Pb.

In addition, metal-free or metal phthalocyanine or phthalocyanines having an alkyl or sulfonate group at their terminals can also be used as the electron transport material.

Further, inorganic semiconductors, such as n-type Si and n-type SiC, can also be used as the electron transport material.

The electron transport layer can preferably be formed by forming a thin film from the electron transport material by a vacuum vapor deposition method or a wet method (also referred to as a wet process; for example, spin coating, casting, die coating, blade coating, roll coating, inkjet printing, printing, spray coating, curtain coating, and Langmuir Blodgett (LB) coating), and the like.

The thickness of the electron transport layer is not particularly limited, but is usually about 5 to 5000 nm, and preferably 5 to 200 nm. The electron transport layer may also have a single layer structure composed of one kind or two or more kinds of the above-mentioned materials.

Further, the electron transport layer may be doped with an n-type dopant such as a metal complex or a metal compound such as a metal halide.

Examples of conventionally known electron transport materials that can be preferably used for forming the electron transport layer of the organic EL element of the present invention include, but are not limited to, the compounds described in International Publication No. WO 2013/061850.

<<Injection layer: Electron Injection Layer (Cathode Buffer Layer) and Hole Injection Layer>>

An injection layer is optionally provided. Examples thereof include an electron injection layer and a hole injection layer. An injection layer may be provided between the anode and the light-emitting layer or hole transport layer, and between the cathode and the light-emitting layer or electron transport layer.

The injection layer is a layer provided between the electrode and the organic functional layer in order to lower the drive voltage and to improve the emission luminance, and is described in detail in chapter 2, "Electrode Materials" (pages 123 to 166) of the second edition of "*Yuki EL Soshi to Sonokougyouka Saizensen*" (Organic EL Elements and Their Industrial Application Frontiers) (Nov. 30, 1998, published by NTS). Examples include a hole injection layer (anode buffer layer) and an electron injection layer (cathode buffer layer).

The anode buffer layer (hole injection layer) is described in detail in Japanese Patent Laid-Open Nos. 9-45479, 9-260062, and 8-288069. Specific examples thereof include phthalocyanine buffer layers represented by copper phthalocyanine; the hexaazatriphenylene derivative buffer layers described in National Publication of International Patent Application No. 2003-519432 and Japanese Patent Laid-Open No. 2006-135145; oxide buffer layers represented by vanadium oxide; amorphous carbon buffer layers; polymer buffer layers using a conductive polymer, such as polyaniline (emeraldine) and polythiophene; orthometalated complex layers represented by such as a tris(2-phenylpyridine) iridium complex; and the like.

The cathode buffer layer (electron injection layer) is described in detail in Japanese Patent Laid-Open Nos. 6-325871, 9-17574, and 10-74586, and the like. Specific examples thereof include metal buffer layers represented by strontium and aluminum; alkali metal compound buffer layers represented by lithium fluoride and potassium fluoride; alkaline earth metal compound buffer layers represented by magnesium fluoride and cesium fluoride; and oxide buffer layers represented by aluminum oxide. The buffer layer (injection layer) is desirably a very thin film. The thickness of the buffer layer depends on the material, but preferably ranges from 0.1 nm to 5 μm.

<<Blocking Layer: Hole Blocking Layer and Electron Blocking Layer>>

The blocking layer is an optional layer provided in addition to the basic structure layers of the organic compound thin film as described above. Examples of the blocking layer include the hole blocking layers described in Japanese Patent Laid-Open Nos. 11-204258 and 11-204359, and on page 237 of "*Yuki EL Soshi to Sonokougyouka Saizensen*" (Organic EL Elements and Their Industrial Application Frontiers) (Nov. 30, 1998, published by NTS).

In a broad sense, the hole blocking layer is composed of a hole blocking material having a function of an electron transport layer and a significantly low ability of transporting holes while having a function of transporting electrons. Such a hole blocking layer can increase the recombination probability of electrons and holes by blocking holes while transporting electrons.

Further, the electron transport layer structure can optionally be used as a hole blocking layer.

It is preferable to provide the hole blocking layer of the organic EL element of the present invention adjacent to the light-emitting layer.

The hole blocking layer preferably contains the carbazole derivatives, carboline derivatives, or diazacarbazole derivatives (here, diazacarbazole derivative refers to a compound in which one of the carbon atoms constituting the carboline ring is replaced with a nitrogen atom) mentioned above as examples of the host compound.

On the other hand, in a broad sense, the electron blocking layer is composed of a material having a function of a hole transport layer and a significantly low ability of transporting electrons while having a function of transporting holes. Such an electron blocking layer can increase the recombination probability of electrons and holes by blocking electrons while transporting holes.

Further, the hole transport layer structure (described later) can optionally be used as an electron blocking layer. The thickness of the hole blocking layer and the electron transport layer according to the present invention is preferably 3 to 100 nm, and more preferably 5 to 30 nm.

<<Hole Transport Layer>>

The hole transport layer is composed of a hole transport material capable of transporting holes, and in a broad sense, includes the hole injection layer and the electron blocking layer. The hole transport layer can have a single-layer or multi-layer structure.

The hole transport material can be an organic or inorganic substance that is capable of injecting holes, transporting holes, or blocking electrons. Examples thereof include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, and conductive higher oligomers, particularly thiophene oligomers.

The azatriphenylene derivatives described in National Publication of International Patent Application No. 2003-519432 and Japanese Patent Laid-Open No. 2006-135145 can also be similarly used as the hole transport material.

Although the above-mentioned compounds can be used as the hole transport material, it is preferable to use a porphyrin compound, an aromatic tertiary amine compound, and a styrylamine compound, and particularly preferable is an aromatic tertiary amine compound.

Representative examples of aromatic tertiary amine compounds and styrylamine compounds include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino) quadriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostilbene; N-phenylcarbazole; compounds having two fused aromatic rings in the molecule described in U.S. Pat. No. 5,061,569, such as 4,4'-bis[N-(1-naphthyl)-N-phenylamino]biphenyl (NPD); compounds having three triphenylamine units linked in a star burst form described in Japanese Patent Laid-Open No. 4-308688, such as 4,4',4"-tris[N-(3-methylphenyl)-N-phenylamino]triphenylamine (MTDATA).

In addition, polymer materials having these materials in their polymer chains or having main chains mainly composed of these materials can also be used.

Further, inorganic compounds, such as p-type Si and p-type SiC, can also be used as the hole injection material and the hole transport material.

The so-called p-type hole transport materials described in Japanese Patent Laid-Open No. 11-251067 and a document written by J. Huang et al. (Applied Physics Letters 80 (2002), p. 139) can also be used. In the present invention, it is preferable to use these materials as they enable a light-emitting element having higher efficiency to be obtained.

The hole transport layer can be formed by forming the hole transport material into a thin film by any known method, such as vacuum vapor deposition, spin coating, casting, printing including inkjet printing, and a LB method. The thickness of the hole transport layer is not particularly limited, but is usually about 5 nm to 5 µm, and preferably 5 to 200 nm. The hole transport layer may have a single-layer structure composed of one kind or two or more kinds of the materials described above.

Further, a hole transport layer doped with an impurity to enhance p-properties can also be used. Examples thereof include the hole transport layers described in Japanese Patent Laid-Open Nos. 4-297076, 2000-196140, and 2001-102175, and J. Appl. Phys., 95, 5773(2004).

In the present invention, it is preferable to use such a hole transport layer having enhanced p-properties because an element having lower power consumption can be prepared.

<<Anode>>

As the anode of the organic EL element, it is preferable to use a metal, an alloy, or a conductive compound having a large work function (4 eV or more), or a mixture thereof as an electrode substance. Specific examples of such an electrode substance include a metal such as Au; a conductive transparent material such as CuI, ITO, $SnO_2$, ZnO, and the like.

Further, a material capable of forming into an amorphous transparent conductive film, such as IDIXO ($In_2O_3$—ZnO), can also be used. The anode can be prepared by forming a thin film from these electrode substances by a method such as vapor deposition or sputtering, and patterning into a desired shape by photolithography. If a high-precision pattern is not required (about 100 µm or more), the pattern may be formed through a mask having the desired shape during vapor deposition or sputtering of the electrode substance.

Further, when using a coatable substance, such as a conductive organic compound, a wet deposition method, such as printing or coating, may be used. When extracting the emission light from the anode, it is desirable to have a light transmittance of more than 10%. The anode preferably has a sheet resistance value of several hundred n/sq. or less. In addition, although the thickness depends on the material, it is selected in the range of usually 10 to 1000 nm, and preferably 10 to 200 nm.

<<Support Substrate>>

Any support substrate (hereinafter, also referred to as base, substrate, base material, support, etc.) can be used in the organic EL element of the present invention. The substrate can be composed of any material, such as glass or plastics, without particular limitation, and may be transparent or opaque. In the case extracting light from the support substrate side, a transparent support substrate is preferable. Preferable examples of the material for the transparent support substrate include glass, quartz, and transparent resin films. Particularly preferable are resin films which can give flexibility to the organic EL element.

Examples of such a resin film include films of polyesters, such as poly(ethylene terephthalate) (PET) and poly(ethylene naphthalate) (PEN); polyethylene; polypropylene; cellophane; cellulose esters, such as cellulose diacetate, cellulose triacetate (TAC), cellulose acetate butyrate, cellulose acetate propionate (CAP), cellulose acetate phthalate, and cellulose nitrate, and their derivatives; poly(vinylidene chloride); poly(vinyl alcohol); poly(ethylene-vinyl alcohol); syndiotactic polystyrene; polycarbonates; norbornene resins; polymethylpentene; polyether ketones; polyimides; polyether sulfones (PESs); poly(phenylene sulfide); polysulfones; polyether imides; polyether ketone imides; polyamides; fluorinated resins; nylons; poly(methylmethacrylate); acrylates or polyarylates; and cycloolefin resins, such as ARTON (trade name, manufactured by JSR Corporation) or APEL (trade name, manufactured by Mitsui Chemicals, Inc.).

The surface of the resin film can be coated with an inorganic or organic coating film or with hybrid coating film thereof. Such a coating film is preferably a gas barrier film having a water vapor permeation rate (25±0.5° C., relative humidity (90±2)% of 0.01 $g/m^2 \cdot 24$ h or less determined by a method in conformity with JIS K 7129-1992, and more preferably a high gas barrier film having an oxygen permeation rate of $1\times10^{-3}$ $mL/m^2 \cdot h \cdot atm$ or less and a water vapor permeation rate of $1\times10^{-5}$ g/m$^2$·24 h or less, which are determined by a method in conformity with JIS K 7126-1987.

The gas barrier layer can be composed of any material having a function of suppressing the entry of substances that degrade the element, such as moisture or oxygen. Usable materials for the gas barrier layer are silicon oxide, silicon dioxide, and silicon nitride, for example. To improve the brittleness of the film, the gas barrier layer more preferably has a laminate structure of such an inorganic layer and an organic layer composed of an organic material. The stacking order of the inorganic layer and the organic functional layer is not particularly limited, but it is preferable to alternately stack such an inorganic layer and organic layer a plurality of times.

The method for forming the gas barrier layer is not particularly limited, and for example, a method such as vacuum vapor deposition, sputtering, reactive sputtering, molecular beam epitaxy, cluster ion beam, ion plating, plasma polymerization, atmospheric-pressure plasma polymerization, plasma chemical vapor deposition (CVD), laser CVD, thermal CVD, and coating. It is particularly preferable to employ the atmospheric-pressure plasma polymerization method described in Japanese Patent Laid-Open No. 2004-68143.

Examples of opaque support substrates include metal plates composed of aluminum, stainless steel, or the like; films; opaque resin substrates; ceramic substrates; and the like.

The organic EL element of the present invention preferably has an external light extraction efficiency at room temperature of 1% or more, and more preferably 5% or more.

Here, external extraction quantum yield (%)={(number of photons emitted to the outside of organic EL element)/(number of electrons flowing into organic EL element)}×100.

The substrate may be used together with a color hue improving filter and the like, such as a color filter, or with a color converting filter for converting the color of light emitted from the organic EL element in various colors by using a fluorescent substance. When a color converting filter is used, it is preferable for the emission light of the organic EL element to have λmax of 480 nm or less.

<<Method of Preparing Organic EL Element>>

There is now described, as an example of the method of preparing the organic EL element, a method of preparing an element composed of an anode/a hole injection layer/a hole transport layer/a light-emitting layer/a hole blocking layer/an electron transport layer/a cathode buffer layer (electron injection layer)/and a cathode.

First, a thin film composed of the desired electrode substance, for example, an anode substance, is formed on a suitable substrate to a thickness of 1 µm or less, and preferably 10 to 200 nm, to prepare an anode.

Next, a thin film containing an organic compound of the hole injection layer, the hole transport layer, the light-emitting layer, the hole blocking layer, the electron transport layer, the cathode buffer layer or the like, which are the element materials, is formed thereon.

The thin film can be formed by, for example, depositing a film by a vacuum vapor deposition method or a wet method (also referred to as a wet process).

Examples of the wet method include spin coating, casting, die coating, blade coating, roll coating, inkjet printing, printing, spray coating, curtain coating, and LB coating. Preferred are methods suitable for a roll-to-roll process, such as die coating, roll coating, inkjet printing, and spray coating, which can form precise thin films with a high productivity. A different deposition method may be used for each layer.

Examples of solvents that the organic EL materials, such as a light-emitting dopant, used in the present invention are dissolved or dispersed in include: ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexyl benzene; aliphatic hydrocarbons, such as cyclohexane, decalin, and dodecane; and organic solvents, such as dimethylformamide (DMF) and DMSO.

Further, those materials can be dispersed by dispersion methods such as ultrasonic waves, high shear force dispersion, or media dispersion.

After these layers are formed, the cathode is provided by forming a thin film composed of the substance for the cathode on those layers to a thickness in the range of 1 µm or less, and preferably 50 to 200 nm, whereby the desired organic EL element is obtained.

Further, an organic EL element can also be prepared in the reverse order, that is, by arranging, in order, a cathode, a cathode buffer layer, an electron transport layer, a hole blocking layer, a light-emitting layer, a hole transport layer, a hole injection layer, and an anode.

Although it is preferable to prepare the organic EL element of the present invention by forming the layers from the hole injection layer to the cathode in a single vacuum operation, the element may be removed from the apparatus midway through the process and be subjected to a different deposition process. At such a time, it is preferable to carry out the work under a dry inert gas atmosphere.

<<Sealing>>

Examples of the sealing method used in the present invention include bonding an electrode and a support substrate to a sealing member with an adhesive.

The sealing member is arranged so as to cover the display region of the organic EL element, and may be a recessed plate or a flat plate. The sealing member may be transparent and have electrical insulation properties.

Specific examples thereof include glass plates, polymer plates and films, metal plates and films, and the like. Examples of glass plates include soda lime glass, glass containing barium or strontium, lead glass, aluminosilicate glass, borosilicate glass, barium borosilicate glass, quartz, and the like.

Examples of polymer plates include plates composed of a polycarbonate, an acrylic, polyethylene terephthalate, a polyether sulfide, a polysulfone, and the like.

Examples of metal plates include plates composed of one or more metals selected from the group consisting of stainless steel, iron, copper, aluminum, magnesium, nickel, zinc, chromium, titanium, molybdenum, silicon, germanium, and tantalum, and alloys thereof.

In the present invention, because a thin element can be obtained, it is preferable to use a polymer film or a metal film.

In addition, the polymer film preferably has an oxygen permeation rate of $1\times10^{-3}$ ml/m$^2$·24 h·atm or less determined by a method in conformity with JIS K 7126-1987 and a water vapor permeation rate (25±0.5° C., relative humidity (90±2)% of $1\times10^{-3}$ g/m$^2$·24 h or less determined by a method in conformity with JIS K 7129-1992.

A processing for recessing the sealing member is carried out by sand blasting, chemical etching, or the like.

Specific examples of the adhesive include photocurable or thermosetting adhesives having reactive vinyl groups, such as adhesives of oligomers of acrylic acid and methacrylic acid; moisture-curable adhesives, such as 2-cyanoacrylate ester adhesives; and the like. Other examples include thermally or chemically curable (two-component) adhesives, such as epoxy adhesives. Further examples include hot-melt polyamides, polyesters, and polyolefins. Examples also include cationic, ultraviolet light-curable epoxy resin adhesives.

Because the organic EL element may be degraded by a heat treatment, the adhesive is preferably curable at a temperature from room temperature to 80° C. The adhesive may contain a desiccant dispersed therein. The adhesive can be applied onto the sealing portion by using a commercially available dispenser, or printed like screen printing.

Further, a sealing film composed of a layer of an inorganic substance and a layer of an organic substance can also be suitably arranged sandwiching the organic functional layer so as to cover the electrode and the organic functional layer on the outer side of the electrode on the side facing the support substrate and to be in contact with the support substrate. In this case, the sealing film can be composed of any material which suppresses the entry of substances degrading the organic EL element, such as moisture or oxygen. Usable materials are silicon oxide, silicon dioxide, and silicon nitride, for example.

In addition, to improve the brittleness of the sealing film, the sealing film preferably has a laminate structure of such an inorganic layer and an organic layer composed of an organic material. The sealing film can be formed by any method, such as vacuum vapor deposition, sputtering, reactive sputtering, molecular beam epitaxy, cluster ion beam, ion plating, plasma polymerization, atmospheric-pressure plasma polymerization, plasma CVD, laser CVD, thermal CVD, and coating.

The space between the sealing member and the display region of the organic EL element preferably contains, in a gas phase or a liquid phase, an inert gas such as nitrogen and argon, or an inert liquid such as fluorohydrocarbon and silicone oil. The space can be a vacuum. A moisture absorbing compound can also be encapsulated in the space.

Examples of the moisture absorbing compound include metal oxides (e.g., sodium oxide, potassium oxide, calcium oxide, barium oxide, magnesium oxide, and aluminum oxide), sulfuric acid salts (e.g., sodium sulfate, calcium sulfate, magnesium sulfate, and cobalt sulfate), metal halides (e.g., calcium chloride, magnesium chloride, cesium fluoride, tantalum fluoride, cerium bromide, magnesium bromide, barium iodide, and magnesium iodide), perchloric acids (e.g., barium perchlorate and magnesium perchlorate). It is preferable to use an anhydride of a sulfuric acid salt, a metal halide, or a perchloric acid.

<<Protective Film and Protective Plate>>

A protective film or plate may be arranged sandwiching the organic functional layer and on the outer side of the sealing film, or film for sealing, on the side facing the support substrate to enhance the mechanical strength of the element. In particular, when sealing is performed by such a sealing film, because the mechanical strength may not necessarily be high, it is preferable to provide such a protective film or plate. Materials usable in the protective film or plate are the same glass plates, polymer plates and films, and metal plates and films and the like as those used for sealing. However, from the viewpoint of reducing weight and obtaining a thinner film, a polymer film is preferable.

<<Light Extraction>>

Organic EL elements emit light from inside a layer having a higher refractive index (refractive index of about 1.7 to 2.1) than that of air. It is said that, in general, only about 15% to 20% of the light emitted by the light-emitting layer is extracted. Such a low level of light extraction is due to: the light incident on the interface (interface between transparent substrate and air) at an angle θ equal to or larger than a critical angle being totally reflected, and unable to be extracted outside the element; and the light between the transparent electrode or the light-emitting layer and the transparent substrate being totally reflected and guided through the transparent electrode or the light-emitting layer, escaping toward the sides of the element.

Examples of methods for improving the light extraction efficiency include a method of forming irregularities on a transparent substrate surface to prevent total reflection of light at the interface between the transparent substrate and air (U.S. Pat. No. 4,774,435), a method of improving the efficiency by imparting light condensing properties to the substrate (Japanese Patent Laid-Open No. 63-314795), a method of forming reflective surfaces on the side faces of the element or the like (Japanese Patent Laid-Open No. 1-220394), a method of forming an anti-reflective film by introducing a flat layer having an intermediate refractive index between the substrate and the light-emitting body (Japanese Patent Laid-Open No. 62-172691), a method of introducing, between the substrate and the light-emitting body, a flat layer having a refractive index less than that of the substrate (Japanese Patent Laid-Open No. 2001-202827), and a method of forming a diffraction grating between any of the substrate, the transparent electrode layer, and the light-emitting layer (including between the substrate and the outside) (Japanese Patent Laid-Open No. 11-283751).

In the present invention, these methods can be used in combination with the organic EL element of the present invention. However, it is preferable to arrange, between the substrate and light-emitting body, a flat layer having a refractive index lower than the substrate, or to arrange a diffraction grating between any of the substrate, the transparent electrode layer, and the light-emitting layer (including between the substrate and the outside).

In the present invention, an element having even higher luminance or excellent durability can be obtained by combining these measures.

When a low-refractive-index medium thicker than the wavelength of light is formed between a transparent electrode and a transparent substrate, the light emitted from the transparent electrode is extracted more efficiently the lower the refractive index of the medium is.

Examples of the low-refractive-index layer include a layer of aerogel, porous silica, magnesium fluoride, and a fluorine polymer. Since the transparent substrate usually has a refractive index of about 1.5 to 1.7, the low-refractive-index layer preferably has a refractive index of about 1.5 or less, and more preferably a refractive index of 1.35 or less.

The thickness of the low-refractive-index medium is desirably twice or more the wavelength in the medium. This is because the effect of the low-refractive-index layer is reduced when the thickness of the low-refractive-index medium is about the wavelength of light and the electromagnetic waves emitted by evanescence enter the substrate.

The method of introducing a diffraction grating into the interface causing total reflection or into any of the media has the characteristic that the improvement in light extraction efficiency is high. In this method, utilizing the property that the diffraction grating can change the direction of the light to a specific direction different from the refraction by so-called Bragg diffraction, namely, first order diffraction or second order diffraction, the light that is generated from the light-emitting layer but cannot be extracted outside due to total reflection between the layers and the like can be diffracted by introducing a diffraction grating between any of the layers or in the media (in the transparent substrate or in the transparent electrode), whereby light is extracted to the outside.

It is desirable that the diffraction grating to be introduced have a two-dimensional periodic refractive index. This is because the light emitted by the light-emitting layer is randomly produced in every direction, so for a typical one-dimensional diffraction grating having a periodic refractive index distribution only in a certain direction, only light traveling in a specific direction is diffracted, and the light extraction efficiency does not rise much.

However, by making the refractive index distribution be two-dimensionally distributed, light traveling in every direction is diffracted, and the light extraction efficiency is increased.

As described above, the position where the diffraction grating is to be introduced may be a position between any of the layers or in the media (in the transparent substrate or in the transparent electrode), but it is desirable to introduce the diffraction grating in the vicinity of the organic light-emitting layer, which is where light is generated.

At this time, the period of the diffraction grating is preferably about half to triple the wavelength of the light inside the medium.

The array of the diffraction grating is preferably a two-dimensional repeating array, such as a square lattice, a triangular lattice, or a honeycomb lattice.

<<Light Condensing Sheet>>

In the organic EL element of the present invention, the luminance in a specific direction can be enhanced by processing to provide, for example, a microlens array-like structure on the light extraction side of the substrate or combination with a so-called light-condensing sheet to condense light on the front of the light-emitting surface of the element.

As an example of the microlens array, quadrangular pyramids having sides of 30 μm and an apex angle of 90° are arranged two-dimensionally on the light extraction side of the substrate. One side is preferably 10 to 100 μm. If the sides are smaller than this, colors are produced due to a diffraction effect, and if the sides are larger than this, the thickness of the microlens is too thick, which is not preferable.

Examples of usable light-condensing sheets include those used in LED backlights of liquid crystal display apparatus. As such a sheet, a brightness enhancement film (BEF) manufactured by Sumitomo 3M Limited can be used.

As the shape of a prism sheet, for example, the prism sheet may be formed on a base material with pyramidal stripes having an apex angle of 90 degrees and a pitch of 50 μm. The prism sheet may also have a shape in which the apex is round, a shape in which the pitch randomly changes, or some other shape.

Further, to control the emission angle of the light from the light-emitting element, a light diffusion plate or film can be used in combination with the light-condensing sheet. For example, a light diffusion film (Light-Up) manufactured by Kimoto Co., Ltd. can be used.

<<Applications>>

The organic EL element of the present invention can be used as an electronic device, a display apparatus, a display, and various light-emitting devices. Examples of light-emitting devices include, but are not limited to, lighting devices (household lighting, vehicle interior lighting), watches and liquid crystal backlights, signboard advertisements, traffic lights, a light source of optical storage media, a light source of electrophotographic copying machines, a light source of optical communication processing machines, a light source of a light sensor, and the like. In particular, the organic EL element of the present invention can be effectively used in applications as a liquid crystal display apparatus backlight and a light source for lighting.

The organic EL element of the present invention may optionally be patterned during deposition through a metal mask or by inkjet printing or the like. The patterning may be performed only on the electrode, on the electrode and the light-emitting layer, or on all of the layers of the element. The organic EL element can be prepared by conventionally known methods.

Figure 7:
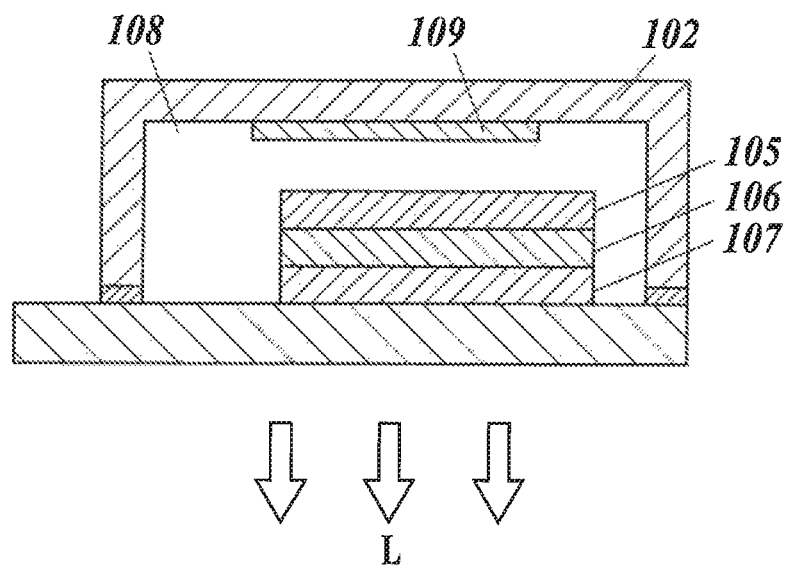
FIG. 7 is a schematic diagram of a lighting device.

The color of the light emitted from the organic EL element of the present invention or the compound according to the present invention is determined from the results of a measurement with a spectral radiance meter CS-1000 (manufactured by Konica Minolta, Inc.) applied to the CIE chromaticity coordinates shown in FIG. 7.16 on page 108 of "*Shinpen Shikisai Kagaku Handobukku*" (New Scientific Handbook of Color) (edited by the Color Science Association of Japan, published by the University of Tokyo Press, 1985).

Further, when the organic EL element of the present invention is an element that emits white light, the term "white" indicates that the chromaticity at 1000 cd/m$^2$ in the CIE1931 color system is within the region defined by X=0.33±0.07 and Y=0.33±0.1 when the front luminance is measured at a view angle of 2 degrees by the above method.

<<Display Apparatus>>

The organic EL element of the present invention can also be used for a display apparatus. The display apparatus may be monochrome or multicolor, but a multicolor display apparatus will be described here.

In the case of a multicolor display apparatus, a shadow mask is provided only during formation of the light-emitting layer, and a film can be formed on one side by a vapor deposition method, a casting method, a spin coating method, an inkjet method, a printing method, and the like.

In the case of patterning only the light-emitting layer, there is no limitation on the patterning method, but it is preferable to employ a vapor deposition method, an inkjet method, a spin coating method, or a printing method.

The structure of the organic EL element included in the display apparatus is selected from among the above-mentioned examples of the structure of the organic EL element as necessary.

Further, the method of manufacturing the organic EL element is as shown in the mode for manufacturing the organic EL element of the present invention described above.

When a DC voltage is applied to a multicolor display apparatus obtained in such a manner, emission can be observed when a voltage of about 2 to 40 V is applied with the anode set as the "+" polarity and the cathode as the "−" polarity. In addition, if a voltage is applied with the opposite polarities, current does not flow and no light is emitted at all. When an alternating voltage is applied, light is emitted only when the anode is in the "+" state and the cathode is in the "−" state. The waveform of the applied alternating current may be arbitrary.

A multicolor display apparatus can be used as a display device, a display, and various kinds of light emission source. In display devices and displays, full color display is possible by using three organic EL elements that emit blue, red, and green light.

Examples of display devices and displays include televisions, personal computers, mobile devices, AV devices, text broadcast displays, information displays in a vehicle, and the like. In particular, the multicolor display apparatus may be used as a display apparatus for playing back still images or moving images. The drive method when used as a display apparatus for moving image playback may be either a simple matrix (passive matrix) method or an active matrix method.

Examples as light emission sources include, but are not limited to, household lighting, vehicle interior lighting, watches and liquid crystal backlights, signboard advertisements, traffic lights, a light source of optical storage media, a light source of electrophotographic copying machines, a light source of optical communication processing machines, a light source of a light sensor, and the like.

An example of a display apparatus having the organic EL element of the present invention will now be described with reference to the drawings.

Figure 2:
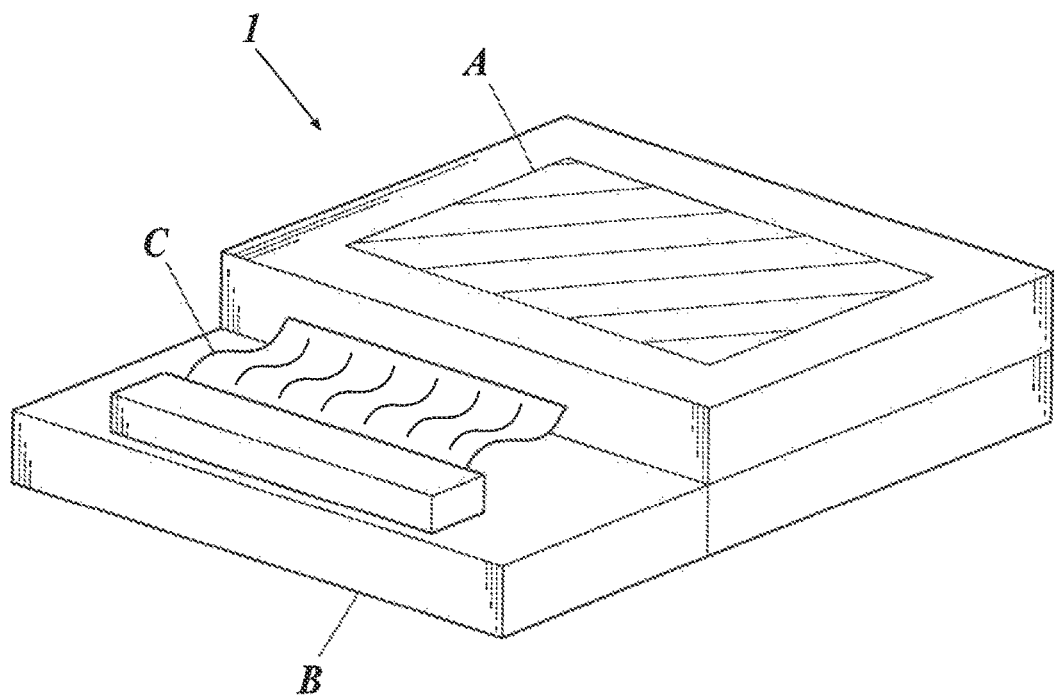
FIG. 2 is a schematic diagram illustrating an example of a display apparatus constructed from an organic EL element.

FIG. 2 is a schematic diagram illustrating an example of a display apparatus constructed from an organic EL element. FIG. 2 is a schematic diagram of, for example, a display of a mobile phone, which displays image information based on the emission of light by the organic EL element.

A display 1 has a display section A having a plurality of pixels, a control section B configured to perform image scanning of the display section A based on image information, a wiring section C electrically connecting the display section A and the control section B, and the like.

The control section B is electrically connected to the display section A via the wiring section C. The control section B sends a scanning signal and an image data signal to each of a plurality of pixels based on image information from the outside, and based on the scanning signal, scans an image by sequentially emitting light in accordance with the image data signal from the pixels of each scanning line to display the image information on the display section A.

Figure 3:
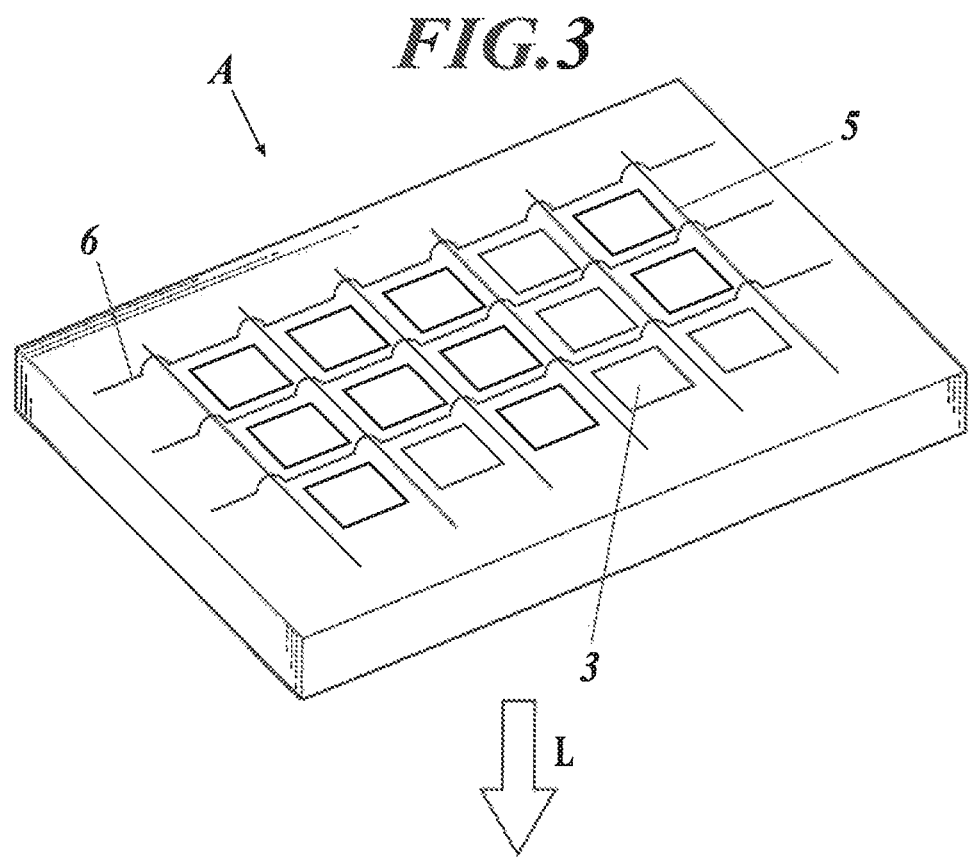
FIG. 3 is a schematic diagram of a display section A.

FIG. 3 is a schematic diagram of an active matrix display apparatus.

The display section A has a wiring section C including a plurality of scanning lines 5 and data lines 6, a plurality of pixels 3, and the like on a substrate. The main components of the display section A will be described below.

FIG. 3 illustrates a case in which the light (emission light L) emitted by the pixels 3 is extracted in the direction of the white arrow (downward direction).

The scanning lines 5 and plurality of data lines 6 of the wiring section are each made of a conductive material. The scanning lines 5 and the data lines 6 are orthogonal to each other in a lattice pattern and are connected to the pixel 3 at orthogonal positions (details are not shown in the diagram).

When a scanning signal is applied from a scanning line 5, the pixel 3 receives the image data signal from the data line 6 and emits light according to the received image data.

Full color display is possible by arranging a pixel of emission color in the red region, a pixel of emission color in the green region, and a pixel of emission color in the blue region on the same substrate as appropriate.

Figure 4:
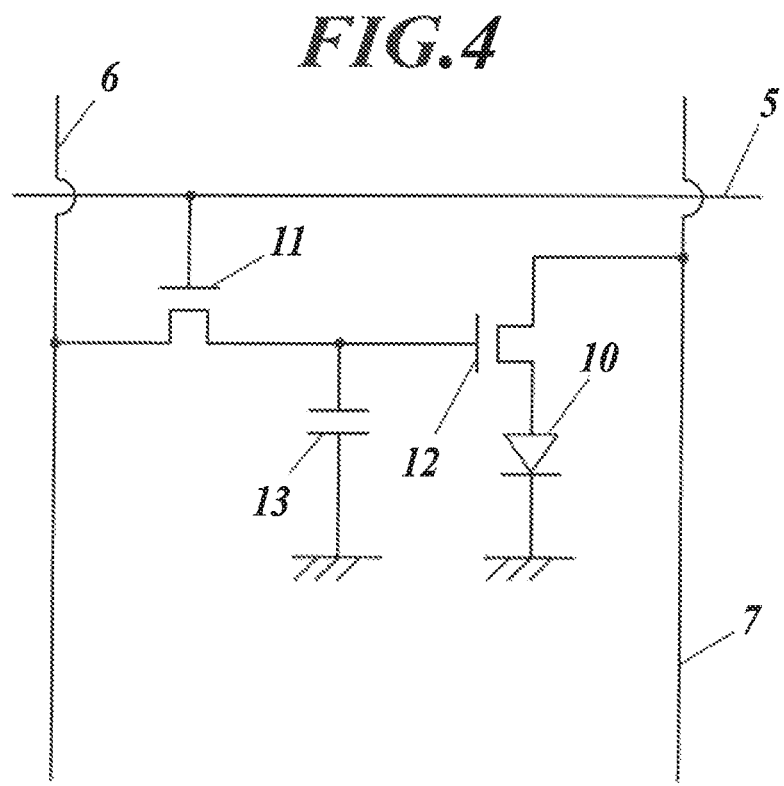
FIG. 4 is a circuit diagram of a pixel.

Next, the light emission process of the pixels is described. FIG. 4 is a schematic view illustrating a pixel circuit.

The pixel includes an organic EL element 10, a switching transistor 11, a drive transistor 12, a capacitor 13, and the like. Full color display can be performed by using organic EL elements that emit red, green and blue light as the organic EL elements 10 for a plurality of pixels, and closely arranging them together on the same substrate.

In FIG. 4, an image data signal is applied from the control section B to the drain of the switching transistor 11 via the data line 6. When a scanning signal is applied from the control section B to the gate of the switching transistor 11 via the scanning line 5, the drive of the switching transistor 11 is turned on, and the image data signal applied to the drain is transmitted to the gate of the capacitor 13 and the drive transistor 12.

As a result of the transmission of the image data signal, the capacitor 13 is charged in accordance with the potential of the image data signal, and the drive of the drive transistor 12 is turned on. In the drive transistor 12, a drain is connected to the power supply line 7. A source is connected to an electrode of the organic EL element 10. Current is supplied from the power supply line 7 to the organic EL element 10 in accordance with the potential of the image data signal applied to the gate.

When the scanning signal shifts to the next scanning line 5 in sequential scanning by the control section B, the drive of the switching transistor 11 is turned off. However, even if the drive of the switching transistor 11 is turned off, since the capacitor 13 holds the potential of the charged image data signal, the drive of the drive transistor 12 is kept in an "on" state, and light emission by the organic EL element 10 continues until the next scanning signal is applied. When a scanning signal is next applied in sequential scanning, the drive transistor 12 is driven in accordance with the potential of the next image data signal synchronized with the scanning signal, and the organic EL element 10 emits light.

Specifically, the emission of light by each organic EL element 10 of the plurality of pixels 3 is carried out by providing a switching transistor 11 and a drive transistor 12, which are active elements, for each of the organic EL elements 10 of the plurality of pixels. Such an emission method is called an active matrix method.

Here, the light emission by the organic EL element 10 may be in a plurality of gradations based on a multivalued image data signal having a plurality of gradation potentials, or a predetermined light emission amount of either on or off based on a binary image data signal. Further, the potential of the capacitor 13 may be held continuously until the application of the next scanning signal, or may be discharged just before the next scanning signal is applied.

In the present invention, the light emission method is not limited to the active matrix method described above, and the light emission may be driven based on a passive matrix method in which the organic EL elements emit light in accordance with a data signal only when a scanning signal is scanned.

Figure 5:
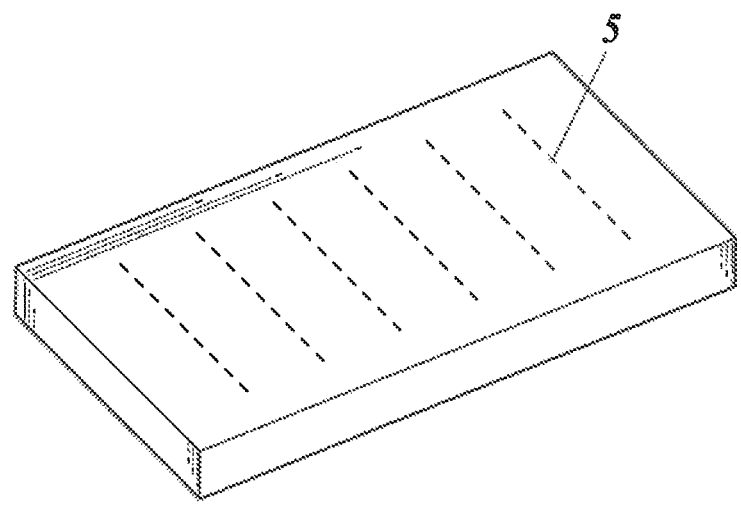
FIG. 5 is a schematic diagram of a passive matrix full-color display apparatus.
Figure 5:
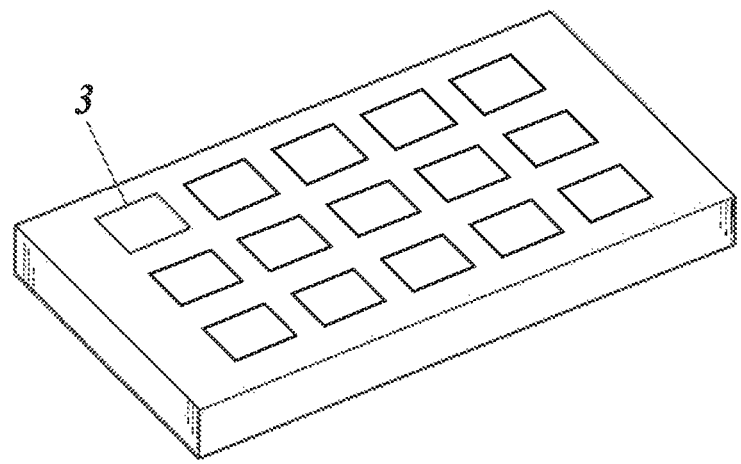
Figure 5:
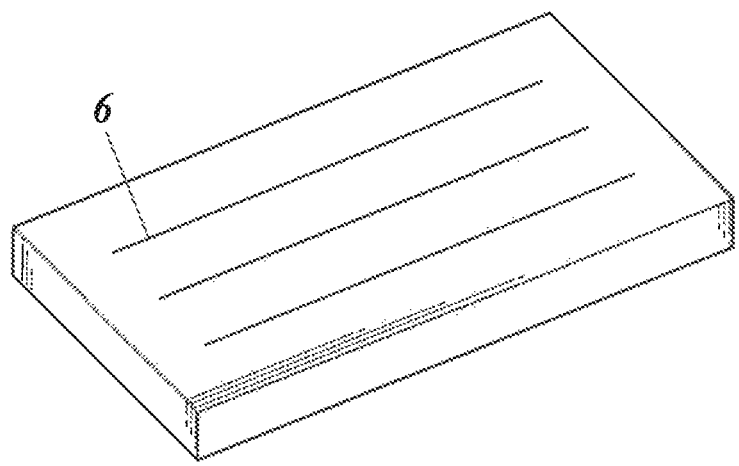

FIG. 5 is a schematic diagram of a display apparatus according to a passive matrix method. In FIG. 5, a plurality of scanning lines 5 and a plurality of image data lines 6 are provided in a lattice shape opposed to each other with pixel 3 therebetween.

When the scanning signal of a scanning line 5 is applied in sequential scanning, the pixel 3 connected to the applied scanning line 5 emits light in accordance with the image data signal.

In the passive matrix method, there are no active elements in the pixel 3, and the manufacturing cost can be reduced.

By using the organic EL element of the present invention, a display apparatus with improved luminous efficacy is obtained.

<Lighting Device>

The organic EL element of the present invention can also be used for a lighting device.

The organic EL element of the present invention may be used as an organic EL element having a resonator structure. Examples of the uses of such an organic EL element having a resonator structure include, but are not limited to, as a light source of an optical storage medium, a light source of an electrophotographic copying machine, a light source of an optical communication processing machine, a light source of a light sensor, and the like. Further, the organic EL element of the present invention may be used for the above applications by causing the element to undergo laser oscillation.

In addition, the organic EL element of the present invention may be used as a kind of lamp, such as a lighting or exposure light source, or may be used as a projection apparatus of the type that projects an image or a display apparatus (display) of a type for direct viewing of still images or moving images.

When used as a display apparatus for playback of moving images, either a passive matrix method or an active matrix method may be used as the drive method. Further, by using two kinds or more of the organic EL element of the present invention having different emission colors, a full color display apparatus can be prepared.

For example, in the case of using a plurality of light-emitting materials, emission of white light can be obtained by simultaneously emitting a plurality of colors and mixing them. The combination of a plurality of emission colors may be a combination of three emission maximum wavelengths of the three primary colors of red, green, and blue, or a combination of two emission maximum wavelengths that utilize the relationship between complementary colors such as blue and yellow, bluish green and orange, and the like.

Further, in the method of forming the organic EL element of the present invention, it is only necessary to provide a mask only when forming the light-emitting layer, the hole transport layer, the electron transport layer, or the like, and simply arrange those layers by separately coating with the mask or the like. Since the other layers are shared, patterning with a mask or the like is unnecessary. The electrode films can be formed on one side by, for example, by a vapor deposition method, casting method, spin coating method, inkjet method, printing method, or the like, thereby improving productivity.

According to this method, unlike a white organic EL device in which light-emitting elements of a plurality of colors are arrayed in parallel, the elements themselves emit white light.

[One Mode of Lighting Device]

A lighting device like that illustrated in FIG. 6 and FIG. 7 can be formed as follows. The non-light-emitting surface of the organic EL element of the present invention is covered with a glass case, then using a 300 μm-thick glass substrate as a sealing substrate, an epoxy photocurable adhesive (Luxtrack LC0629B, manufactured by Toagosei Co., Ltd.) is applied as a sealant around the periphery of the glass substrate. The workpiece is placed on the cathode, then brought into close contact with the transparent support substrate, irradiated with UV light from the glass substrate side, cured, and sealed.

Figure 6:
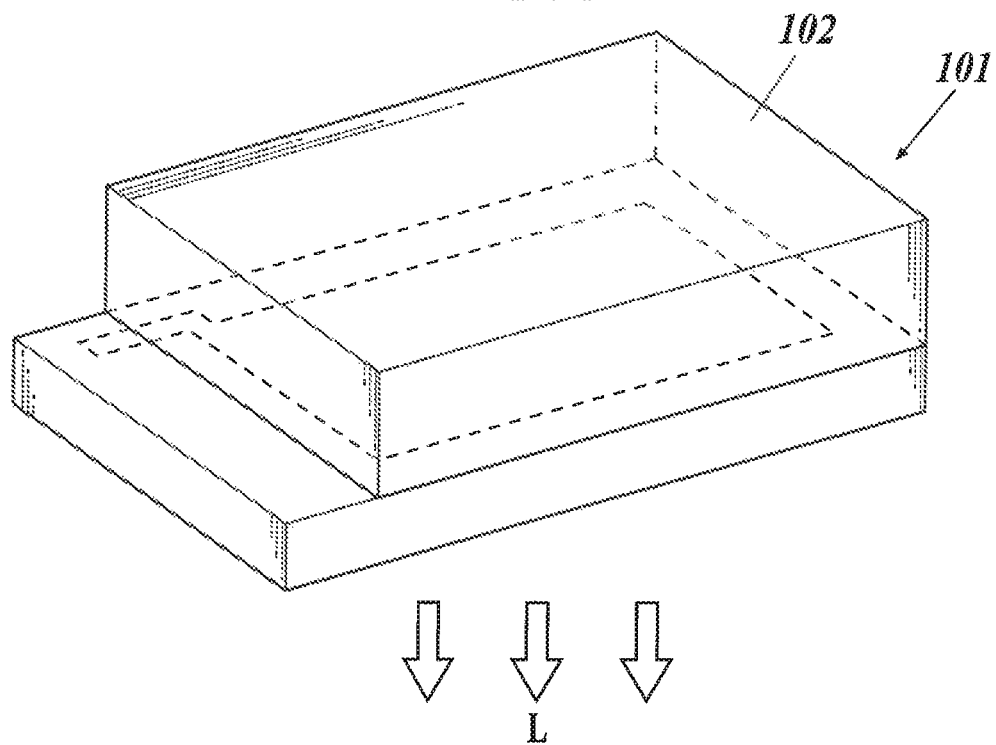
FIG. 6 is a schematic view of a lighting device.

FIG. 6 illustrates a schematic view of a lighting device. In FIG. 6, the organic EL element (organic EL element in a lighting device 101) of the present invention is covered with a glass cover 102 (the sealing operation with the glass cover was carried out in a glove box (in an atmosphere of high purity nitrogen gas having a purity of 99.999% or higher) in a nitrogen atmosphere without bringing the organic EL element in a lighting device 101 into contact with the atmosphere).

FIG. 7 is a cross-sectional view of the lighting device. In FIG. 7, reference numeral 105 denotes a cathode, reference numeral 106 denotes an organic functional layer, and reference numeral 107 denotes a glass substrate having a transparent electrode. The glass cover 102 is filled with nitrogen gas 108, and a moisture remover 109 is provided.

By using the organic EL element of the present invention, a lighting device with improved luminous efficacy was obtained.

EXAMPLES

Hereinafter, the present invention will be described in detail with reference to Examples, but the present invention is not limited thereto. In the Examples, the terms "parts" and "%" are used, but unless specified otherwise, these terms denote "parts by mass" or "% by mass".

Example 1

(Preparation of Organic EL Element)
<Preparation of Organic EL Element 1-1>

On a 50 mm×50 mm, 0.7 mm-thick glass substrate, ITO (indium-tin-oxide) was deposited to a thickness of 150 nm as an anode, and then patterned to prepare a transparent substrate having an ITO transparent electrode formed thereon. This transparent substrate was ultrasonically cleaned with isopropyl alcohol, dried with dry nitrogen gas, and subjected to UV ozone cleaning for 5 minutes. Then, the transparent substrate was fixed to a substrate holder in a commercially available vacuum vapor deposition apparatus.

The constituent materials of each layer were filled in an optimum amount for device fabrication into each of the crucibles for vapor deposition in the vacuum vapor deposition apparatus. The crucibles for vapor deposition were made of a molybdenum or tungsten resistance heating material.

After reducing the pressure to a degree of vacuum of $1 \times 10^{-4}$ Pa, a crucible for vapor deposition containing HAT-CN (1,4,5,8,9,12-hexaazatriphenylenehexacarbonitrile) was electrified and heated to perform vapor deposition on the ITO transparent electrode at a vapor deposition rate of 0.1 nm/sec, thereby forming a hole injection and transport layer having a thickness of 10 nm.

Next, α-NPD (4,4'-bis[N-(1-naphthyl)-N-phenylamino]biphenyl) was vapor-deposited on the hole injection layer at a vapor deposition rate of 0.1 nm/sec, thereby forming a hole transport layer having a thickness of 40 nm. CBP (4,4'-Bis(carbazol-9-yl)biphenyl) as a host compound and Ir(ppy)$_3$ as a light-emitting dopant were vapor-codeposited at a vapor deposition rate of 0.1 nm/sec so as to be at 90% and 10% by volume, respectively, thereby forming a light-emitting layer having a thickness of 30 nm.

Then, comparison compound 1 and LiQ (8-hydroxyquinolinato lithium) were each vapor-codeposited at a vapor deposition rate of 0.1 nm/sec so as to be 50% and 50% by volume, respectively, thereby forming an electron transport layer having a thickness of 30 nm.

Further, a 2 nm-thick LiQ layer was formed, and then 100 nm of aluminum was vapor-deposited to form a cathode.

The non-light-emitting surface side of the element was covered with a can-shaped glass case in an atmosphere of high-purity nitrogen gas having a purity of 99.999% or higher, and an electrode lead-out wire was mounted to prepare an organic EL element 1-1.

[Formula 71]

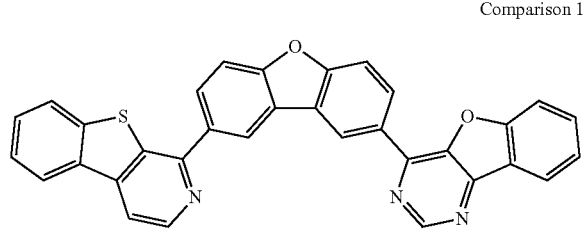

Comparison 1

<Preparation of Organic EL Elements 1-2 to 1-89>

Organic EL elements 1-2 to 1-89 were prepared in the same manner as organic EL element 1-1, except that the compounds and the like contained in the electron transport layers (1) and (2) and the electron injection layer were changed as shown in Tables I and II.

(Evaluation)

(1) Measurement of Relative Drive Voltage

For each prepared organic EL element, the front luminance at both the transparent electrode side (i.e., the transparent substrate side) and the counter electrode side (i.e., the cathode side) of each organic EL element was measured, and the voltage at the point where the sum thereof was 1000 cd/m$^2$ was measured as the drive voltage (V). It is noted that the luminance measurement was carried out using the spectral radiance meter CS-1000 (manufactured by Konica Minolta, Inc.).

The obtained drive voltage was input into the following expression to determine the relative drive voltage of each organic EL element with respect to the drive voltage of organic EL element 1-1.

Relative drive voltage(%)=(drive voltage of each organicEL element/drive voltage of organicEL element1-1)×100

The smaller the obtained numerical value is, the more preferable the obtained result is.

(2) Measurement of Change in Relative Drive Voltage Under High Temperature Storage The prepared organic EL elements were caused to emit light at a temperature of 80° C. under a constant current of 2.5 mA/cm$^2$, and the drive voltage immediately after the start of light emission and the drive voltage after 100 hours from the start were measured.

The obtained drive voltages before and after storage at high temperature were compared to determine the amount of change in the drive voltage (the value obtained by subtracting the drive voltage after storage at high temperature from the drive voltage before storage at high temperature).

The obtained amount of change in the drive voltage was input into the following expression to determine, as the change in the relative drive voltage under high temperature storage, the relative value of the amount of change in the drive voltage of each organic EL element with respect to the amount of change in the drive voltage of organic EL element 1-1.

Amount of change(%)in relative drive voltage under high temperature storage=(amount of change in drive voltage of each organicEL element/ amount of change in drive voltage of organicEL element1-1)×100

(3) Color Deviation

For each prepared organic EL element, the initial emission spectrum was measured, and the x value and the y value of the CIE chromaticity coordinates were calculated. Further, the x value and the y value were calculated from the emission spectrum after driving (when luminance reached 50%). The difference between the initial and the after-driving x value and y value was calculated from the distance of the chromaticity coordinates and expressed as a relative value with respect to a distance for the element of organic EL element 1-1 of 100.

TABLE I

| Element No. | Electron Transport Layer (1) | Electron Transport Layer (2) | Electron Injection Layer | Relative Drive Voltage [%] | Change in Relative Drive Voltage Under High Temperature Storage [%] | Color Deviation [%] | Note |
|---|---|---|---|---|---|---|---|
| 1-1 | Comparison 1 | LiQ | LiQ | 100 | 100 | 100 | Comparative Example |
| 1-2 | Comparison 1 | — | LiQ | 110 | 105 | 99 | Comparative Example |
| 1-3 | Comparison 1 | LiF | LiF | 98 | 110 | 108 | Comparative Example |
| 1-4 | Comparison 1 | KF | — | 85 | 115 | 110 | Comparative Example |
| 1-5 | M-1 | KF | — | 58 | 75 | 80 | Present Invention |
| 1-6 | M-40 | KF | — | 60 | 74 | 79 | Present Invention |
| 1-7 | M-26 | KF | — | 55 | 70 | 81 | Present Invention |
| 1-8 | M-61 | KF | — | 59 | 72 | 77 | Present Invention |
| 1-9 | M-10 | KF | — | 60 | 71 | 78 | Present Invention |
| 1-10 | M-46 | KF | — | 56 | 76 | 81 | Present Invention |
| 1-11 | M-34 | KF | — | 58 | 77 | 80 | Present Invention |
| 1-12 | M-14 | KF | — | 54 | 74 | 81 | Present Invention |
| 1-13 | M-51 | KF | — | 55 | 73 | 81 | Present Invention |
| 1-14 | M-55 | KF | — | 58 | 72 | 78 | Present Invention |
| 1-15 | M-60 | KF | — | 60 | 75 | 79 | Present Invention |
| 1-16 | M-58 | KF | — | 61 | 71 | 80 | Present Invention |
| 1-17 | M-57 | KF | — | 62 | 73 | 83 | Present Invention |
| 1-18 | M-70 | KF | — | 59 | 74 | 77 | Present Invention |
| 1-19 | M-71 | KF | — | 57 | 76 | 78 | Present Invention |
| 1-20 | M-72 | KF | — | 58 | 70 | 79 | Present Invention |
| 1-21 | M-79 | KF | — | 61 | 71 | 81 | Present Invention |
| 1-22 | M-81 | KF | — | 58 | 73 | 80 | Present Invention |
| 1-23 | M-3 | LiQ | LiQ | 75 | 65 | 75 | Present Invention |
| 1-24 | M-11 | LiQ | LiQ | 76 | 64 | 76 | Present Invention |
| 1-25 | M-48 | LiQ | LiQ | 77 | 63 | 73 | Present Invention |
| 1-26 | M-37 | LiQ | LiQ | 74 | 65 | 74 | Present Invention |

TABLE I-continued

| Element No. | Electron Transport Layer (1) | Electron Transport Layer (2) | Electron Injection Layer | Relative Drive Voltage [%] | Change in Relative Drive Voltage Under High Temperature Storage [%] | Color Deviation [%] | Note |
|---|---|---|---|---|---|---|---|
| 1-27 | M-18 | LiQ | LiQ | 73 | 64 | 73 | Present Invention |
| 1-28 | M-54 | LiQ | LiQ | 75 | 66 | 75 | Present Invention |
| 1-29 | M-59 | — | LiQ | 74 | 63 | 74 | Present Invention |
| 1-30 | M-63 | — | LiQ | 72 | 65 | 72 | Present Invention |
| 1-31 | M-82 | — | LiQ | 74 | 64 | 73 | Present Invention |
| 1-32 | M-75 | — | LiQ | 73 | 63 | 74 | Present Invention |
| 1-33 | M-77 | — | LiQ | 75 | 65 | 73 | Present Invention |
| 1-34 | M-5 | — | LiQ | 73 | 65 | 74 | Present Invention |
| 1-35 | M-22 | — | LiQ | 74 | 64 | 75 | Present Invention |
| 1-36 | M-9 | LiF | LiF | 75 | 65 | 85 | Present Invention |
| 1-37 | M-81 | LiF | LiF | 73 | 66 | 84 | Present Invention |
| 1-38 | M-50 | LiF | LiF | 74 | 64 | 83 | Present Invention |
| 1-39 | M-69 | LiF | LiF | 75 | 63 | 85 | Present Invention |
| 1-40 | M-101 | KF | — | 62 | 74 | 78 | Present Invention |
| 1-41 | M-112 | KF | — | 65 | 73 | 79 | Present Invention |
| 1-42 | M-123 | KF | — | 66 | 71 | 79 | Present Invention |
| 1-43 | M-136 | KF | — | 63 | 73 | 78 | Present Invention |
| 1-44 | M-141 | LiQ | LiQ | 73 | 67 | 73 | Present Invention |
| 1-45 | M-103 | LiQ | LiQ | 72 | 65 | 72 | Present Invention |

TABLE II

| Element No. | Electron Transport Layer (1) | Electron Transport Layer (2) | Electron Injection Layer | Relative Drive Voltage [%] | Change in Relative Drive Voltage Under High Temperature Storage [%] | Color Deviation [%] | Note |
|---|---|---|---|---|---|---|---|
| 1-46 | M-118 | LiQ | LiQ | 73 | 68 | 71 | Present Invention |
| 1-47 | M-121 | — | LiQ | 76 | 65 | 71 | Present Invention |
| 1-48 | M-138 | — | LiQ | 77 | 64 | 75 | Present Invention |
| 1-49 | M-144 | — | LiQ | 74 | 62 | 77 | Present Invention |
| 1-50 | M-135 | — | LiQ | 75 | 66 | 77 | Present Invention |
| 1-51 | M-125 | LiF | LiF | 73 | 67 | 80 | Present Invention |
| 1-52 | M-114 | LiF | LiF | 70 | 62 | 83 | Present Invention |
| 1-53 | M-106 | LiF | LiF | 74 | 65 | 80 | Present Invention |
| 1-54 | M-145 | LiQ | LiQ | 74 | 72 | 73 | Present Invention |
| 1-55 | M-146 | LiQ | LiQ | 73 | 73 | 74 | Present Invention |
| 1-56 | M-148 | — | LiQ | 75 | 76 | 73 | Present Invention |
| 1-57 | M-151 | — | LiQ | 73 | 77 | 74 | Present Invention |
| 1-58 | M-153 | — | LiQ | 75 | 74 | 73 | Present Invention |
| 1-59 | M-154 | — | LiQ | 73 | 75 | 74 | Present Invention |
| 1-60 | M-158 | LiF | LiF | 75 | 73 | 85 | Present Invention |
| 1-61 | M-159 | LiF | LiF | 73 | 70 | 84 | Present Invention |
| 1-62 | M-160 | LiF | LiF | 74 | 74 | 83 | Present Invention |
| 1-63 | M-170 | LiQ | LiQ | 76 | 75 | 73 | Present Invention |
| 1-64 | M-177 | LiQ | LiQ | 77 | 76 | 72 | Present Invention |
| 1-65 | M-184 | LiQ | LiQ | 74 | 77 | 73 | Present Invention |
| 1-66 | M-185 | LiQ | LiQ | 73 | 74 | 72 | Present Invention |
| 1-67 | M-198 | LiQ | — | 75 | 70 | 73 | Present Invention |
| 1-68 | M-208 | LiQ | — | 73 | 72 | 78 | Present Invention |
| 1-69 | M-211 | LiQ | — | 77 | 71 | 75 | Present Invention |
| 1-70 | M-192 | LiQ | — | 76 | 70 | 75 | Present Invention |
| 1-71 | M-194 | LiQ | — | 77 | 73 | 72 | Present Invention |
| 1-72 | M-215 | LiQ | LiQ | 74 | 72 | 74 | Present Invention |
| 1-73 | M-217 | LiQ | LiQ | 73 | 71 | 75 | Present Invention |
| 1-74 | M-220 | LiQ | — | 73 | 70 | 75 | Present Invention |
| 1-75 | M-221 | LiQ | — | 75 | 69 | 74 | Present Invention |
| 1-76 | M-225 | LiQ | — | 76 | 72 | 77 | Present Invention |
| 1-77 | M-227 | LiQ | — | 74 | 68 | 76 | Present Invention |
| 1-78 | M-229 | LiQ | — | 75 | 71 | 74 | Present Invention |
| 1-79 | M-231 | LiQ | — | 77 | 68 | 73 | Present Invention |
| 1-80 | M-238 | LiQ | — | 72 | 69 | 75 | Present Invention |
| 1-81 | M-242 | LiQ | — | 74 | 70 | 72 | Present Invention |
| 1-82 | M-244 | LiQ | — | 76 | 69 | 71 | Present Invention |
| 1-83 | M-256 | LiQ | — | 75 | 70 | 75 | Present Invention |
| 1-84 | M-259 | LiQ | — | 76 | 74 | 72 | Present Invention |
| 1-85 | M-285 | LiQ | — | 77 | 72 | 73 | Present Invention |
| 1-86 | M-269 | LiQ | — | 74 | 71 | 72 | Present Invention |

TABLE II-continued

| Element No. | Electron Transport Layer (1) | Electron Transport Layer (2) | Electron Injection Layer | Relative Drive Voltage [%] | Change in Relative Drive Voltage Under High Temperature Storage [%] | Color Deviation [%] | Note |
|---|---|---|---|---|---|---|---|
| 1-87 | M-303 | LiQ | — | 77 | 73 | 75 | Present Invention |
| 1-88 | M-279 | LiQ | — | 75 | 75 | 73 | Present Invention |
| 1-89 | M-341 | LiQ | — | 73 | 71 | 73 | Present Invention |

Example 2

(Preparation of Transparent Electrode)
<Preparation of Transparent Electrode 2-1>

On a 50 mm×50 mm, 0.7 mm-thick glass substrate, a crucible for vapor deposition containing comparison compound 2 was electrified and heated to perform vapor deposition at a vapor deposition rate of 0.1 nm/sec, thereby forming an organic functional layer (cathode base layer) having a thickness of 25 nm.

Next, silver was vapor deposited at a vapor deposition rate of 0.1 nm/sec to form a cathode having a thickness of 8 nm, which was used as a transparent electrode 2-1.

[Formula 72]

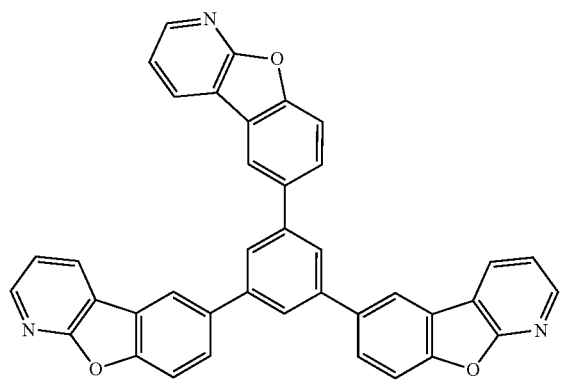

Comparison 2

<Preparation of Transparent Electrodes 2-2 to 2-5>

Transparent electrodes 2-2 to 2-5 were prepared in the same manner as transparent electrode 2-1, except that the compound used in the organic functional layer and the thickness of the cathode were changed as shown in Table III.

(Evaluation)

(1) Light Transmittance (%)

The light transmittance of each of the prepared transparent electrodes 2-1 to 2-5 was measured.

The light transmittance was measured using the same equipment as the sample as a baseline using a spectrophotometer (U-3300, manufactured by Hitachi High-Tech Science Corporation).

(2) Sheet Resistance Value

The sheet resistance value of each of the prepared transparent electrodes 2-1 to 2-5 was measured.

The sheet resistance value was measured by a 4-terminal, 4-probe low current application method using a resistivity meter (MCP-T610, manufactured by Mitsubishi Chemical Analytech Co., Ltd.).

TABLE III

| Element No. | Organic Functional Layer | Cathode Thickness [nm] | Light Transmittance (at 550 nm) [%] | Sheet Resistance Value [Ω/sq.] | Note |
|---|---|---|---|---|---|
| 2-1 | Comparison 2 | 8 | 60.5 | 28.5 | Comparative Example |
| 2-2 | M-83 | 20 | 51.0 | 1.5 | Present Invention |
| 2-3 | M-83 | 13 | 55.0 | 4.0 | Present Invention |
| 2-4 | M-83 | 8 | 70.0 | 9.1 | Present Invention |
| 2-5 | M-85 | 8 | 72.0 | 8.0 | Present Invention |

Example 3

(Preparation of Organic EL Element)

On a 50 mm×50 mm, 0.7 mm-thick glass substrate, ITO (indium-tin-oxide) was deposited to a thickness of 150 nm as an anode, and then patterned to prepare a transparent substrate having an ITO transparent electrode formed thereon. This transparent substrate was ultrasonically cleaned with isopropyl alcohol, dried with dry nitrogen gas, and subjected to UV ozone cleaning for 5 minutes. Then, the transparent substrate was fixed to a substrate holder in a commercially available vacuum vapor deposition apparatus.

The constituent materials of each layer were filled in an optimum amount for device fabrication into each of the crucibles for vapor deposition in the vacuum vapor deposition apparatus. The crucibles for vapor deposition were made of a molybdenum or tungsten resistance heating material.

After reducing the pressure to a degree of vacuum of $1 \times 10^{-4}$ Pa, a crucible for vapor deposition containing HAT-CN (1,4,5,8,9,12-hexaazatriphenylenehexacarbonitrile) was electrified and heated to perform vapor deposition on the ITO transparent electrode at a vapor deposition rate of 0.1 nm/sec, thereby forming a hole injection and transport layer having a thickness of 10 nm.

Next, α-NPD (4,4'-bis[N-(1-naphthyl)-N-phenylamino]biphenyl) was vapor-deposited on the hole injection layer at a vapor deposition rate of 0.1 nm/sec, thereby forming a hole transport layer having a thickness of 40 nm.

CBP as a host compound and Ir(ppy)$_3$ as a light-emitting dopant were vapor-codeposited at a vapor deposition rate of 0.1 nm/sec so as to be at 90% and 10% by volume, respectively, thereby forming a light-emitting layer having a thickness of 30 nm.

Then, comparison compound 3 and KF were each vapor-codeposited at a vapor deposition rate of 0.1 nm/sec so as to be 85% and 15% by volume, respectively, thereby forming an electron transport layer having a thickness of 30 nm.

Then, silver was vapor deposited at a vapor deposition rate of 0.1 nm/sec to form a cathode having a thickness of 13 nm.

The non-light-emitting surface side of the element was covered with a can-shaped glass case in an atmosphere of high-purity nitrogen gas having a purity of 99.999% or higher, and an electrode lead-out wire was mounted to prepare an organic EL element 3-1.

[Formula 73]

Comparison 3

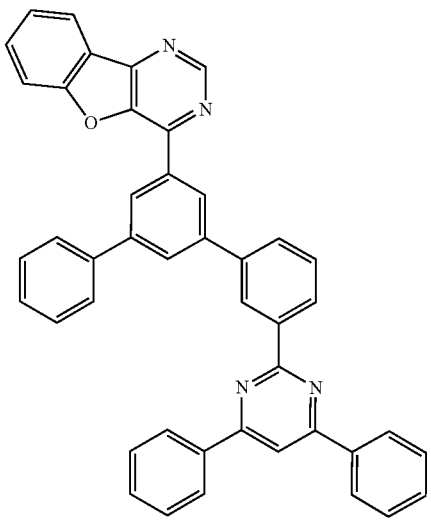

<Preparation of Organic EL Elements 3-2 to 3-72>

Organic EL elements 3-2 to 3-72 were prepared in the same manner as organic EL element 3-1, except that the compound of the electron transport layer, the ratio of silver to magnesium, and the thickness of the cathode were changed as shown in Table IV and Table V.

(Evaluation)

(1) Measurement of Relative Drive Voltage

For each prepared organic EL element, the front luminance at both the transparent electrode side (i.e., the transparent substrate side) and the counter electrode side (i.e., the cathode side) of each organic EL element was measured, and the voltage at the point where the sum thereof was 1000 cd/m$^2$ was measured as the drive voltage (V). It is noted that the luminance measurement was carried out using the spectral radiance meter CS-1000 (manufactured by Konica Minolta, Inc.).

The obtained drive voltage was input into the following expression to determine the relative drive voltage of each organic EL element with respect to the drive voltage of organic EL element 3-1.

Relative drive voltage(%)=(drive voltage of each organic*EL* element/drive voltage of organic*EL* element3-1)×100

The smaller the obtained numerical value is, the more preferable the obtained result is.

(2) Measurement of Change in Relative Drive Voltage Under High Temperature Storage The prepared organic EL elements were caused to emit light at a temperature of 80° C. under a constant current of 2.5 mA/cm$^2$, and the drive voltage immediately after the start of light emission and the drive voltage after 100 hours from the start were measured.

The obtained drive voltages before and after storage at high temperature were compared to determine the amount of change in the drive voltage (the value obtained by subtracting the drive voltage after storage at high temperature from the drive voltage before storage at high temperature).

The obtained amount of change in the drive voltage was input into the following expression to determine, as the change in the relative drive voltage under high temperature storage, the relative value of the amount of change in the drive voltage of each organic EL element with respect to the amount of change in the drive voltage of organic EL element 3-1.

Amount of change(%)in relative drive voltage under high temperature storage=(amount of change in drive voltage of each organic *EL* element/amount of change in drive voltage of organic *EL* element3-1)×100

TABLE IV

| Element No. | Electron Transport Layer | Ratio Ag | Mg | Cathode Thickness [nm] | Relative Drive Voltage [%] | Change in Relative Drive Voltage Under High Temperature Storage [%] | Note |
|---|---|---|---|---|---|---|---|
| 3-1 | Comparison 3 | 100 | 0 | 15 | 100 | 100 | Comparative Example |
| 3-2 | Comparison 3 | 100 | 0 | 10 | 120 | 150 | Comparative Example |
| 3-3 | Comparison 3 | 90 | 10 | 20 | 95 | 94 | Comparative Example |
| 3-4 | Comparison 3 | 90 | 10 | 10 | 98 | 98 | Comparative Example |
| 3-5 | Comparison 3 | 80 | 20 | 10 | 115 | 110 | Comparative Example |
| 3-6 | M-2 | 100 | 0 | 10 | 85 | 63 | Present Invention |
| 3-7 | M-62 | 100 | 0 | 10 | 84 | 62 | Present Invention |
| 3-8 | M-39 | 100 | 0 | 10 | 84 | 65 | Present Invention |
| 3-9 | M-20 | 100 | 0 | 10 | 83 | 67 | Present Invention |
| 3-10 | M-85 | 100 | 0 | 10 | 83 | 63 | Present Invention |
| 3-11 | M-6 | 90 | 10 | 10 | 72 | 64 | Present Invention |
| 3-12 | M-60 | 90 | 10 | 10 | 75 | 65 | Present Invention |
| 3-13 | M-67 | 90 | 10 | 10 | 71 | 66 | Present Invention |
| 3-14 | M-70 | 80 | 20 | 10 | 85 | 73 | Present Invention |
| 3-15 | M-24 | 80 | 20 | 10 | 84 | 75 | Present Invention |
| 3-16 | M-2 | 100 | 0 | 15 | 79 | 66 | Present Invention |
| 3-17 | M-2 | 100 | 0 | 20 | 75 | 65 | Present Invention |
| 3-18 | M-2 | 100 | 0 | 8 | 84 | 73 | Present Invention |

TABLE IV-continued

| Element No. | Electron Transport Layer | Ratio Ag | Ratio Mg | Cathode Thickness [nm] | Relative Drive Voltage [%] | Change in Relative Drive Voltage Under High Temperature Storage [%] | Note |
|---|---|---|---|---|---|---|---|
| 3-19 | M-20 | 90 | 10 | 15 | 72 | 75 | Present Invention |
| 3-20 | M-20 | 90 | 10 | 20 | 77 | 66 | Present Invention |
| 3-21 | M-20 | 90 | 10 | 8 | 80 | 68 | Present Invention |
| 3-22 | M-56 | 100 | 0 | 15 | 80 | 65 | Present Invention |
| 3-23 | M-56 | 100 | 0 | 20 | 76 | 64 | Present Invention |
| 3-24 | M-56 | 100 | 0 | 8 | 85 | 63 | Present Invention |
| 3-25 | M-27 | 100 | 0 | 10 | 86 | 63 | Present Invention |
| 3-26 | M-30 | 100 | 0 | 10 | 85 | 65 | Present Invention |
| 3-27 | M-43 | 100 | 0 | 10 | 86 | 67 | Present Invention |
| 3-28 | M-52 | 90 | 10 | 10 | 75 | 65 | Present Invention |
| 3-29 | M-66 | 90 | 10 | 10 | 71 | 68 | Present Invention |
| 3-30 | M-78 | 80 | 20 | 10 | 87 | 73 | Present Invention |
| 3-31 | M-87 | 80 | 20 | 10 | 84 | 74 | Present Invention |
| 3-32 | M-149 | 100 | 0 | 10 | 84 | 62 | Present Invention |
| 3-33 | M-150 | 100 | 0 | 10 | 84 | 65 | Present Invention |
| 3-34 | M-161 | 100 | 0 | 10 | 83 | 67 | Present Invention |
| 3-35 | M-162 | 90 | 10 | 10 | 75 | 65 | Present Invention |
| 3-36 | M-163 | 90 | 10 | 10 | 71 | 66 | Present Invention |
| 3-37 | M-171 | 90 | 10 | 10 | 75 | 65 | Present Invention |
| 3-38 | M-174 | 90 | 10 | 10 | 71 | 66 | Present Invention |
| 3-39 | M-178 | 80 | 20 | 10 | 86 | 73 | Present Invention |
| 3-40 | M-181 | 80 | 20 | 10 | 87 | 70 | Present Invention |

TABLE V

| Element No. | Electron Transport Layer | Ratio Ag | Ratio Mg | Cathode Thickness [nm] | Relative Drive Voltage [%] | Change in Relative Drive Voltage Under High Temperature Storage [%] | Note |
|---|---|---|---|---|---|---|---|
| 3-41 | M-183 | 100 | 0 | 8 | 83 | 64 | Present Invention |
| 3-42 | M-186 | 100 | 0 | 8 | 81 | 65 | Present Invention |
| 3-43 | M-166 | 100 | 0 | 8 | 82 | 65 | Present Invention |
| 3-44 | M-167 | 100 | 0 | 8 | 83 | 63 | Present Invention |
| 3-45 | M-168 | 90 | 10 | 10 | 70 | 61 | Present Invention |
| 3-46 | M-169 | 90 | 10 | 10 | 72 | 64 | Present Invention |
| 3-47 | M-175 | 90 | 10 | 10 | 73 | 60 | Present Invention |
| 3-48 | M-176 | 90 | 10 | 10 | 71 | 66 | Present Invention |
| 3-49 | M-180 | 90 | 10 | 10 | 72 | 65 | Present Invention |
| 3-50 | M-182 | 90 | 10 | 10 | 73 | 64 | Present Invention |
| 3-51 | M-199 | 90 | 10 | 10 | 70 | 65 | Present Invention |
| 3-52 | M-211 | 90 | 10 | 10 | 73 | 66 | Present Invention |
| 3-53 | M-195 | 90 | 10 | 10 | 75 | 69 | Present Invention |
| 3-54 | M-212 | 90 | 10 | 8 | 83 | 68 | Present Invention |
| 3-55 | M-214 | 90 | 10 | 10 | 75 | 69 | Present Invention |
| 3-56 | M-224 | 90 | 10 | 10 | 71 | 66 | Present Invention |
| 3-57 | M-232 | 100 | 0 | 10 | 72 | 64 | Present Invention |
| 3-58 | M-228 | 90 | 10 | 10 | 72 | 66 | Present Invention |
| 3-59 | M-232 | 90 | 10 | 10 | 74 | 67 | Present Invention |
| 3-60 | M-235 | 100 | 0 | 10 | 73 | 65 | Present Invention |
| 3-61 | M-240 | 90 | 10 | 10 | 73 | 66 | Present Invention |
| 3-62 | M-245 | 90 | 10 | 10 | 73 | 67 | Present Invention |
| 3-63 | M-258 | 90 | 10 | 8 | 82 | 68 | Present Invention |
| 3-64 | M-292 | 90 | 10 | 10 | 75 | 66 | Present Invention |
| 3-65 | M-301 | 90 | 10 | 8 | 84 | 68 | Present Invention |
| 3-66 | M-347 | 90 | 10 | 10 | 75 | 66 | Present Invention |
| 3-67 | M-294 | 90 | 10 | 8 | 83 | 67 | Present Invention |
| 3-68 | M-337 | 90 | 10 | 10 | 74 | 69 | Present Invention |
| 3-69 | M-271 | 90 | 10 | 8 | 82 | 68 | Present Invention |
| 3-70 | M-296 | 90 | 10 | 10 | 75 | 68 | Present Invention |
| 3-71 | M-339 | 90 | 10 | 8 | 82 | 68 | Present Invention |
| 3-72 | M-282 | 90 | 10 | 10 | 74 | 69 | Present Invention |

Example 4

(Preparation of Organic EL Element)

<Preparation of Organic EL Element 4-1>

On a 50 mm×50 mm, 0.7 mm-thick glass substrate, ITO (indium-tin-oxide) was deposited to a thickness of 150 nm as an anode, and then patterned to prepare a transparent substrate having an ITO transparent electrode formed thereon. This transparent substrate was ultrasonically cleaned with isopropyl alcohol, dried with dry nitrogen gas, and subjected to UV ozone cleaning for 5 minutes. Then, the transparent substrate was fixed to a substrate holder in a commercially available vacuum vapor deposition apparatus.

The constituent materials of each layer were filled in an optimum amount for device fabrication into each of the crucibles for vapor deposition in the vacuum vapor deposition apparatus. The crucibles for vapor deposition were made of a molybdenum or tungsten resistance heating material.

After reducing the pressure to a degree of vacuum of $1\times10^{-4}$ Pa, a crucible for vapor deposition containing HAT-CN (1,4,5,8,9,12-hexaazatriphenylenehexacarbonitrile) was electrified and heated to perform vapor deposition on the ITO transparent electrode at a vapor deposition rate of 0.1 nm/sec, thereby forming a hole injection and transport layer having a thickness of 10 nm.

Next, α-NPD (4,4'-bis[N-(1-naphthyl)-N-phenylamino] biphenyl) was vapor-deposited on the hole injection layer at a vapor deposition rate of 0.1 nm/sec, thereby forming a hole transport layer having a thickness of 40 nm.

CBP as a host compound and Ir(ppy)$_3$ as a light-emitting dopant were vapor-codeposited at a vapor deposition rate of 0.1 nm/sec so as to be at 90% and 10% by volume, respectively, thereby forming a light-emitting layer having a thickness of 30 nm.

Then, as an electron transport layer, Alq$_3$ was vapor-deposited at a vapor deposition rate of 0.1 nm/sec to form an electron transport layer having a thickness of 30 nm.

Then, comparison compound 4 and LiQ were each vapor-codeposited at a vapor deposition rate of 0.1 nm/sec so as to be 50% and 50% by volume, respectively, thereby forming an electron injection layer having a thickness of 2 nm.

Then, silver and magnesium were each vapor-codeposited at a vapor deposition rate of 0.1 nm/sec and 0.01 nm/sec, respectively, to form a cathode having a thickness of 8 nm.

The non-light-emitting surface side of the element was covered with a can-shaped glass case in an atmosphere of high-purity nitrogen gas having a purity of 99.999% or higher, and an electrode lead-out wire was mounted to prepare an organic EL element 4-1.

[Formula 74]

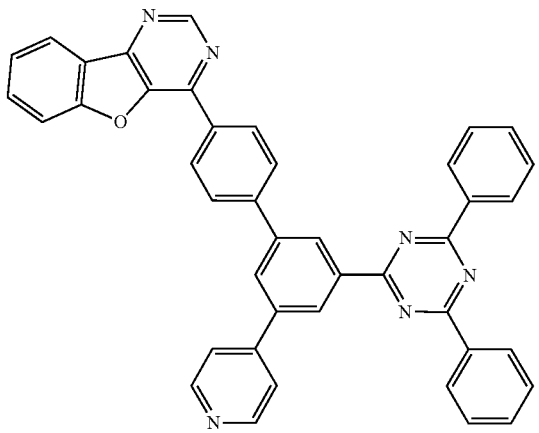

Comparison 4

<Preparation of Organic EL Elements 4-2 to 4-34>

Organic EL elements 4-2 to 4-34 were prepared by changing the compound of the electron injection layer, the ratio of silver to magnesium, and the thickness of the cathode of organic EL element 4-1 to as shown in Table VI.

(Evaluation)

(1) Measurement of Relative Drive Voltage

For each prepared organic EL element, the front luminance at both the transparent electrode side (i.e., the transparent substrate side) and the counter electrode side (i.e., the cathode side) of each organic EL element was measured, and the voltage at the point where the sum thereof was 1000 cd/m$^2$ was measured as the drive voltage (V). It is noted that the luminance measurement was carried out using the spectral radiance meter CS-1000 (manufactured by Konica Minolta, Inc.).

The obtained drive voltage was input into the following expression to determine the relative drive voltage of each organic EL element with respect to the drive voltage of organic EL element 4-1.

Relative drive voltage(%)=(drive voltage of each organic*EL* element/drive voltage of organic*EL* element4-1)×100

The smaller the obtained numerical value is, the more preferable the obtained result is.

(2) Measurement of Change in Relative Drive Voltage Under High Temperature Storage The prepared organic EL elements were caused to emit light at a temperature of 80° C. under a constant current of 2.5 mA/cm$^2$, and the drive voltage immediately after the start of light emission and the drive voltage after 100 hours from the start were measured.

The obtained drive voltages before and after storage at high temperature were compared to determine the amount of change in the drive voltage (the value obtained by subtracting the drive voltage after storage at high temperature from the drive voltage before storage at high temperature).

The obtained amount of change in the drive voltage was input into the following expression to determine, as the change in the relative drive voltage under high temperature storage, the relative value of the amount of change in the drive voltage of each organic EL element with respect to the amount of change in the drive voltage of organic EL element 4-1.

Amount of change(%)in relative drive voltage under high temperature storage=(amount of change in drive voltage of each organic*EL* element/ amount of change in drive voltage of organic*EL* element4-1)×100

TABLE VI

| Element No. | Electron Injection Layer | Ratio Ag | Ratio Mg | Cathode Thickness [nm] | Relative Drive Voltage [%] | Change in Relative Drive Voltage Under High Temperature Storage [%] | Note |
|---|---|---|---|---|---|---|---|
| 4-1 | Comparison 4 | 90 | 10 | 8 | 100 | 100 | Comparative Example |
| 4-2 | Comparison 4 | 100 | 0 | 10 | 120 | 134 | Comparative Example |
| 4-3 | Comparison 4 | 90 | 10 | 15 | 93 | 90 | Comparative Example |
| 4-4 | M-1 | 90 | 10 | 8 | 80 | 62 | Present Invention |
| 4-5 | M-2 | 90 | 10 | 8 | 77 | 62 | Present Invention |
| 4-6 | M-6 | 90 | 10 | 8 | 79 | 63 | Present Invention |
| 4-7 | M-12 | 90 | 10 | 8 | 80 | 62 | Present Invention |
| 4-8 | M-15 | 90 | 10 | 10 | 82 | 65 | Present Invention |
| 4-9 | M-19 | 90 | 10 | 12 | 83 | 67 | Present Invention |
| 4-10 | M-28 | 100 | 0 | 10 | 85 | 63 | Present Invention |
| 4-11 | M-29 | 100 | 0 | 10 | 86 | 64 | Present Invention |
| 4-12 | M-36 | 100 | 0 | 10 | 85 | 65 | Present Invention |
| 4-13 | M-41 | 100 | 0 | 8 | 82 | 66 | Present Invention |
| 4-14 | M-42 | 100 | 0 | 8 | 85 | 65 | Present Invention |
| 4-15 | M-49 | 100 | 0 | 12 | 84 | 66 | Present Invention |
| 4-16 | M-64 | 100 | 0 | 12 | 81 | 63 | Present Invention |
| 4-17 | M-74 | 80 | 20 | 8 | 75 | 65 | Present Invention |
| 4-18 | M-80 | 80 | 20 | 8 | 76 | 63 | Present Invention |
| 4-19 | M-86 | 80 | 20 | 10 | 77 | 65 | Present Invention |
| 4-20 | M-89 | 80 | 20 | 12 | 77 | 66 | Present Invention |
| 4-21 | M-147 | 90 | 10 | 8 | 75 | 62 | Present Invention |
| 4-22 | M-152 | 90 | 10 | 8 | 78 | 65 | Present Invention |
| 4-23 | M-155 | 90 | 10 | 10 | 80 | 65 | Present Invention |
| 4-24 | M-156 | 90 | 10 | 10 | 82 | 63 | Present Invention |
| 4-25 | M-157 | 100 | 0 | 10 | 85 | 63 | Present Invention |
| 4-26 | M-164 | 100 | 0 | 10 | 84 | 62 | Present Invention |
| 4-27 | M-165 | 100 | 0 | 10 | 83 | 65 | Present Invention |
| 4-28 | M-172 | 100 | 0 | 10 | 85 | 65 | Present Invention |
| 4-29 | M-173 | 90 | 10 | 8 | 79 | 60 | Present Invention |
| 4-30 | M-179 | 90 | 10 | 8 | 78 | 62 | Present Invention |
| 4-31 | M-187 | 90 | 10 | 10 | 79 | 62 | Present Invention |
| 4-32 | M-197 | 90 | 10 | 8 | 81 | 65 | Present Invention |
| 4-33 | M-205 | 100 | 0 | 13 | 80 | 66 | Present Invention |
| 4-34 | M-201 | 90 | 10 | 10 | 77 | 63 | Present Invention |

From the above, it was found that the organic EL element of the present invention has a lower relative drive voltage than the organic EL elements of the comparative examples, and superior durability due to its smaller change in relative drive voltage under high temperature storage.

According to the present invention, it is possible to provide an organic electroluminescence element with improved drive voltage and durability, and a material for organic electroluminescence used in that organic electroluminescence element.

Although not entirely clear, the mechanism by which the effects of the present invention are exhibited or made to act are presumed to be as follows.

The present inventors discovered that a compound represented by the general formula (1) used in the organic electroluminescence element of the present invention contributes to an improvement in the speed of electron hopping due to the aromatic heterocyclic ring containing a nitrogen atom included in the molecule.

In other words, by introducing an aromatic fused heterocyclic ring containing an N atom in the molecule, intermolecular interaction is increased, which strengthens electron hopping.

This is thought to have enabled an increase in the speed of electron hopping by utilizing both the 7c-7c interaction utilizing the fused ring with a wide electron cloud and the π-π interaction between the unpaired electrons of the N atom and π electrons.

Although embodiments of the present invention have been described and illustrated in detail, the disclosed embodiments are made for purposes of illustration and example only and not limitation. The scope of the present invention should be interpreted by terms of the appended claims.

INDUSTRIAL APPLICABILITY

The present invention relates to an organic electroluminescence element having improved drive voltage and durability, and to a material for organic electroluminescence used in that organic electroluminescence element.

REFERENCE SIGNS LIST 1 display
3 pixel
5 scanning line
6 data line
7 power supply line
10 organic EL element
11 switching transistor
12 drive transistor
13 capacitor
101 organic EL element in a lighting device
102 glass cover
105 cathode
106 organic functional layer
107 glass substrate having transparent electrode
108 nitrogen gas
109 moisture remover
A display section B control section
C wiring section
L emission light

The invention claimed is:

1. An organic electroluminescence element comprising an anode, a plurality of organic functional layers including a light-emitting layer, and a cathode in that order,
   wherein the organic functional layer containing a compound having a structure represented by the following general formula (2) is arranged between the light-emitting layer and the cathode:

General formula (2)

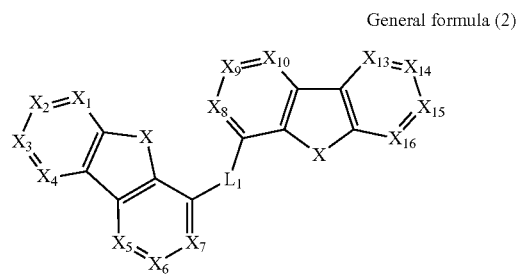

wherein X represents an oxygen atom or a sulfur atom; $X_1$ to $X_{10}$ each independently represent $CR_1$ or a nitrogen atom; one of $X_5$ and $X_7$ represents a nitrogen atom and the other represents $CR_1$; one of $X_8$ and $X_{10}$ represents a nitrogen atom and the other represents $CR_1$; $X_{13}$ to $X_{16}$ each independently represent $CR_1$ or a nitrogen atom;

$R_1$ represents a hydrogen atom or a substituent selected from the group consisting of:

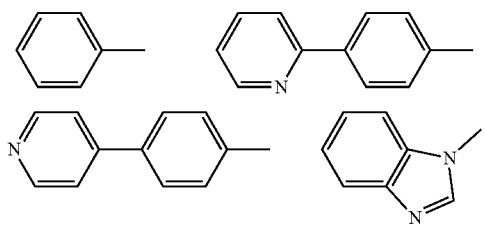

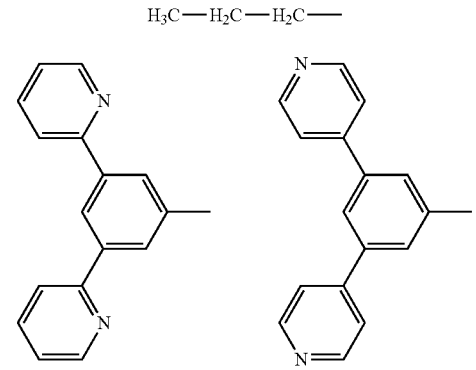

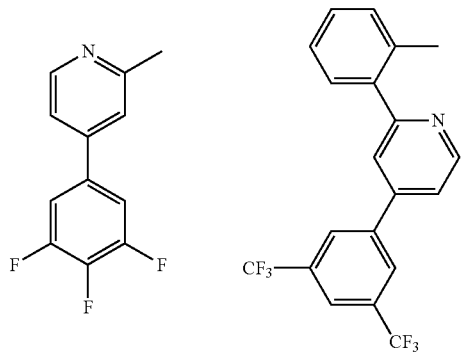

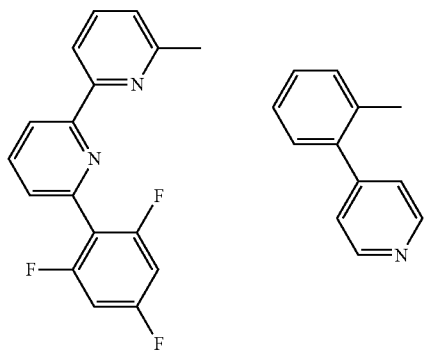

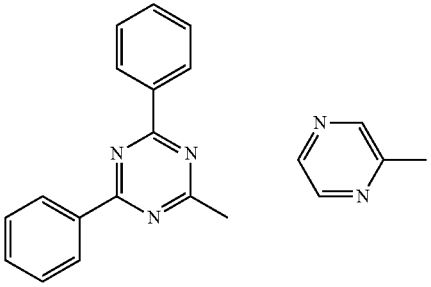

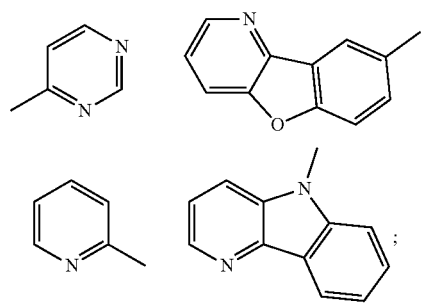

$L_1$ represents a divalent linking group selected from the group consisting of:

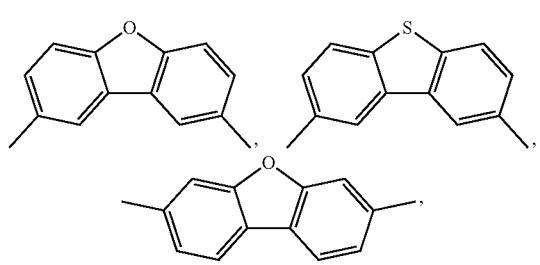

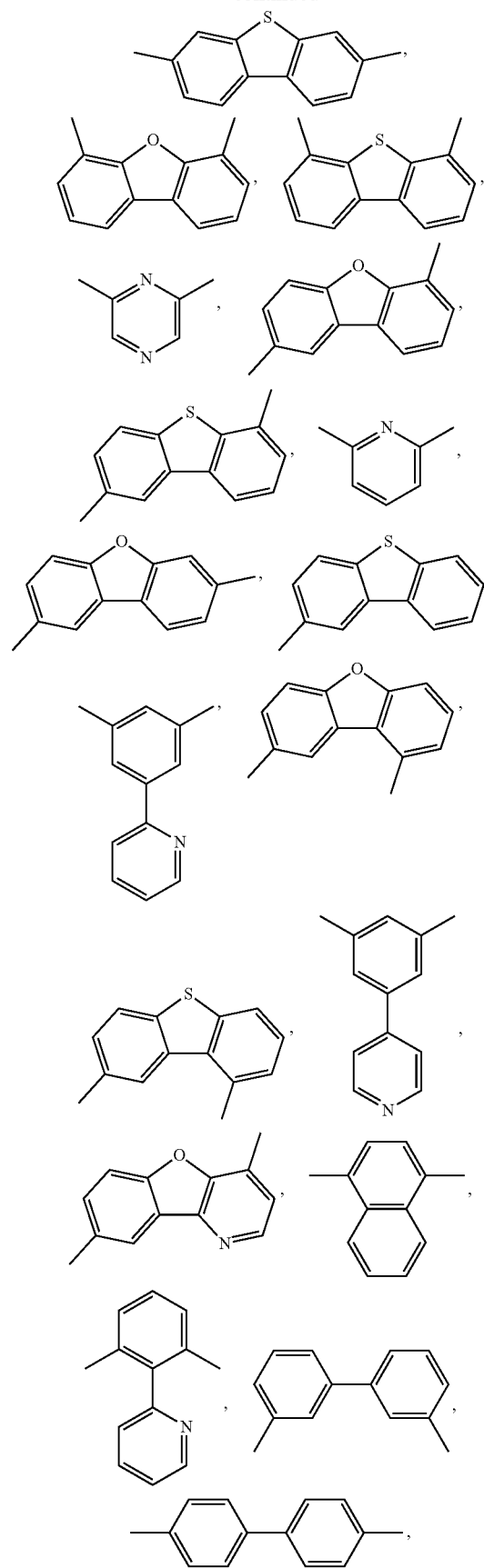

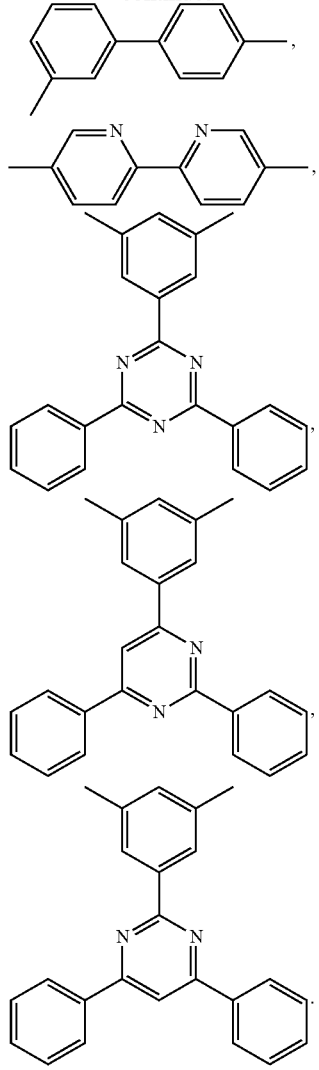

2. The organic electroluminescence element according to claim 1, wherein $X_5$ and $X_{10}$ represent a nitrogen atom.

3. The organic electroluminescence element according to claim 1, wherein $X_7$ and $X_8$ represent a nitrogen atom.

4. The organic electroluminescence element according to claim 1, wherein $X_5$ and $X_8$ represent a nitrogen atom.

5. The organic electroluminescence element according to claim 1, wherein $X_7$ and $X_{10}$ represent a nitrogen atom.

6. The organic electroluminescence element according to claim 1, wherein $X_1$ to $X_4$ represent $CR_1$.

7. The organic electroluminescence element according to claim 1, wherein at least one of $X_1$ to $X_4$ represents a nitrogen atom.

8. The organic electroluminescence element according to claim 1,
wherein the cathode comprises silver as a main component, and
wherein the organic functional layer containing the compound having the structure represented by the general formula (2) is provided adjacent to the cathode.

9. The organic electroluminescence element according to claim 1, wherein the cathode has a thickness of 15 nm or less.

10. The organic electroluminescence element according to claim 1, wherein the cathode has a light transmittance of 50% or more, and wherein the cathode has a sheet resistance value of 25Ω/☐ or less.

11. The organic electroluminescence element according to claim 1, wherein the organic functional layer containing the compound having the structure represented by the general formula (2) further comprises an electron injection material.

12. The organic electroluminescence element according to claim 1, wherein the organic functional layer containing the compound having the structure represented by the general formula (2), an electron injection layer containing an electron injection material, and the cathode are stacked in that order.

* * * * *